(12) United States Patent
Ohdachi et al.

(10) Patent No.: US 11,932,657 B2
(45) Date of Patent: Mar. 19, 2024

(54) HETEROCYCLIC COMPOUND

(71) Applicant: OTSUKA PHARMACEUTICAL CO., LTD., Tokyo (JP)

(72) Inventors: Kazuhiro Ohdachi, Osaka (JP); Yusuke Fujimori, Osaka (JP); Naoya Makita, Osaka (JP); Noritaka Koseki, Osaka (JP); Hideki Hayashi, Osaka (JP); Yuki Sakamoto, Osaka (JP); Kurumi Mineno, Osaka (JP); Ryosuke Taga, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 494 days.

(21) Appl. No.: 17/271,479

(22) PCT Filed: Sep. 6, 2019

(86) PCT No.: PCT/JP2019/035233
§ 371 (c)(1),
(2) Date: Feb. 25, 2021

(87) PCT Pub. No.: WO2020/050409
PCT Pub. Date: Mar. 12, 2020

(65) Prior Publication Data
US 2021/0340157 A1   Nov. 4, 2021

(30) Foreign Application Priority Data

Sep. 7, 2018   (JP) .................. 2018-167488

(51) Int. Cl.
*C07D 513/14*   (2006.01)
*C07D 498/14*   (2006.01)
*C07D 519/00*   (2006.01)

(52) U.S. Cl.
CPC ......... *C07D 513/14* (2013.01); *C07D 498/14* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 10,947,504 B2 | 3/2021 | Eto et al. | |
| 2019/0048317 A1 | 2/2019 | Eto et al. | |
| 2021/0340157 A1 | 11/2021 | Ohdachi et al. | |

FOREIGN PATENT DOCUMENTS

| | | | | |
|---|---|---|---|---|
| EP | 3 312 270 A1 | 4/2018 | | |
| JP | 2022-188761 A | 12/2022 | | |
| WO | 2010/059401 A2 | 5/2010 | | |
| WO | 2012/082997 A1 | 6/2012 | | |
| WO | 2014/138485 A1 | 9/2014 | | |
| WO | WO-2014138485 A1 * | 9/2014 | .............. | A61P 7/00 |
| WO | 2016/204256 A1 | 12/2016 | | |
| WO | 2018/195397 A2 | 10/2018 | | |
| WO | 2019/167973 A1 | 9/2019 | | |
| WO | 2020/050409 A1 | 3/2020 | | |
| WO | 2021/117733 A1 | 6/2021 | | |

OTHER PUBLICATIONS

International Preliminary Report on Patentability with the Written Opinion dated May 17, 2022 from the International Bureau in International Application No. PCT/JP2020/045713, corresponding to U.S. Appl. No. 17/766,948.
Perron et al., "Small-molecule screening yields a compound that inhibits the cancer-associated transcription factor Hes1 via the PHB2 chaperone", J. Biol. Chem., 2018, vol. 293, No. 21, pp. 8285-8294 (10 pages total).
Li et al., "Design, synthesis and antiproliferative activities of novel benzamides derivatives as HDAC inhibitors", European Journal of Medicinal Chemistry, vol. 100, 2015, pp. 270-276 (7 pages total).
Baytas et al., "Synthesis, biological evaluation and molecular docking studies of trans-indole-3-acrylamide derivatives, a new class of tubulin polymerization inhibitors", Bioorg. Med. Chem., vol. 22, 2014, pp. 3096-3104 (9 pages total).
International Search Report dated Feb. 1, 2021 from the International Searching Authority in International Application No. PCT/JP2020/045713.
International Search Report dated Nov. 19, 2019 in International Application No. PCT/JP2019/035233.
International Preliminary Report on Patentability dated Mar. 9, 2021 in International Application No. PCT/JP2019/035233.
K.J. Smith et al., "Identification of a High-Affinity Ligand That Exhibits Complete Aryl Hydrocarbon Receptor Antagonism", The Journal of Pharmacology and Experimental Therapeutics, 2011, vol. 338, No. 1, pp. 318-327 (10 pages total).
Iman Fares et al., "Pyrimidoindole derivatives are agonists of human hematopoietic stem cell self-renewal", Science, 2014, vol. 345, Issue 6203, pp. 1509-1512 (5 pages total).

(Continued)

*Primary Examiner* — Joseph R Kosack
(74) *Attorney, Agent, or Firm* — Sughrue Mion, PLLC

(57) ABSTRACT

Provided is a novel heterocyclic compound having an aryl hydrocarbon receptor antagonist activity and useful for the promotion of platelet production, the compound being represented by the general formula [I]: wherein ring A, ring B, $R^1$, $R^2$, $R^3$, $R^4$, n, and X are as defined above, or a salt thereof.

8 Claims, No Drawings

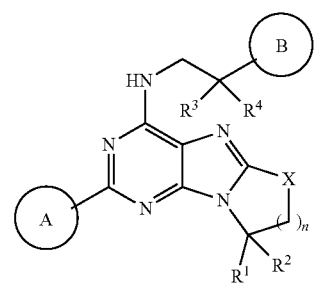

(56) References Cited

OTHER PUBLICATIONS

Takayama et al., "Generation of functional platelets from human embryonic stem cells in vitro via ES-sacs, VEGF-promoted structures that concentrate hematopoietic progenitors", Blood, 2008, vol. 111, No. 11, pp. 5298-5306 (9 pages total).
Boitano et al., "Aryl Hydrocarbon Receptor Antagonists Promote the Expansion of Human Hematopoietic Stem Cells", Science, 2010, vol. 329, pp. 1345-1348 (6 pages total).
Strassel et al., "Aryl hydrocarbon receptor-dependent enrichment of a megakaryocytic precursor with a high potential to produce proplatelets", Blood, 2016, vol. 127, No. 18, pp. 2231-2240 (10 pages total).
Ito et al., "Turbulence Activates Platelet Biogenesis to Enable Clinical Scale Ex Vivo Production", Cell, 2018, vol. 174, pp. 636-648 (32 pages total).

\* cited by examiner

HETEROCYCLIC COMPOUND

CROSS REFERENCE TO RELATED APPLICATIONS

This application is a National Stage of International Application No. PCT/JP2019/035233 filed Sep. 6, 2019, claiming priority based on Japanese Patent Application No. 2018-167488 filed Sep. 7, 2018.

TECHNICAL FIELD

The present invention relates to a heterocyclic compound. More specifically, the present invention relates to a compound having an aryl hydrocarbon receptor (AhR) antagonist activity and promoting production of platelets from platelet progenitor cells such as megakaryocytes in vitro.

BACKGROUND ART

Platelet preparations are administrated to patients who suffer from massive bleeding during surgery or injury, or tend to bleed due to decrease of platelets after treatment with an anti-cancer agent for treatment of the symptom and for prevention of un-expected bleeding.

Currently, the platelet preparations are dependent on the donation of blood, and the storage period is about 4 days, which is extremely short. Further, as long as the platelet preparations are supplied by the donation of blood only, it is expected that decrease in the number of blood donors may lead to shortage of platelet preparations in near future.

In order to meet these needs, a method for producing platelets in vitro has been studied.

As the method for producing platelets in vitro, a method for obtaining megakaryocytes by differentiating various types of stem cells followed by the culturing thereof to release platelets into the medium has been developed. Takayama, et al., for example, have succeeded in inducing human ES cells to differentiate into megakaryocytes and platelets (NPL 1).

In addition, as a method for producing platelets from hematopoietic progenitor cells in vitro, a method of culturing hematopoietic progenitor cells in the presence of an aryl hydrocarbon receptor antagonist and thrombopoietin (TPO) or a Rho-associated coiled-coil forming kinase (ROCK) inhibitor has been proposed (PTL 1, 2, and 3, and NPL 2, 3 and 4).

CITATION LIST

Patent Literature

[PTL 1] WO 2014/138485
[PTL 2] WO 2016/204256
[PTL 3] WO 2010/059401

Non Patent Literature

[NPL 1] Takayama et al., Blood, 111, 5298 (2008)
[NPL 2] Boitano et al., Science, 329, 1345 (2010)
[NPL 3] Strassel et al., Blood, 127, 2231 (2016)
[NPL 4] Ito et al., Cell, 174, 636 (2018)

DISCLOSURE OF INVENTION

Technical Problem

An object of the present invention is to provide a novel heterocyclic compound having an aryl hydrocarbon receptor antagonist activity and useful for the promotion of platelet production, or a salt thereof.

Solution to Problem

As a result of conducting extensive studies to solve the above-mentioned problems, the inventors of the present invention found that the compound represented by the following formula has an excellent aryl hydrocarbon receptor antagonist activity and has an effect of promoting platelet production, thereby leading to completion of the present invention.

Namely, the present invention includes the following embodiments.

[1] A compound represented by general formula [I]:

[Chem.1]

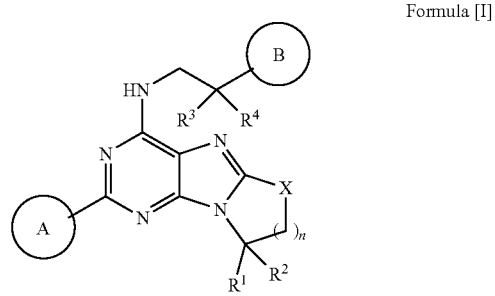

Formula [I]

wherein
$R^1$ and $R^2$ are the same or different and each independently represent hydrogen or $C_{1-6}$ alkyl;
$R^3$ and $R^4$ are the same or different and each independently represent hydrogen or $C_{1-6}$ alkyl, or $R^3$ and $R^4$ are bonded together to form $C_{2-5}$ alkylene;
X represents O, S, or S(O);
n represents 1, 2, or 3; and
rings A and B are the same or different and each independently represent an optionally substituted hydrocarbon ring or an optionally substituted heterocyclic ring, and the hydrocarbon ring and the heterocyclic ring are further optionally bonded with an optionally substituted hydrocarbon ring and/or an optionally substituted heterocyclic ring, or a salt thereof.

[2] The compound according to [1], in which ring A is benzene, pyridine, cyclohexane, cyclohexene, thiophene, imidazopyridine, triazolopyridine, or quinoline, each of which is optionally substituted on the ring with 1 to 4 substituents which are the same or different and are each independently halogen, $C_{1-6}$ alkyl optionally substituted with halogen, —CN, —OR$^5$, —SR$^5$, —COOR$^5$, —C$_{1-6}$ alkylene-CONR$^5$R$^6$, —C$_{1-6}$ alkylene-OCOR$^5$, —CONR$^5$R$^6$, —NR$^5$COOR$^6$, —SO$_2$R$^5$, or —NR$^5$R$^6$ (wherein R$^5$ and R$^6$ are the same or different and each independently represent hydrogen or $C_{1-6}$ alkyl optionally substituted with halogen),
or a salt thereof.

[3] The compound according to [2], in which ring A is benzene or pyridine, each of which is optionally substituted on the ring with 1 to 4 substituents which are the same or different and are each independently halogen, $C_{1-6}$ alkyl optionally substituted with halogen, or —CN, or a salt thereof.

[4] The compound according to any of [1] to [3], in which ring B is benzene, biphenyl, pyridinylbenzene, thienylbenzene, benzothienylbenzene, indole, or 3,4-dihydro-1H-quinolin-2-one, each of which is optionally substituted on the ring with 1 to 4 substitutes which are the same or different and are each independently halogen, $C_{1-6}$ alkyl optionally substituted with halogen, —CN, —$OR^5$, —$SR^5$, —$COOR^5$, —$C_{1-6}$ alkylene-$CONR^5R^6$, —$C_{1-6}$ alkylene-$OCOR^5$, —$CONR^5R^6$, —$NR^5COOR^6$, —$SO_2R^5$, or —$NR^5R^6$ (wherein $R^5$ and $R^6$ are the same or different and each independently represent hydrogen or $C_{1-6}$ alkyl optionally substituted with halogen), or a salt thereof.

[5] The compound according to [4], in which ring B is benzene, biphenyl, pyridinylbenzene, thienylbenzene, benzothienylbenzene, or indole, each of which is optionally substituted on the ring with 1 to 4 substituents which are the same or different and are each independently halogen, $C_{1-6}$ alkyl optionally substituted with halogen, —CN, —$OR^5$, or —$SO_2R^5$ (wherein $R^5$ is hydrogen or $C_{1-6}$ alkyl optionally substituted with halogen), or a salt thereof.

[6] The compound according to any of [1] to [5], in which $R^1$ and $R^2$ are the same or different and are each independently hydrogen or methyl;

$R^3$ and $R^4$ each represent hydrogen;

X is O or S; and n is 1, or a salt thereof.

[7] The compound according to any of [1] to [6], in which ring B is represented by the following formulae:

[Chem.2]

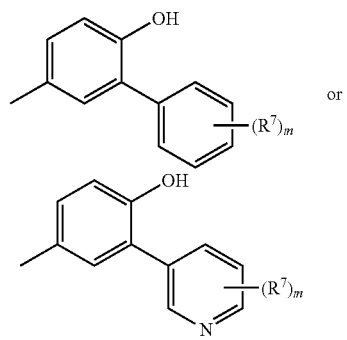

wherein $R^7$ is halogen, $C_{1-6}$ alkyl optionally substituted with halogen, —CN, —OR, or —$SO_2R^5$ (wherein $R^5$ represents hydrogen or $C_{1-6}$ alkyl optionally substituted with halogen); and m is 0, 1, or 2, wherein when m is 2, $R^7$ each independently represents the same or different substituent, or a salt thereof.

Advantageous Effect of Invention

The compound or a salt thereof of the present invention has an excellent aryl hydrocarbon receptor antagonist activity. Further, the compound or a salt thereof of the present invention has an efficacy of promoting production of platelets from platelet progenitor cells.

BEST MODE FOR CARRYING OUT THE INVENTION

The terms and phrases used in the present specification will be described in detail below.

In the present specification, "halogen" is fluorine, chlorine, bromine, or iodine. It is preferably fluorine, chlorine, or bromine, and more preferably fluorine or chlorine.

In the present specification, "$C_{1-6}$ alkyl" is linear or branched alkyl having 1 to 6 carbon atoms ($C_{1-6}$), and specific examples thereof include methyl, ethyl, n-propyl, isopropyl, n-butyl, isobutyl, sec-butyl, tert-butyl, n-pentyl, isopentyl, neopentyl, n-hexyl, isohexyl, 3-methylpentyl, and the like.

In addition, the "$C_{1-6}$ alkyl" includes $C_{1-6}$ alkyl in which 1 to 7 hydrogen atoms are substituted with deuterium atoms.

In the present specification, "$C_{1-6}$ alkyl optionally substituted with halogen" is linear or branched alkyl having 1 to 6 carbon atoms ($C_{1-6}$) optionally substituted with 1 to 4 halogens, preferably 1 to 3 halogens, and specific examples thereof include methyl, ethyl, n-propyl, isopropyl, n-butyl, isobutyl, tert-butyl, sec-butyl, n-pentyl, isopentyl, neopentyl, n-hexyl, isohexyl, 3-methylpentyl, fluoromethyl, chloromethyl, bromomethyl, iodomethyl, difluoromethyl, dichloromethyl, dibromomethyl, trifluoromethyl, trichloromethyl, 2-fluoroethyl, 2-chloroethyl, 2,2,2-trifluoroethyl, 2,2,2-trichloroethyl, 1,1,2,2-tetrafluoroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dibromohexyl, and the like.

In the present specification, "$C_{1-6}$ alkylene" is linear or branched alkylene having 1 to 6 carbon atoms ($C_10.6$), and specific examples thereof include methylene, ethylene, 1-methylethylene, 2-methylethylene, trimethylene, 2-methyltrimethylene, 2,2-dimethyltrimethylene, 1-methyltrimethylene, methylmethylene, ethylmethylene, dimethylmethylene, tetramethylene, pentamethylene, hexamethylene, and the like.

In the present specification, "$C_{2-5}$ alkylene" is linear or branched alkylene having 2 to 5 carbon atoms ($C_{2-5}$), and specific examples thereof include ethylene, 1-methylethylene, 2-methylethylene, trimethylene, 2-methyltrimethylene, 2,2-dimethyltrimethylene, 1-methyltrimethylene, methylmethylene, ethylmethylene, dimethylmethylene, tetramethylene, pentamethylene, and the like.

In the present specification, "hydrocarbon ring" is a saturated or unsaturated, monocyclic or polycyclic hydrocarbon ring, which includes, for example, a saturated or unsaturated 3- to 15-membered monocyclic, bicyclic, or tricyclic hydrocarbon ring. The "unsaturated" ring refers to an aromatic ring or a ring in which bonds between ring atoms of the aromatic ring are partially hydrogenated. The ring atom of the hydrocarbon ring may be substituted with oxo to form oxide or dioxide. Specific examples of the "hydrocarbon ring" include:

(a) a saturated or unsaturated 3- to 8-membered (preferably 5- or 6-membered) monocyclic hydrocarbon rings; specifically including cyclopropane, cyclobutane, cyclopentane, cyclohexane, cycloheptane, cyclooctane, cyclobutene, cyclopentene, cyclohexene, cycloheptene, cyclooctene, and benzene, and oxides and dioxides thereof; and (b) a saturated or unsaturated 7- to 15-membered bicyclic or tricyclic hydrocarbon rings, preferably saturated or unsaturated 7- to 12-membered bicyclic hydrocarbon rings; specifically including indene, dihydroindene, naphthalene, dihydronaphthalene, tetrahydronaphthalene, anthracene, and phenanthrene, and oxides and dioxides thereof.

In the present specification, the "heterocyclic ring" is a saturated or unsaturated monocyclic or polycyclic heterocyclic ring containing, as ring-constituting heteroatoms, 1 to 5 heteroatoms independently selected from the group consisting of nitrogen, oxygen, and sulfur, which includes, for example, a saturated or unsaturated 3-to 15-membered monocyclic, bicyclic, or tricyclic heterocyclic ring. The "unsaturated" ring refers to an aromatic ring or a ring in which bonds between ring atoms of the aromatic ring is partially hydrogenated. The "nitrogen-containing heterocyclic ring" refers to a heterocyclic ring containing at least one nitrogen as ring-constituting heteroatoms. The ring atom of the heterocyclic ring may be substituted with oxo to form oxide or dioxide. Specific examples of the "heterocyclic ring" include:

(a) a saturated or unsaturated 3- to 8-membered, preferably 3- to 6-membered, more preferably 5- or 6-membered monocyclic heterocyclic ring containing 1 to 4 nitrogen atoms alone as ring-constituting heteroatoms; specifically including pyrrole, imidazole, pyrazole, pyridine, tetrahydropyridine, pyrimidine, pyrazine, pyridazine, triazole, tetrazole, dihydrotriazine, azetidine, pyrrolidine, imidazolidine, piperidine, pyrazolidine, piperazine, azepane, and 1,4-diazepane, and oxides and dioxides thereof;

(b) a saturated or unsaturated 7- to 15-membered, bicyclic or tricyclic heterocyclic ring containing 1 to 5 nitrogen atoms alone as ring-constituting heteroatoms, preferably a saturated or unsaturated 7- to 12-membered bicyclic or tricyclic heterocyclic ring containing 1 to 3 nitrogen atoms alone as ring-constituting heteroatoms; specifically including indole, indoline (dihydroindole), isoindole, isoindoline (dihydroisoindole), benzoimidazole, dihydrobenzoimidazole, indazole, indazoline (dihydroindazole), quinoline, dihydroquinoline, tetrahydroquinoline, decahydroquinoline, isoquinoline, dihydroisoquinoline, tetrahydroisoquinoline, benzotriazole, tetrazolopyridine, tetrazolopyridazine, dihydrotriazolopyridazine, imidazopyridine, naphthyridine, tetrahy-dronaphthyridine, hexahydronaphthyridine, cinnoline, quinoxaline, dihydro-quinoxaline, tetrahydroquinoxaline, quinazoline, dihydroquinazoline, tetrahydro-quinazoline, pyrazolopyridine, tetrahydropyridoindole, benzoazepine, tetrahydrobenzoazepine, carbazole, phenanthridine, and dihydrophenanthridine, and oxides and dioxides thereof;

(c) a saturated or unsaturated 3- to 8-membered (preferably 5- or 6-membered) monocyclic heterocyclic ring containing 1 or 2 oxygen atoms alone as ring-constituting heteroatoms; specifically including furan, tetrahydropyran, tetrahydrofuran, and dioxane, and oxides and dioxides thereof;

(d) a saturated or unsaturated 7- to 12-membered bicyclic heterocyclic ring containing 1 to 3 oxygen atoms alone as ring-constituting heteroatoms; specifically including benzofuran, dihydrobenzofuran, chroman, benzodioxole, and benzodioxane, and oxides and dioxides thereof;

(e) a saturated or unsaturated 3- to 8-membered (preferably 5- or 6-membered) monocyclic heterocyclic ring containing 1 sulfur atom alone as ring-constituting heteroatoms; specifically including thiophene, and oxides and dioxides thereof;

(f) a saturated or unsaturated 7- to 12-membered bicyclic heterocyclic ring containing 1 to 3 sulfur atoms alone as ring-constituting heteroatoms; specifically including benzothiophene, and oxides and dioxides thereof;

(g) a saturated or unsaturated 3- to 8-membered (preferably 5- or 6-membered) monocyclic heterocyclic ring containing, as ring-constituting heteroatoms, 1 or 2 oxygen atoms and 1 to 3 nitrogen atoms; specifically including oxazole, isoxazole, oxadiazole, and morpholine, and oxides and dioxides thereof;

(h) a saturated or unsaturated 7- to 12-membered bicyclic heterocyclic ring containing, as ring-constituting heteroatoms, 1 or 2 oxygen atoms and 1 to 3 nitrogen atoms; specifically including benzoxazole, dihydrobenzoxazole, benzoxadiazole, benzoisoxazole, benzoxazine, dihydrobenzoxazine, furopyridine, furopyrrole, benzoisoxazole, and tetrahydrobenzoxazepine, and oxides and dioxides thereof;

(i) a saturated or unsaturated 3- to 8-membered (preferably 5- or 6-membered) monocyclic heterocyclic ring containing, as ring-constituting heteroatoms, 1 or 2 sulfur atoms and 1 to 3 nitrogen atoms; specifically including thiazole, thiazoline (dihydrothiazole), thiadiazole, isothiazole, and thiazolidine, and oxides and dioxides thereof;

(j) a saturated or unsaturated 7- to 12-membered bicyclic heterocyclic ring containing, as ring-constituting heteroatoms, 1 or 2 sulfur atoms and 1 to 3 nitrogen atoms; specifically including benzothiazole, dihydrobenzothiazole, benzothiadiazole, thienopyridine, imidazothiazole, dihydroimidazothiazole, thienopyrazine, benzothiazine, dihydrobenzothiazine, benzothiazepine, and tetrahydrobenzothiazepine; and (k) a saturated or unsaturated 7- to 12-membered bicyclic heterocyclic ring containing, as ring-constituting heteroatoms, 1 or 2 oxygen atoms and 1 to 3 sulfur atoms; specifically including benzoxathiin, and oxide and dioxide thereof.

Each substituent in the compound represented by the general formula [I] of the present invention (hereinafter referred to as "compound [I] of the present invention") will be described below.

Ring A in compound [I] of the present invention is an optionally substituted hydrocarbon ring or an optionally substituted heterocyclic ring, the hydrocarbon ring and the heterocyclic ring are further optionally bonded with an optionally substituted hydrocarbon ring and/or an optionally substituted heterocyclic ring, and ring A is, for example, benzene, pyridine, cyclohexane, cyclohexene, thiophene, imidazopyridine, triazolopyridine, or quinoline, and preferably benzene or pyridine.

Ring B in compound [I] of the present invention is an optionally substituted hydrocarbon ring or an optionally substituted heterocyclic ring, the hydrocarbon ring and the heterocyclic ring are further optionally bonded with an optionally substituted hydrocarbon ring and/or an optionally substituted heterocyclic ring, and ring B is, for example, benzene, biphenyl, pyridinylbenzene, thienylbenzene, benzothienylbenzene, indole, or 3,4-dihydro-1H-quinolin-2-one, and preferably benzene, biphenyl, pyridinylbenzene, or indole.

In the present specification, part or all of the hydrogen atom on rings A and B is optionally substituted by deuterium atom.

Rings A and B in compound [I] of the present invention each optionally have 1 to 4 substituents, which are the same or different and are each independent, on the ring. The substituents are, for example, halogen, $C_{1-6}$ alkyl optionally substituted with halogen, —CN, —OR$^5$, —SR$^5$, —COOR$^5$, —C$_{1-6}$ alkylene-CONR$^5$R$^6$, —C$_{1-6}$ alkylene-OCOR$^5$, —CONR$^5$R$^6$, —NR$^5$COOR$^6$, —SO$_2$R$^5$, or —NR$^5$R$^6$.

The substituents on the ring A are preferably halogen, $C_{1-4}$ alkyl optionally substituted with halogen, or —CN.

The substituents on the ring B are preferably halogen, $C_{1-6}$ alkyl optionally substituted with halogen, —OR$^5$, or —CN.

Here, R$^5$ and R$^6$ are the same or different and are each independently hydrogen or $C_{1-6}$ alkyl optionally substituted with halogen.

R$^1$ and R$^2$ in compound [I] of the present invention are the same or different and are each independently hydrogen or $C_{1-6}$ alkyl, and preferably hydrogen or methyl.

R$^3$ and R$^4$ in compound [I] of the present invention are the same or different and are each independently hydrogen or $C_{1-6}$ alkyl, or R$^3$ and R$^4$-bonded $C_{2-5}$ alkylene; R$^3$ and R$^4$ are each preferably hydrogen or R$^3$ and R$^4$-bonded ethylene; and R$^3$ and R$^4$ are each further preferably hydrogen.

X in compound [I] of the present invention is O, S, or S(O), and preferably O or S.

n in compound [I] of the present invention is 1, 2, or 3, and preferably 1.

A preferred embodiment of compound [I] of the present invention will be described below:

(1) in the formula [I], ring A is benzene or pyridine, and hydrogen on the ring of the benzene or the pyridine is optionally substituted with fluorine, methyl, or —CN;

(2) in the formula [I], ring B is represented by the following formulae:

[Chem.3]

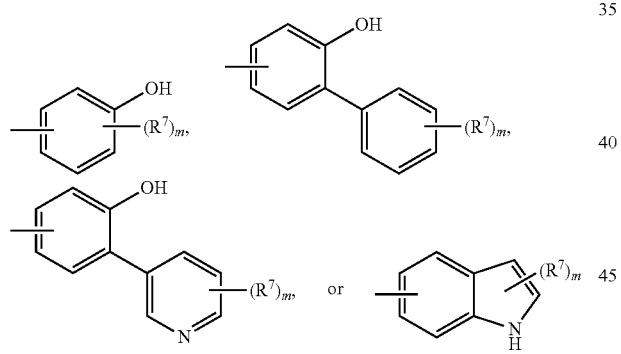

wherein R$^7$ is halogen, $C_{1-6}$ alkyl optionally substituted with halogen, —CN, —OR$^5$, —SR$^5$, —COOR$^5$, —C$_{1-6}$ alkylene-CONR$^5$R$^6$, —C$_{1-4}$ alkylene-OCOR$^5$, —CONR$^5$R$^6$, —NR$^5$COOR$^6$, —SO$_2$R$^5$, or —NR$^5$R$^6$ (R$^5$ and R$^6$ are the same or different and each independently represent hydrogen or $C_{1-6}$ alkyl optionally substituted with halogen), m is 0, 1, or 2, when m is 2, each of R$^7$ is independently the same or different substituent, for example, (R$^7$)m represents substitution with fluorine, two fluorines, chlorine, methyl, ethyl, trifluoromethyl, hydroxy, methoxy, —CN, —CON(CH$_3$)$_2$, —CH$_2$CON(CH$_3$)$_2$, methylsulfonyl, or one each of fluorine and —CN;

(3) in the formula [I], R$^1$ and R$^2$ are the same or different and are each independently hydrogen or methyl;

(4) in the formula [I], each of R$^3$ and R$^4$ is hydrogen;

(5) in the formula [I], X is O or S; and (6) in the formula [I], n is 1.

A further preferred embodiment of compound [I] of the present invention will be described below:

(1) in the formula [I], ring A is benzene or pyridine, and is optionally substituted with 1 or 2 fluorine, methyl, or —CN, which are the same or different and are each independent, on the ring of the benzene or the pyridine;

(2) in the formula [I], ring B is represented by the following formulae:

[Chem.4]

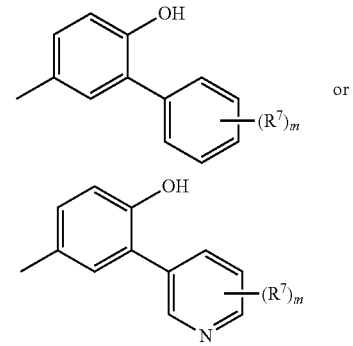

wherein R$^7$ is halogen, $C_{1-6}$ alkyl optionally substituted with halogen, —CN, —OR$^5$, or —SO$_2$R$^5$ (wherein R$^5$ represents hydrogen or $C_{1-6}$alkyl optionally substituted with halogen); and m is 0, 1, or 2, wherein when m is 2, R$^7$ each independently represents the same or different substituent, for example, (R$^7$)m represents substitution with each fluorine, two fluorines, chlorine, methyl, ethyl, trifluoromethyl, hydroxy, methoxy, —CN, methylsulfonyl, or one each of fluorine and —CN;

(3) in the formula [I], R$^1$ and R$^2$ are the same or different and are each independently hydrogen or methyl;

(4) in the formula [I], R$^3$ and R$^4$ each represent hydrogen;

(5) in the formula [I], X is O or S; and (6) in the formula [I], n is 1.

Another preferred embodiment of the present invention will be described below.

A compound selected from the group consisting of the following compounds, or a salt thereof.

[Chem. 5]

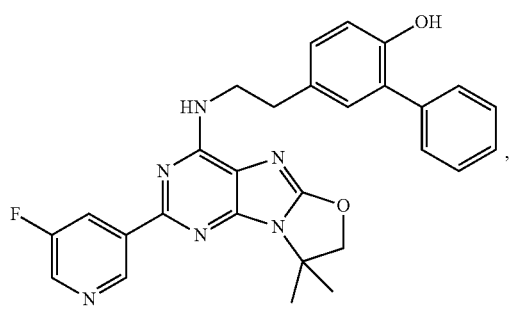

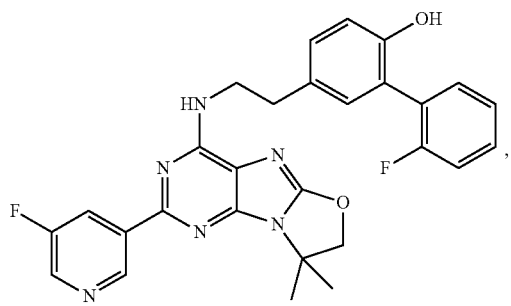
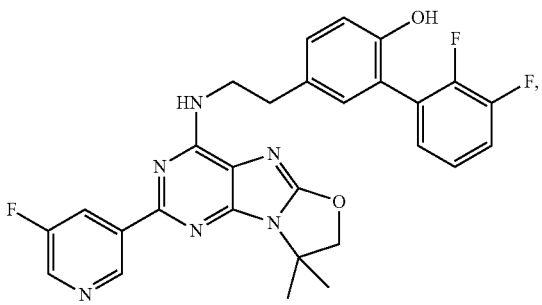

11
-continued
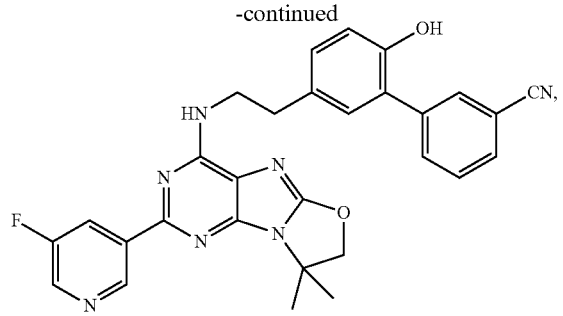
[Chem. 6]
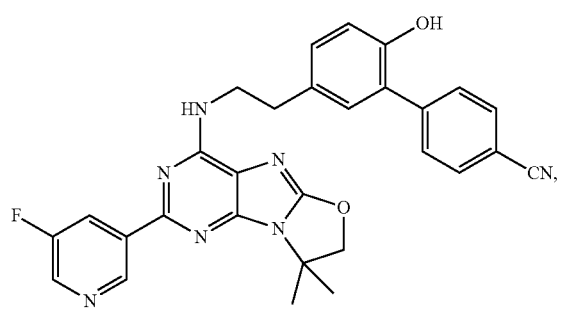
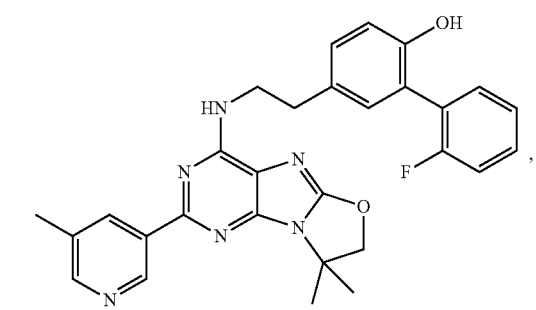
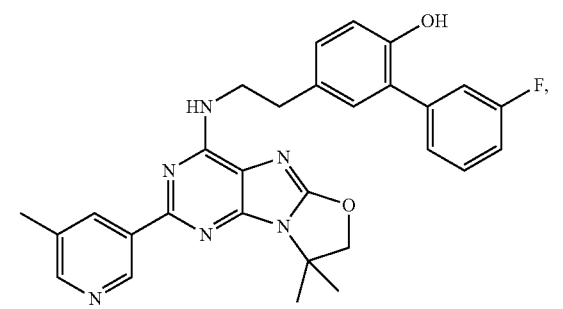
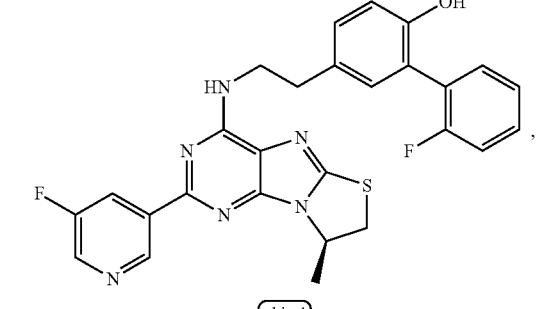
12
-continued
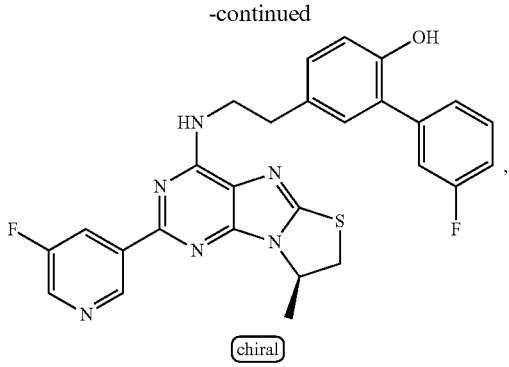
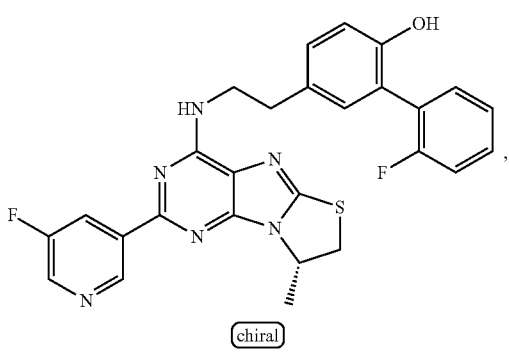
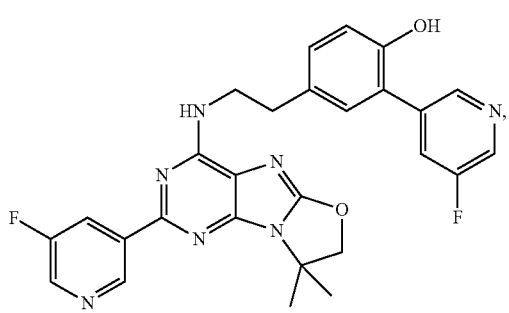
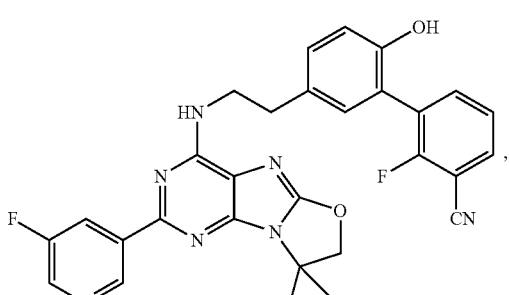
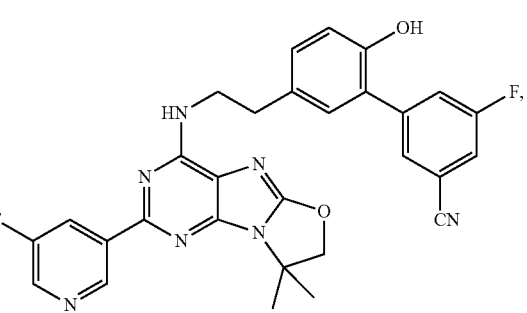

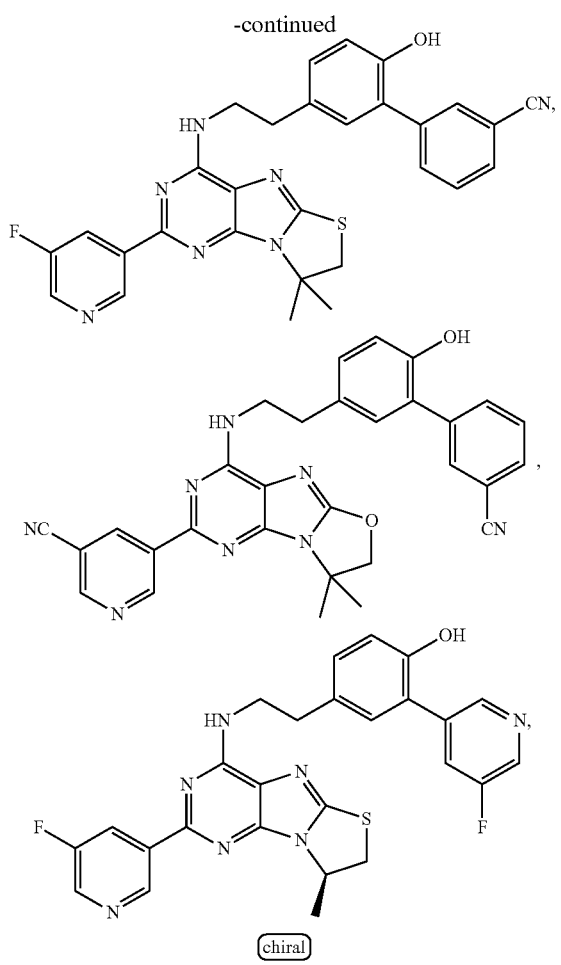

[Chem. 7]

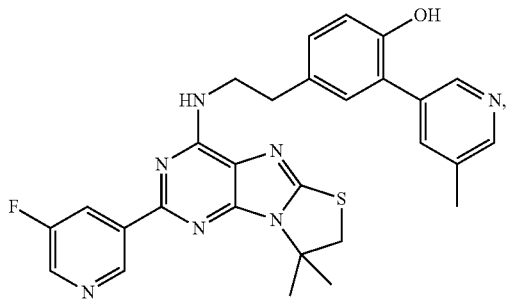

In the present specification, preferred embodiments and alternatives regarding diverse features of the compound, method, and composition of the present invention can be combined, and unless this is incompatible with the nature thereof, the presentation of the combination of preferred embodiments and alternatives regarding the diverse features is also included.

The method for manufacturing compound [I] of the present invention will be described below. Compound [I] of the present invention can be manufactured according to, for example, the method for manufacturing described below. The method for manufacturing described below is an example and the method for manufacturing compound [I] is not limited thereto.

In the reaction formulae below, in the case of performing alkylation reaction, hydrolysis reaction, amination reaction, esterification reaction, amidation reaction, etherification reaction, nucleophilic substitution reaction, addition reaction, oxidation reaction, reduction reaction, and the like, these reactions are performed according to methods known per se. Examples of such methods include the methods described in Experimental Chemistry (5th edition, The Chemical Society of Japan ed., Maruzen Co., Ltd.); Organic Functional Group Preparations, 2nd edition, Academic Press, Inc. (1989); Comprehensive Organic Transformations, VCH Publishers Inc. (1989); Greene's Protective Groups in Organic Synthesis, 4th edition, (2006) written by P. G. M. Wuts and T. W. Greene; and the like.

General Synthetic Pathway of Compound [I]

[Chem.8]

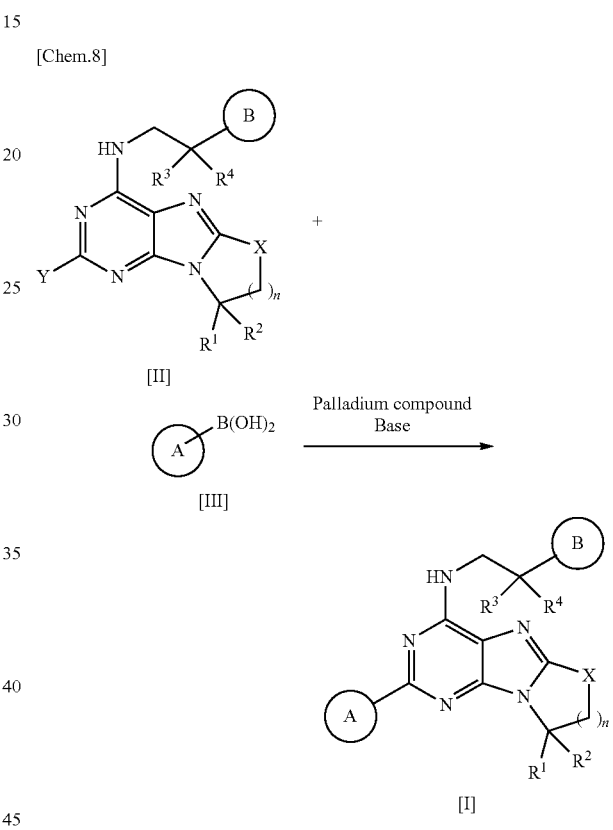

wherein ring A, ring B, $R^1$, $R^2$, $R^3$, $R^4$, n, and X are as defined above, and Y represents a leaving group.

Compound [I] of the present invention can be manufactured by the reaction indicated by the synthetic pathway described above. Specifically, compound [II] having a leaving group (Y) is subjected to the Suzuki cross-coupling reaction with compound [III] in the presence of a palladium compound, so that compound [I] can be manufactured.

Specific examples of the "leaving group" used in the above-mentioned reaction include halogen, $C_{1-18}$ alkanesulfonyl, lower alkanesulfonyloxy, arylsulfonyloxy, aralkylsulfonyloxy, perhaloalkanesulfonyloxy, sulfonio, toluenesulfoxy, and the like. A preferable leaving group in the present reaction is halogen.

The "halogen" is fluorine, chlorine, bromine, or iodine.

Examples of the "$C_{1-18}$ alkanesulfonyl" include linear or branched alkanesulfonyl having 1 to 18 carbon atoms, and specific examples thereof include methanesulfonyl, 1-propanesulfonyl, 2-propanesulfonyl, butanesulfonyl, cyclohexanesulfonyl, dodecane-sulfonyl, octadecanesulfonyl, and the like.

Examples of the "lower alkanesulfonyloxy" include linear or branched alkanesulfonyloxy having 1 to 6 carbon atoms, and specific examples thereof include methane-sulfonyloxy, ethanesulfonyloxy, 1-propanesulfonyloxy, 2-propanesulfonyloxy, 1-butanesulfonyloxy, 3-butanesulfonyloxy, 1-pentanesulfonyloxy, 1-hexanesulfonyloxy, and the like.

Examples of the "arylsulfonyloxy" include phenylsulfonyloxy optionally having 1 to 3 groups selected from the group consisting of linear or branched alkyl having 1 to 6 carbon atoms, linear or branched alkoxy having 1 to 6 carbon atoms, nitro, and halogen, as a substituent on the phenyl ring, naphthylsulfonyloxy, and the like. Specific examples of the "phenylsulfonyloxy optionally having substituent(s)" include phenylsulfonyloxy, 4-methylphenylsulfonyloxy, 2-methylphenylsulfonyloxy, 4-nitrophenylsulfonyloxy, 4-methoxyphenylsulfonyloxy, 2-nitrophenylsulfonyloxy, 3-chlorophenylsulfonyloxy, and the like. Specific examples of the "naphthylsulfonyloxy" include α-naphthylsulfonyloxy, β-naphthylsulfonyloxy, and the like.

Examples of the "aralkylsulfonyloxy" include linear or branched alkanesulfonyloxy having 1 to 6 carbon atoms, which is substituted by phenyl optionally having 1 to 3 groups selected from the group consisting of linear or branched alkyl having 1 to 6 carbon atoms, linear or branched alkoxy having 1 to 6 carbon atoms, nitro, and halogen, as a substituent on the phenyl ring; and linear or branched alkanesulfonyloxy having 1 to 6 carbon atoms, which is substituted by naphthyl, and the like. Specific examples of the "alkanesulfonyloxy substituted by phenyl" include benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy, and the like. Specific examples of the "alkanesulfonyloxy substituted by naphthyl" include α-naphthylmethylsulfonyloxy, β-naphthylmethylsulfonyloxy, and the like.

Specific examples of the "perhaloalkanesulfonyloxy" include trifluoromethanesul-fonyloxy and the like.

Specific examples of the "sulfonio" include dimethylsulfonio, diethylsulfonio, dipropylsulfonio, di(2-cyanoethyl)sulfonio, di(2-nitroethyl)sulfonio, di-(aminoethyl)sulfonio, di(2-methylaminoethyl)sulfonio, di-(2-dimethylaminoethyl)sulfonio, di-(2-hydroxyethyl)sulfonio, di-(3-hydroxypropyl)sulfonio, di-(2-methoxyethyl)sulfonio, di-(2-carbamoylethyl)sulfonio, di-(2-carbamoylethyl)sulfonio, di-(2-carboxyethyl)sulfonio, di-(2-methoxycarbonylethyl)sulfonio, or diphenylsulfonio, and the like.

The "palladium compound" to be used in the present reaction is not particularly limited, and examples thereof include tetravalent palladium catalysts such as sodium hexachloropalladium (IV) acid tetrahydrate and potassium hexachloropalladium (IV) acid; divalent palladium catalysts such as
[1,1'-bis(diphenylphosphino)ferrocene]palladium(II) dichloride dichloromethane adduct (Pd(dppf)Cl$_2$CH$_2$Cl$_2$), (2-dicyclohexylphosphino-2',4',6'-triisopropyl-1,1'-biphenyl)[2-(2'-amino-1,1'-biphenyl)]palladium(II) methanesulfonate (XPhos Pd G3), palladium(II) chloride, palladium (II) bromide, palladium(II) acetate, palladium(II) acetylacetonate, dichlorobis(benzonitrile)palladium(II), dichlorobis(acetonitrile)palladium(II), dichlorobis(triphenylphosphine)palladium(II), dichlorotetraammine palladium(II), dichloro(cycloocta-1,5-diene)palladium(II), and palladium(II) trifluoroacetate; and zerovalent palladium catalysts such as tris(dibenzylideneacetone)dipalladium(0) (Pd$_2$ (dba)$_3$), tris(dibenzylideneacetone)dipalladium(0)-chloroform complex, and tetrakis(triphenylphosphine)palladium(0) (Pd(PPh$_3$)$_4$). These palladium compounds are used alone or as a mixture of two or more of them.

In the present reaction, the amount of the palladium compound used is not particularly limited and is usually in the range of 0.000001 to 20 mol in terms of palladium with respect of 1 mol of compound [II]. More preferably, the amount of the palladium compound used is in the range of 0.0001 to 5 mol in terms of palladium with respect of 1 mol of compound [II].

Examples of the "base" to be used in the present reaction include an inorganic base, an organic base, and the like. Examples of the "inorganic base" include an alkali metal hydroxide (e.g., sodium hydroxide and potassium hydroxide), an alkaline earth metal hydroxide (e.g., magnesium hydroxide and calcium hydroxide), an alkali metal carbonate (e.g., sodium carbonate and potassium carbonate), an alkaline earth metal carbonate (e.g., magnesium carbonate and calcium carbonate), an alkali metal hydrogen carbonate (e.g., sodium hydrogen carbonate and potassium hydrogen carbonate), an alkali metal phosphate (e.g., sodium phosphate and potassium phosphate), an alkaline earth metal phosphate (e.g., magnesium phosphate and calcium phosphate). Examples of the "organic base" include trialkylamines (e.g., trimethylamine and triethylamine), picoline, 1,5-diazabicyclo[4.3.0]non-5-ene, 1,4-diazabicyclo[2.2.2]octane, and 1,8-diazabicyclo[5.4.0]undec-7-ene.

The "boronic acid" or "boronic ester" to be used in the present reaction may be separately manufactured, and isolated and purified. For example, bispinacol diborane is subjected to reaction with a halogenated compound as a precursor in the presence of the palladium compound, and the resulting product is subjected to Suzuki cross-coupling reaction without isolation and purification.

The "solvent" to be used in the present reaction may be an inert solvent in the reaction, and examples thereof include water, ethers (e.g., dioxane, tetrahydrofuran, diethyl ether, 1,2-dimethoxyethane, diethylene glycol dimethyl ether, and ethylene glycol dimethyl ether), halohydrocarbons (e.g., methylene chloride, chloroform, 1,2-dichloroethane, and carbon tetrachloride), aromatic hydrocarbons (e.g., benzene, toluene, and xylene), lower alcohols (e.g., methanol, ethanol, and isopropanol), and polar solvents (e.g., N,N-dimethylformamide (DMF), N-methylpyrrolidone (NMP), dimethyl sulfoxide (DMSO), hexamethylphosphoric triamide, and acetonitrile). These solvents are used alone or as a mixture of two or more of them.

Other reaction conditions (reaction temperature, reaction time, etc.) can be appropriately determined based on the known Suzuki cross-coupling reaction.

Addition reaction of amine side chain-tricyclic system

[Chem.9]

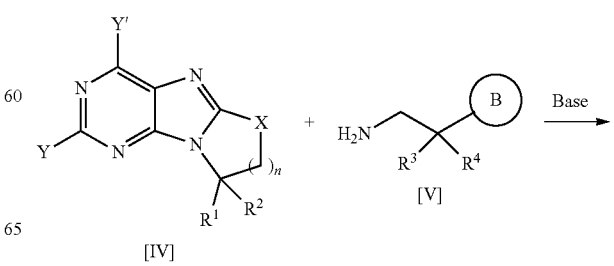

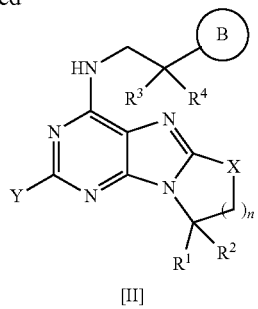

[II]

wherein ring B, R¹, R², R³, R⁴, n, X, and Y are as defined above, and Y' represents a leaving group.

Intermediate [II] of compound [I] of the present invention can be manufactured by the reaction indicated by the synthetic pathway described above. Specifically, intermediate [II] can be manufactured by subjecting compound [IV] to addition reaction with compound [V] in the presence of the base.

The leaving group (Y') includes a group similar to the above-mentioned leaving group (Y). Y and Y' may be the same or different as long as the above-mentioned reaction proceeds.

Examples of the "base" to be used in the present reaction include an inorganic base, an organic base, and the like. Examples of the "inorganic base" include an alkali metal hydroxide (e.g., sodium hydroxide and potassium hydroxide), an alkaline earth metal hydroxide (e.g., magnesium hydroxide and calcium hydroxide), an alkali metal carbonate (e.g., sodium carbonate and potassium carbonate), an alkaline earth metal carbonate (e.g., magnesium carbonate and calcium carbonate), an alkali metal hydrogen carbonate (e.g., sodium hydrogen carbonate and potassium hydrogen carbonate), an alkali metal phosphate (e.g., sodium phosphate and potassium phosphate), an alkaline earth metal phosphate (e.g., magnesium phosphate and calcium phosphate). Examples of the "organic bases" include trialkylamines (e.g., trimethylamine, triethylamine, and diisopropylethylamine), picoline, 1,5-diazabicyclo[4.3.0]non-5-ene, 1,4-diazabicyclo[2.2.2]octane, and 1,8-diazabicyclo[5.4.0]undec-7-ene.

The "solvent" to be used in the present reaction may be an inert solvent in the reaction, and examples thereof include water, ethers (e.g., dioxane, tetrahydrofuran, diethyl ether, 1,2-dimethoxyethane, diethylene glycol dimethyl ether, and ethylene glycol dimethyl ether), halohydrocarbons (e.g., methylene chloride, chloroform, 1,2-dichloroethane, and carbon tetrachloride), aromatic hydrocarbons (e.g., benzene, toluene, and xylene), lower alcohols (e.g., methanol, ethanol, and isopropanol), and polar solvents (e.g., N,N-dimethylformamide (DMF), N-methylpyrrolidone (NMP), dimethyl sulfoxide (DMSO), hexamethylphosphoric triamide, and acetonitrile). These solvents are used alone or as a mixture of two or more of them.

Other reaction conditions (reaction temperature, reaction time, etc.) can be appropriately determined based on a known addition reaction.

General synthetic pathway 1 of tricyclic system (X=O)

[Chem.10]

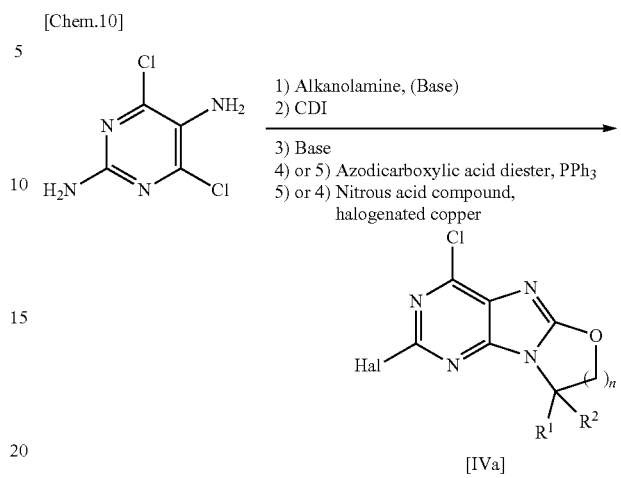

[IVa]

wherein R¹, R², and n are as defined above, and Hal represents halogen. Intermediate compound [IVa] of compound [I] of the present invention can be manufactured by the reaction indicated by the synthetic pathway described above. Specifically, alkanolamine suitable for manufacturing of a desired compound is substituted for 2,5-diamino-4,6-dichloropyrimidine in the presence or absence of a base, and then subjected to base treatment by reaction with 1,1'-carbonyldiimidazole (CDI). Thereafter, the resulting product undergoes ring closure by Mitsunobu reaction using azodicarboxylic acid diester in the presence of triphenylphosphine. Further, amine is diazotized with a nitrous acid compound by Sandmeyer reaction, and the resulting product is then halogenated by reaction with halogenated copper, to thereby achieve synthesis.

It should be noted that the ring closure reaction by the above-mentioned Mitsunobu reaction and the halogenation by the above-mentioned Sandmeyer reaction may change their orders. That is, the halogenation may be performed before the ring closure reaction is performed.

The "alkanolamine" to be used in the present reaction constitutes a desired skeleton, and examples thereof include 2-amino-2-methyl-1-propanol, 2-aminoethanol, 3-amino-1-propanol, 3-amino-3-methyl-1-butanol, (2R)-2-amino-1-hydroxypropane, (2S)-2-amino-1-hydroxypropane, and 4-amino-1-butanol.

Examples of the "base" to be used in the presence of a base in the present reaction include an inorganic base, an organic base, and the like. Examples of the "inorganic base" include an alkali metal hydroxide (e.g., sodium hydroxide and potassium hydroxide), an alkaline earth metal hydroxide (e.g., magnesium hydroxide and calcium hydroxide), an alkali metal carbonate (e.g., sodium carbonate and potassium carbonate), an alkaline earth metal carbonate (e.g., magnesium carbonate and calcium carbonate), an alkali metal hydrogen carbonate (e.g., sodium hydrogen carbonate and potassium hydrogen carbonate), an alkali metal phosphate (e.g., sodium phosphate and potassium phosphate), an alkaline earth metal phosphate (e.g., magnesium phosphate and calcium phosphate). Examples of the "organic bases" include trialkylamines (e.g., trimethylamine, triethylamine, and diisopropylethylamine), picoline, 1,5-diazabicyclo[4.3.0]non-5-ene, 1,4-diazabicyclo[2.2.2]octane, and 1,8-diazabicyclo[5.4.0]undec-7-ene.

Examples of the "azodicarboxylic acid diester" to be used in the present reaction include dimethyl azodicarboxylate, diethyl azodicarboxylate, diisopropyl azodicarboxylate, di-tert-butyl azodicarboxylate, and bis-2-methoxyethyl azodicarboxylate.

The "solvent" in the present reaction may be an inert solvent in the reaction, and examples thereof include water, ethers (e.g., dioxane, tetrahydrofuran, diethyl ether, 1,2-dimethoxyethane, diethylene glycol dimethyl ether, and ethylene glycol dimethyl ether), halohydrocarbons (e.g., methylene chloride, chloroform, 1,2-dichloroethane, and carbon tetrachloride), aromatic hydrocarbons (e.g., benzene, toluene, and xylene), lower alcohols (e.g., methanol, ethanol, and isopropanol), and polar solvents (e.g., N,N-dimethylformamide (DMF), N-methylpyrrolidone (NMP), dimethyl sulfoxide (DMSO), hexamethylphosphoric triamide, and acetonitrile). These solvents are used alone or as a mixture of two or more of them. Alternatively, the reaction can be performed without solvent.

Examples of the "nitrous acid compound" to be used in the Sandmeyer reaction include sodium nitrite, potassium nitrite, methyl nitrite, ethyl nitrite, n-propyl nitrite, isopropyl nitrite, isobutyl nitrite, n-butyl nitrite, tert-butyl nitrite, n-pentyl nitrite, and isoamyl nitrite.

The "halogenated copper" to be used in the Sandmeyer reaction include copper fluoride, copper chloride, copper bromide, and copper iodide.

Other reaction conditions (reaction temperature, reaction time, etc.) can be appropriately determined based on a known reaction.

General synthetic pathway 2 of tricyclic system (X═S)

[Chem.11]

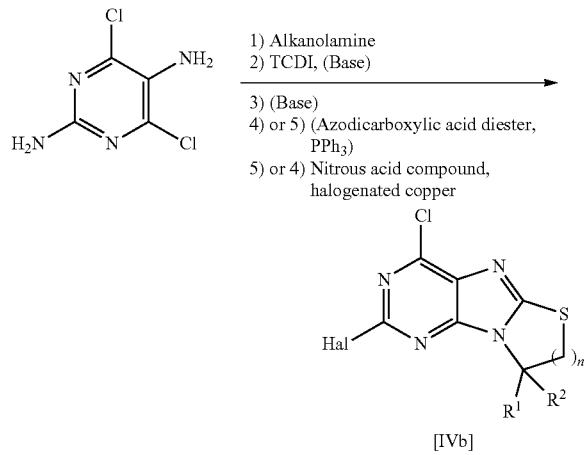

wherein $R^1$, $R^2$, and n are as defined above, and Hal represents halogen.

Intermediate compound [IVb] of compound [I] of the present invention can be manufactured by the reaction indicated by the synthetic pathway described above. Specifically, alkanolamine suitable for manufacturing of the objective compound is substituted for 2,5-diamino-4,6-dichloropyrimidine, and then subjected to reaction with 1,1'-thiocarbonyldiimidazole (TCDI). If ring closure is not achieved, the resulting product undergoes reaction with a base, or after the base treatment, the resulting product undergoes ring closure by Mitsunobu reaction using azodicarboxylic acid diester in the presence of triphenylphosphine. Further, amine is diazotized with a nitrous acid compound by Sandmeyer reaction, and the resulting product is then halogenated by reaction with halogenated copper, to thereby achieve synthesis.

It should be noted that the ring closure reaction by the above-mentioned Mitsunobu reaction and the halogenation by the above-mentioned Sandmeyer reaction may change their orders.

The "alkanolamine" to be used in the present reaction constitutes a desired skeleton, and examples thereof include 2-amino-2-methyl-1-propanol, 2-aminoethanol, 3-amino-1-propanol, 3-amino-3-methyl-1-butanol, (2R)-2-amino-1-hydroxypropane, (2S)-2-amino-1-hydroxypropane, and 4-amino-1-butanol.

Examples of the "base" to be used in the presence of a base in the present reaction include an inorganic base, an organic base, and the like. Examples of the "inorganic base" include an alkali metal hydroxide (e.g., sodium hydroxide and potassium hydroxide), an alkaline earth metal hydroxide (e.g., magnesium hydroxide and calcium hydroxide), an alkali metal carbonate (e.g., sodium carbonate and potassium carbonate), an alkaline earth metal carbonate (e.g., magnesium carbonate and calcium carbonate), an alkali metal hydrogen carbonate (e.g., sodium hydrogen carbonate and potassium hydrogen carbonate), an alkali metal phosphate (e.g., sodium phosphate and potassium phosphate), an alkaline earth metal phosphate (e.g., magnesium phosphate and calcium phosphate). Examples of the "organic bases" include trialkylamines (e.g., trimethylamine, triethylamine, and diisopropylethylamine), picoline, 1,5-diazabicyclo[4.3.0]non-5-ene, 1,4-diazabicyclo[2.2.2]octane, and 1,8-diazabicyclo[5.4.0]undec-7-ene.

Examples of the "azodicarboxylic acid diester" to be used in the present reaction include dimethyl azodicarboxylate, diethyl azodicarboxylate, diisopropyl azodicarboxylate, di-tert-butyl azodicarboxylate, and bis-2-methoxyethyl azodicarboxylate.

The "solvent" in the present reaction may be an inert solvent in the reaction, and examples thereof include water, ethers (e.g., dioxane, tetrahydrofuran, diethyl ether, 1,2-dimethoxyethane, diethylene glycol dimethyl ether, and ethylene glycol dimethyl ether), halohydrocarbons (e.g., methylene chloride, chloroform, 1,2-dichloroethane, and carbon tetrachloride), aromatic hydrocarbons (e.g., benzene, toluene, and xylene), lower alcohols (e.g., methanol, ethanol, and isopropanol), and polar solvents (e.g., N,N-dimethylformamide (DMF), N-methylpyrrolidone (NMP), dimethyl sulfoxide (DMSO), hexamethylphosphoric triamide, and acetonitrile). These solvents are used alone or as a mixture of two or more of them. Alternatively, the reaction can be performed without solvent.

Examples of the "nitrous acid compound" to be used in the Sandmeyer reaction include sodium nitrite, potassium nitrite, methyl nitrite, ethyl nitrite, n-propyl nitrite, isopropyl nitrite, isobutyl nitrite, n-butyl nitrite, tert-butyl nitrite, n-pentyl nitrite, and isoamyl nitrite.

The "halogenated copper" to be used in the Sandmeyer reaction include copper fluoride, copper chloride, copper bromide, and copper iodide.

Other reaction conditions (reaction temperature, reaction time, etc.) can be appropriately determined based on a known reaction.

General synthetic pathway 3 of tricyclic system (X=SO)

[Chem.12]

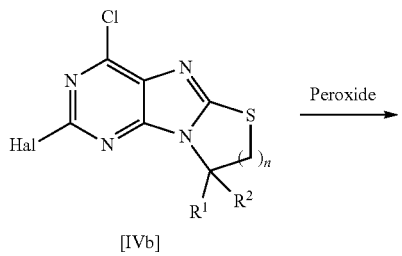

[IVb]

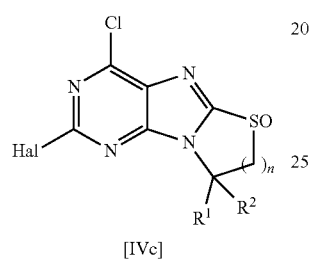

[IVc]

wherein $R_1$, $R^2$, and n are as defined above, and Hal represents halogen.

Intermediate compound [IVc] of compound [I] of the present invention can be manufactured by oxidizing compound [IVb] using peroxide by the reaction indicated by the synthetic pathway described above.

The "peroxide" to be used in the present reaction is not particularly limited as long as S oxide can be formed, and examples thereof include potassium peroxymonosulfate (Oxone (registered trademark)), m-chloroperbenzoic acid (MCPBA), perbenzoic acid, peracetic acid, trifluoroperacetic acid, sodium periodate, hydrogen peroxide, 3,3-dimethyldioxirane, N-(benzenesulfonyl)-3-phenyloxaziridine, magnesium monoperoxyphthalate hexahydrate, tert-butylhydroperoxide, sodium bromate, potassium permanganate, manganese dioxide, selenium dioxide, chromium trioxide, sodium perborate, tetrapropylammonium perruthenate, and the like.

The "solvent" in the present reaction may be an inert solvent in the reaction, and examples thereof include water, ethers (e.g., dioxane, tetrahydrofuran, diethyl ether, 1,2-dimethoxyethane, diethylene glycol dimethyl ether, and ethylene glycol dimethyl ether), halohydrocarbons (e.g., methylene chloride, chloroform, 1,2-dichloroethane, and carbon tetrachloride), aromatic hydrocarbons (e.g., benzene, toluene, and xylene), lower alcohols (e.g., methanol, ethanol, and isopropanol), and polar solvents (e.g., N,N-dimethylformamide (DMF), N-methylpyrrolidone (NMP), dimethyl sulfoxide (DMSO), hexamethylphosphoric triamide, and acetonitrile). These solvents are used alone or as a mixture of two or more of them.

Other reaction conditions (reaction temperature, reaction time, etc.) can be appropriately determined based on a known oxidation reaction.

General synthetic pathway of amine side chain

[Chem.13]

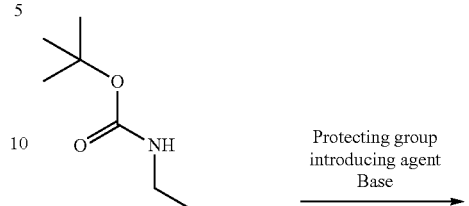

[VI]

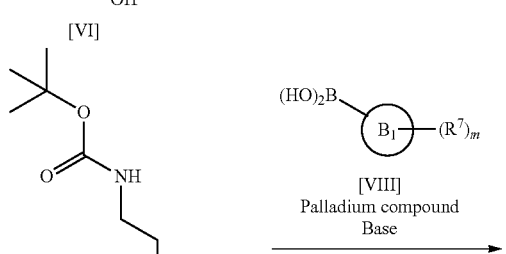

[VII]

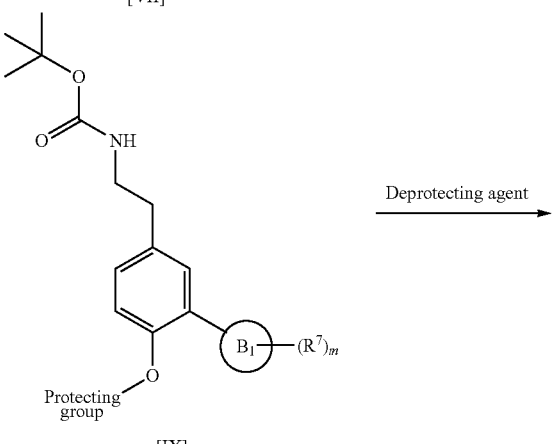

[IX]

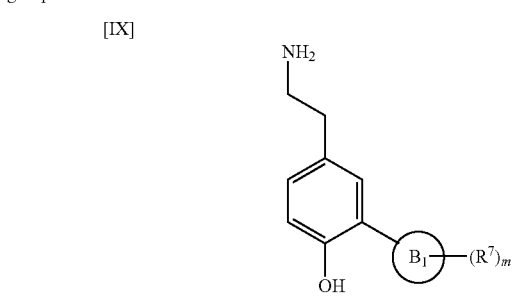

[Va]

wherein R[7], Y, and m are as defined above. Ring B, represents a hydrocarbon ring or a heterocyclic ring which is further optionally bonded to a hydrocarbon ring or a heterocyclic ring of the ring B.

Intermediate compound [Va] of compound [I] of the present invention can be manufactured by the reaction indicated by the synthetic pathway described above. Specifically, hydroxy of tert-butyl N-[2-(3-bromo-4-hydroxyphenyl)ethyl]carbamate is protected using an appropriate protecting group, and compound [VIII] in which the objective substituent is introduced is then subjected to Suzuki cross-coupling reaction in the presence of a palladium compound. Thereafter, the resulting product is de-protected, so that the objective compound [Va] can be synthesized.

Compound [Va] contains an acid addition salt. Examples of the "acid" include an inorganic acid (e.g., hydrochloric acid, hydrobromic acid, nitric acid, sulfuric acid, phosphoric acid, etc.); an organic acid (e.g., methanesulfonic acid, p-toluenesulfonic acid, acetic acid, citric acid, tataric acid, maleic acid, fumaric acid, malic acid, lactic acid, etc.); and the like.

The "palladium compound" to be used in the present reaction is not particularly limited, and examples thereof include tetravalent palladium catalysts such as sodium hexachloropalladium (IV) acid tetrahydrate and potassium hexachloropalladium (IV) acid; divalent palladium catalysts such as [1,1'-bis(diphenylphosphino)ferrocene]palladium(II) dichloride dichloromethane adduct ($Pd(dppf)Cl_2CH_2Cl_2$), (2-dicyclohexylphosphino-2',4',6'-triisopropyl-1,1'-biphenyl)[2-(2'-amino-1,1'-biphenyl)]palladium(II) methanesulfonate (XPhos Pd G3), palladium(II) chloride, palladium (II) bromide, palladium(II) acetate, palladium(II) acetylacetonate, dichlorobis(benzonitrile)palladium(II), dichlorobis(acetonitrile)palladium(II), dichlorobis(triphenylphosphine)palladium(II), dichlorotetraammine palladium(II), dichloro(cycloocta-1,5-diene)palladium(II), and palladium(II) trifluoroacetate; and zerovalent palladium catalysts such as tris(dibenzylideneacetone)dipalladium(0) ($Pd_2(dba)_3$), tris(dibenzylideneacetone)dipalladium(0)-chloroform complex, and tetrakis(triphenylphosphine)palladium(0) ($Pd(PPh_3)_4$). These palladium compounds are used alone or as a mixture of two or more of them.

Examples of the "base" to be used in the presence of a base in the present reaction include an inorganic base, an organic base, and the like. Examples of the "inorganic base" include an alkali metal hydroxide (e.g., sodium hydroxide and potassium hydroxide), an alkaline earth metal hydroxide (e.g., magnesium hydroxide and calcium hydroxide), an alkali metal carbonate (e.g., sodium carbonate and potassium carbonate), an alkaline earth metal carbonate (e.g., magnesium carbonate and calcium carbonate), an alkali metal hydrogen carbonate (e.g., sodium hydrogen carbonate and potassium hydrogen carbonate), an alkali metal phosphate (e.g., sodium phosphate and potassium phosphate), an alkaline earth metal phosphate (e.g., magnesium phosphate and calcium phosphate). Examples of the "organic bases" include trialkylamines (e.g., trimethylamine, triethylamine, and diisopropylethylamine), picoline, 1,5-diazabicyclo[4.3.0]non-5-ene, 1,4-diazabicyclo[2.2.2]octane, and 1,8-diazabicyclo[5.4.0]undec-7-ene.

The "protecting group" to be used in the present reaction is not particularly limited as long as it functions as a protecting group, and examples thereof include alkyl groups (e.g., methyl, ethyl, isopropyl, tert-butyl, trifluoromethyl, hydroxymethyl, 2-hydroxyethyl, and acetylmethyl); alkyl (alkenyl) carbonyl groups (e.g., acetyl, propionyl, butyryl, isobutyryl, pentanoyl, pivaloyl, valeryl, isovaleryl, chloroacetyl, dichloroacetyl, trichloroacetyl, trifluoroacetyl, methoxyacetyl, acryloyl, propioloyl, methacryloyl, crotonoyl, isocrotonoyl, and (E)-2-methyl-2-butenoyl); arylcarbonyl groups (e.g., benzoyl, α-naphthoyl, β-naphthoyl, 2-bromobenzoyl, 4-chlorobenzoyl, 2,4,6-trimethylbenzoyl, 4-toluoyl, 4-anisoyl, 4-nitrobenzoyl, 2-nitrobenzoyl, 2-(methoxycarbonyl)benzoyl, and 4-phenylbenzoyl); tetrahydro(thio)pyranyl(furanyl) groups (e.g., tetrahydropyran-2-yl and 3-bromotetrahydropyran-2-yl); silyl groups (e.g., trimethylsilyl, triethylsilyl, isopropyldimethylsilyl, tert-butyldimethylsilyl, methyldiisopropylsilyl, methyl-di-tert-butylsilyl, triisopropylsilyl, diphenylmethylsilyl, diphenylbutylsilyl, diphenylisopropylsilyl, and phenyldiisopropylsilyl); alkoxymethyl groups (e.g., methoxymethyl, 1,1-dimethyl-1-methoxymethyl, ethoxymethyl, propoxymethyl, isopropoxymethyl, butoxymethyl, tert-butoxymethyl, 2-methoxyethoxymethyl, 2,2,2-trichloroethoxymethyl, and bis(2-chloroethoxy)methyl); aralkyl groups (e.g., benzyl, α-naphthylmethyl, β-naphthylmethyl, diphenylmethyl, triphenylmethyl, α-naphthyldiphenylmethyl, 9-anthrylmethyl, 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, and 4-cyanobenzyl); and the like.

Compound [VIII] used in the above-mentioned reaction includes an optionally substituted arylboronic acid optionally or an optionally substituted heteroarylboronic acid. Examples of the "optionally substituted arylboronic acid" include phenylboronic acid, 2-fluorophenylboronic acid, 3-fluorophenylboronic acid, 4-fluorophenylboronic acid, 2,3-difluorophenylboronic acid, 2,4-difluorophenylboronic acid, 2,5-difluorophenylboronic acid, 2,6-difluorophenylboronic acid, 3,4-difluorophenylboronic acid, 3,5-difluorophenylboronic acid, 3-cyano-2-fluorophenylboronic acid, 5-cyano-2-fluorophenylboronic acid, 3-cyano-5-fluorophenylboronic acid, 2-chlorophenylboronic acid, 3-chlorophenylboronic acid, 4-chlorophenylboronic acid, 2-methylphenylboronic acid, 3-methylphenylboronic acid, 4-methylphenylboronic acid, 2-ethylphenylboronic acid, 3-ethylphenylboronic acid, 4-ethylphenylboronic acid, 3-trifluoromethylphenylboronic acid, 2-hydroxyphenylboronic acid, 3-hydroxyphenylboronic acid, 4-hydroxyphenylboronic acid, 2-methoxyphenylboronic acid, 3-methoxyphenylboronic acid, 4-methoxyphenylboronic acid, 2-cyanophenylboronic acid, 3-cyanophenylboronic acid, 4-cyanophenylboronic acid, 3-methylsulfonylphenylboronic acid, 3-((2-dimethylamino)-2-oxoethyl)phenylboronic acid, 3-(dimethylcarbamoyl)phenylboronic acid, 3-ethoxycarbonylphenylboronic acid, and the like.

Examples of the "optionally substituted heteroarylboronic acid" include 3-pyridylboronic acid, 5-fluoro-3-pyridylboronic acid, 5-methyl-3-pyridylboronic acid, 5-ethyl-3-pyridylboronic acid, 5-cyano-3-pyridylboronic acid, 2-thienylboronic acid, 3-thienylboronic acid, 3-benzothienylboronic acid, and the like.

The "solvent" used in the above-mentioned reaction is not limited as long as it is an inert solvent in the reaction, and examples thereof include water, ethers (e.g., dioxane, tetrahydrofuran, diethyl ether, 1,2-dimethoxyethane, diethylene glycol dimethyl ether, and ethylene glycol dimethyl ether), halohydrocarbons (e.g., methylene chloride, chloroform, 1,2-dichloroethane, and carbon tetrachloride), aromatic hydrocarbons (e.g., benzene, toluene, and xylene), $C_{1-6}$ alcohols (e.g., methanol, ethanol, and isopropanol), and polar solvents (e.g., N,N-dimethylformamide (DMF), N-methylpyrrolidone (NMP), dimethyl sulfoxide (DMSO), hexamethylphosphoric triamide, and acetonitrile). These solvents are used alone or as a mixture of two or more of them.

Other reaction conditions (reaction temperature, reaction time, etc.) can be appropriately determined based on known protection, deprotection, and Suzuki cross-coupling reaction.

After condensation with a tricyclic moiety, the hydrocarbon ring or the heterocyclic ring may be extended using the present reaction.

In each reaction in the above-mentioned equation, the product can be used as a reaction solution or as a crude product thereof in the next reaction. However, the product can be isolated from the reaction mixture in accordance with a conventional method, or easily purified by usual separation means. Examples of the usual separation means include recrystallization, distillation, and chromatography.

The starting material compound, intermediate compound, and objective compound in the above-mentioned steps, and compound [I] of the present invention include geometric isomers, stereoisomers, optical isomers, and tautomers. Various isomers can be separated by a general optical resolution method. They can also be manufactured by an appropriate optically active raw material compound.

Compound [I] of the present invention can be manufactured according to the synthetic methods indicated by the equations described above or methods analogous thereto.

When the specific method of producing the raw material compound used in the manufacturing compound [I] of the present invention is not described, the raw material compound may be a commercially available product, or may be a product manufactured according to a method known per se or a method analogous thereto.

The starting material compound and objective compound in the above-mentioned steps can be used in the form of an appropriate salt. Examples of the salt include those similar to the salts exemplified in the following as the salts of compound [I] of the present invention.

Compound [I] of the present invention includes salt forms thereof including the form of an acid addition salt, or a salt with a base may be formed depending on the kind of the substituent. Examples of the "acid" include an inorganic acid (e.g., hydrochloric acid, hydrobromic acid, nitric acid, sulfuric acid, phosphoric acid, etc.); an organic acid (e.g., methanesulfonic acid, p-toluenesulfonic acid, acetic acid, citric acid, tataric acid, maleic acid, fumaric acid, malic acid, lactic acid, etc.); and the like. Examples of the "base" include an inorganic base (e.g., sodium hydroxide, potassium hydroxide, calcium hydroxide, sodium carbonate, potassium carbonate, sodium hydrogen carbonate, potassium hydrogen carbonate, etc.); an organic base (e.g., methylamine, di-ethylamine, trimethylamine, triethylamine, ethanolamine, diethanolamine, tri-ethanolamine, ethylenediamine, tris(hydroxymethyl)methylamine, dicyclohexylamine, N,N'-dibenzylethylenediamine, guanidine, pyridine, picoline, choline, etc.); ammonium salts; and the like. In addition, a salt with amino acid such as lysine, arginine, aspartic acid, glutamic acid, and the like may be formed.

The present invention also encompasses various hydrates or solvates of compound [I] and a salt thereof, and a crystal polymorphic substance of the same.

Compound [I] of the present invention includes a compound in which one or more atoms are substituted by one or more isotopes. Examples of the isotope include deuterium ($^2H$), tritium ($^3H$), $^{13}C$, $^{15}N$, $^{18}O$. and the like.

Compound [I] of the present invention also includes a pharmaceutically acceptable prodrug. Examples of the substituent that is modified to form a prodrug include reactive functional groups such as —OH, —COOH, amino, and the like. The modifying groups of these functional groups may be appropriately selected from the "substituents" in the present specification.

Compound [I] or a salt thereof of the present invention may be a co-crystal or a co-crystal salt. The co-crystal or co-crystal salt as used herein means a crystalline material composed of two or more unique solids at room temperature, each of which has distinctive physical characteristics (e.g., structure, melting point, heats of fusion, etc.). A co-crystal and a co-crystal salt can be manufactured by applying a known co-crystallization method.

Compound [I] or a salt thereof of the present invention has an aryl hydrocarbon receptor antagonist activity and has a function of promoting production of platelets from platelet progenitor cells.

Compound [I] or a salt thereof of the present invention has hematopoietic stem cell proliferation promoting activity, differentiation promoting activity from ES cells to NK cells, T cell differentiation regulating activity, rheumatoid arthritis exacerbation inhibiting activity, antitumor activity, antivirus activity, anti-inflammatory activity (e.g., atopic dermatitis, etc.), and neuroprotective activity.

The method of producing platelets from platelet progenitor cells using the compound [I] or a salt thereof of the present invention will be described below.

Platelets can be produced by using one or two or more kinds of the compound or a salt thereof of the present invention, bringing megakaryocytes (a kind of platelet progenitor cell), or progenitor cells thereof into contact with it/them. The concentration of the compound or salt of the present invention is not particularly limited, and can be appropriately determined by a person skilled in the art depending on the compound. The concentration thereof is, for example, in the range of 1 nM to 10 µM, preferably 10 nM to 1 µM, and further preferably 100 nM, but it may be out of such range as long as a desired effect is exhibited.

Further, the compound or a salt thereof of the present invention can increase the amount of platelets produced from the megakaryocytes. The compound or salt of the present invention can increase the number of platelets, for example, by 200% or more, preferably 300% or more, further preferably 500% or more, as compared with a control sample, though not limited thereto.

The timing of adding compound [I] or a salt thereof of the present invention is not particularly limited as long as a desired effect is exhibited. For example, compound [I] or salt of the present invention is added to megakaryocytes or progenitor cells thereof. The megakaryocytes may be multinucleated or multinucleated, and the multinucleated megakaryocytes may be in the course of the production of platelets. As described later, in the case of producing immortalized megakaryocytes by forcibly expressing at least one gene selected from the group consisting of a cancer gene, a polycomb gene, and an apoptosis suppressor gene in cells undifferentiated than megakaryocytes and then proceeding with multinucleation of the immortalized megakaryocytes by terminating the forced expression, it is preferable to add the compound or a salt thereof of the present invention to the medium after terminating the forced expression (including at the same time of the termination).

Known cells can be used as the megakaryocytes usable in the present invention, and immortalized megakaryocytes can be prepared using the method disclosed in WO 2016/204256, for example.

The origin of megakaryocytes or progenitor cells thereof is not particularly limited as long as they have production ability of platelets, and examples thereof include pluripotent stem cells, in particular, induced pluripotent stem cells (iPS cells) or embryonic stem cells (ES cells). The derivations of iPS cells and ES cells are not particularly limited, and examples thereof include human-derived cells.

The compound or a salt of the present invention can be used as a platelet production promoting agent, in combination with one or two or more thrombopoietin (TPO) or TPO receptor agonists, one or two or more Rho-associated coiled-coil forming kinase (ROCK) inhibitors, and/or one or two or more disintegrin and metalloprotease (ADAM) inhibitors, and the like. In addition to these combinations, known aryl hydrocarbon receptor antagonists are also combined, so that the compound or salt of the present invention can be used as a platelet production promoting agent.

Examples of the ROCK inhibitor include, but are not limited to, Y27632, Y39983, fasudil hydrochloride, ripasudil, SLX-2119, RKI-1447, Azaindole 1, SR-3677, staurosporine, H1152 dihydrochloride, AR-1 2286, INS-117548, and the like. The concentration of the ROCK inhibitor is not particularly limited, and can be appropriately determined by a person skilled in the art depending on the compound. The concentration thereof is, for example, in the range of 1.0 nM to 1.0 mM, 10 nM to 0.1 mM, 100 nM to 0.1 mM, or 100 nM to 0.01 mM, but it may be out of such range as long as a desired effect is exerted.

Thrombopoietin includes thrombopoietin (TPO) and human recombinant thrombopoietin. Examples of the TPO receptor agonist include, but are not limited to, TA-316 and the like. The concentration of the TPO and human recombinant TPO is not particularly limited, and can be appropriately determined by a person skilled in the art. The concentrations of the TPO and the human recombinant TPO are, for example, in the range of 0.5 ng/mL to 5 µg/mL, preferably 5 to 500 ng/mL, and further preferably 50 ng/mL, but it may be out of such range as long as a desired effect is exhibited. The concentration of the TPO receptor agonist is not particularly limited, and can be appropriately determined by a person skilled in the art depending on the compound. The concentration thereof is, for example, in the range of 0.1 ng/mL to 1 mg/mL, preferably 1 ng/mL to 100 µg/mL, and further preferably 10 ng/mL to 10 µg/mL, but it may be out of such range as long as a desired effect is exhibited.

Examples of the ADAM inhibitor include, but are not limited to, KP-457 and the like. The concentration of the ADAM inhibitor is not particularly limited, and can be appropriately determined by a person skilled in the art depending on the compound. The concentration thereof is, for example, in the range of 1.0 nM to 1.0 mM, preferably 10 nM to 0.1 mM, and further preferably 100 nM to 0.1 mM, but it may be out of such range as long as a desired effect is exhibited.

Examples of known aryl hydrocarbon receptor antagonists include, but are not limited to, SR-1, GNF351, CH-223191, 6,2',4'-trimethoxyflavone (TMF), 3',4'-dimethoxyflavone (DMF), and the like.

The compound or a salt thereof of the present invention can be made into a kit in combination with one or two or more TPO or TPO receptor agonists, one or two or more ROCK inhibitors, and/or one or two or more ADAM inhibitors, and the like. In addition to these combinations, known aryl hydrocarbon receptor antagonists can also be combined to make a kit.

The timing of adding the compounds used in combination is not particularly limited as long as a desired effect is exhibited. The compounds used in combination can be added to a medium before, after, or at the same time when the compound or a salt thereof of the present invention is added to the medium. In the case of producing immortalized megakaryocytes by forcibly expressing at least one gene selected from the group consisting of a cancer gene, a polycomb gene, and an apoptosis suppressor gene in cells undifferentiated than megakaryocytes and then proceeding with multinucleation of immortalized megakaryocytes by terminating the forced expression, it is preferable to add the compounds to the medium after termination (including at the same time of termination) of forced expression.

The amount of time for the above-mentioned forced expression is not particularly limited, and can be appropriately determined by a person skilled in the art. Furthermore, the cells may be subcultured following forced expression, and although there are no particular limitations on the amount of time from the final round of subculturing to the day on which forced expression is terminated, that amount of time may be, for example, 1 day, 2 days or 3 days or more.

When the compound or a salt thereof of the present invention is added to the medium after forced expression has been terminated, although the amount of time from the termination of forced expression to the day of addition of the compound or a salt thereof of the present invention to the medium is not particularly limited, culturing may be started in the presence of the compound or a salt thereof of the present invention within, for example, 1 day, 2 days or 3 days. The period of time for culturing cells in the presence of the compound or a salt thereof of the present invention is also not particularly limited. Usually, functional platelets are gradually released starting on about the third day after adding the compound or a salt thereof of the present invention to the medium, and the number of platelets increases with the number of days of culturing. The period of time for culturing cells in the presence of the compound or a salt thereof of the present invention is, for example, 5 to 10 days, but the duration of culturing may be shortened or lengthened. The compound or a salt thereof of the present invention may be added to the medium in one or more additions during the culturing period.

Cell culturing conditions can be those used during ordinary culturing. For example, the temperature can be a temperature of about 35° C. to about 42° C., preferably about 36° C. to about 40° C., or further preferably about 37° C. to about 39° C., and culturing may be carried out in the presence of 5% $CO_2$ and/or 20% $O_2$. Culturing may be carried out by static culturing or shake culturing. There are no particular limitations on the shaking speed in the case of shake culturing, and a shaking speed of, for example, 10 rpm to 200 rpm, or preferably 30 rpm to 150 rpm can be used.

When megakaryocytes and/or progenitor cells thereof are brought into contact with the compound or a salt thereof of the present invention and then cultured, matured megakaryocytes are obtained, and platelets are produced from the cytoplasm thereof. Here, maturation of megakaryocytes refers to enabling the megakaryocytes to become multinucleated and release platelets.

There are no particular limitations on the medium used when megakaryocytes are cultured, and a known medium or a medium analogous thereto that is suitable for producing platelets from megakaryocytes can be appropriately used. For example, a medium used to culture animal cells can be prepared as a basal medium. Examples of the basal medium include IMDM medium, Medium 199, Eagle's minimum essential medium (EMEM), αMEM, Dulbecco's modified Eagle's medium (DMEM), Ham's F12 medium, RPMI 1640 medium, Fischer's medium, Neurobasal medium (Life Technologies Corporation), and a mixed medium thereof.

The medium may contain serum or plasma, or may be serum-free. In the case of using serum, fetal bovine serum (FBS) or human serum can be used. The medium can contain one or more substances such as albumin, insulin, transferrin, selenium, fatty acids, trace elements, 2-mercaptoethanol, thiolglycerol, monothioglycerol (MTG), lipid, amino acids (such as L-glutamine), ascorbic acid, heparin, non-essential amino acids, vitamins, growth factors, low molecular weight compounds, antibiotics, antioxidants, pyruvic acid, buffers, inorganic salts or cytokines as necessary. Cytokines are proteins that promote hematopoietic differentiation, and examples thereof include VEGF, TPO, TPO-receptor agonist, SCF, insulin-transferrin-selenite (ITS) supplement, ADAM inhibitors, and the like.

Disclosures of all patent literature and non-patent literature cited in the present specification are incorporated in the present specification in their entirety by reference.

EXAMPLES

The present invention is explained in detail in the following by referring to Test Examples, Reference Examples, and Examples, which are not to be construed as limitative, and the invention may be changed within the scope of the present invention.

In the present specification, the following abbreviations may be used.

| Abbreviations | Words |
| --- | --- |
| REX | reference example number |
| EX | example number |
| STR | structural formula (wherein the structure represented as "chiral" indicates absolute configuration.) |
| RProp | Manufacturing method (numbers indicate that the compound was manufactured using the corresponding raw materials in the same way as the reference example compound having that number as a reference example number) |
| Prop | Manufacturing method (numbers indicate that the compound was manufactured using the corresponding raw materials in the same way as the example compound having that number as an example number) |
| Data | property data (NMR1: $^1$H-NMR (in DMSO-$d_6$) δ (ppm); NMR2: $^1$H-NMR (in CDCl$_3$) δ (ppm); MS: mass spectrum) |
| 9-BBN | 9-borabicyclo[3.3.1]nonane |
| AcOEt | ethyl acetate |
| AcOH | acetic acid |
| AcOK | potassium acetate |
| AcONa | sodium acetate |
| BBr$_3$ | boron tribromide |
| n-BuLi | n-butyllithium |
| CDI | 1,1'-carbonyldiimidazole |
| Cs$_2$CO$_3$ | cesium carbonate |
| DBU | 1,8-diazabicyclo[5.4.0]-7-undecene |
| DCC | dicyclohexylcarbodiimide |
| DCE | 1,2-dichloroethane |
| DCM | dichloromethane |
| DEAD | diethylazodicarboxylate |
| DHP | 3,4-dihydro-2H-pyran |
| DIBAL | diisobutylaluminum hydride |
| DIBOC | di-t-butyl dicarbonate |
| DIPEA | diisopropylethylamine |
| DMA | N,N-dimethylacetamide |
| DMAP | 4-(dimethylamino)pyridine |
| DME | dimethoxyethane |
| DMF | N,N-dimethylformamide |
| DMSO | dimethyl sulfoxide |

-continued

| Abbreviations | Words |
| --- | --- |
| DPPA | diphenylphosphoryl azide |
| Et$_2$O | diethyl ether |
| EtOH | ethanol |
| HCl | hydrochloric acid |
| Hexane | n-hexane |
| HOBt | 1-hydroxybenzotriazole |
| IPA | 2-propanol |
| IPE | diisopropyl ether |
| K$_2$CO$_3$ | potassium carbonate |
| K$_3$PO$_4$ | tripotassium phosphate |
| KHCO$_3$ | potassium hydrogen carbonate |
| KOH | potassium hydroxide |
| KOtBu | potassium t-butoxide |
| LAH | lithium aluminum hydride |
| LDA | lithium diisopropylamide |
| LHMDS | lithium hexamethyldisilazide |
| LiOH | lithium hydroxide |
| MCPBA | m-chloroperbenzoic acid |
| MeCN | acetonitrile |
| MEK | 2-butanone |
| MeOH | methanol |
| NaBH$_4$ | sodium borohydride |
| Na$_2$CO$_3$ | sodium carbonate |
| NaH | sodium hydride |
| NaHCO$_3$ | sodium hydrogen carbonate |
| NaOH | sodium hydroxide |
| NaOtBu | sodium t-butoxide |
| NBS | N-bromosuccinimide |
| NCS | N-chlorosuccinimide |
| NMP | N-methylpyrrolidone |
| Pd$_2$(dba)$_3$ | tris(dibenzylideneacetone)dipalladiu(0) |
| Pd(dppf)Cl$_2$•DCM | [1,1'-bis(diphenylphosphino)ferrocene]palladium(II) dichloride dichloromethane adduct |
| Pd(PPh$_3$)$_4$ | tetrakis(triphenylphosphine)palladium(0) |
| Pd/C | palladium-carrying carbon |
| PEG | polyethylene glycol |
| PPTS | pyridinium p-toluenesulfonate |
| TCDI | 1,1'-thiocarbonyldiimidazole |
| TEA | triethylamine |
| TFA | trifluoroacetic acid |
| THF | tetrahydrofuran |
| TPP | triphenylphosphine |
| WSC | 3-ethyl-1-(3-dimethylaminopropyl)carbodiimide |
| ZCl | benzyl chloroformate |
| XPhos Pd G3 | (2-dicyclohexylphosphino-2',4',6'-triisopropyl-1,1'-biphenyl)[2-(2'-amino-1,1'-biphenyl)]palladium(II) methanesulfonate |

In the following Examples, "room temperature" generally means about 10° C. to about 35° C. The ratios indicated for mixed solvents are volume mixing ratios, unless otherwise specified. % means wt %, unless otherwise specified.

$^1$HNMR (proton nuclear magnetic resonance spectrum) was measured by Fourier-transform type NMR (either of Bruker AVANCE 111400 (400 MHz) and Bruker AVANCE III HD (500 MHz)).

Mass spectrum (MS) was measured by LC/MS (ACQUITY UPLC H-Class). As ionization method, ESI method was used. The data indicates actual measured value (found). Generally, molecular ion peaks ([M+H]$^+$, [M−H]$^−$, etc.) are observed. In the case of a salt, a molecular ion peak or fragment ion peak of free form is generally observed.

In silica gel column chromatography, when denoted as basic, aminopropylsilane-bonded silica gel was used.

The absolute configuration of the compound was determined by known X-ray crystal structure analysis method (e.g., "Basic Course for Chemists 12, X-ray Crystal Structure Analysis" written by Shigeru Ohba and Shigenobu Yano, 1st edition, 1999) or estimated from the empirical rule of Shi asymmetric epoxidation (Waldemar Adam, Rainer T. Fell, Chantu R. Saha-Moller and Cong-Gui Zhao: Tetrahedron:

Asymmetry 1998, 9, 397-401; Yuanming Zhu, Yong Tu, Hongwu Yu, Yian Shi: Tetrahedron Lett. 1988, 29, 2437-2440).

Reference Examples

Reference Example 1

Synthesis of 2-amino-6-chloro-9-(1-hydroxy-2-methylpropan-2-yl)-7H-purin-8-one

A solution of 2,5-diamino-4,6-dichloropyrimidine (10.0 g) and 2-amino-2-methyl-1-propanol (11.7 ml) in NMP (10 ml) was stirred overnight at 140° C. The reaction mixture was purified by column chromatography (Hexane/AcOEt/MeOH). To a solution of the product in THF (150 ml) was added CDI (19.9 g) at 0° C., and the mixture was stirred for 1 hour. To the mixture were added 50% MeOH aqueous solution (300 ml) and 5 N NaOH aqueous solution (44.7 ml), and the mixture was stirred for 1 hour. The reaction mixture was concentrated, 5 N HCl aqueous solution was added to the residue, and the solid precipitate was collected by filtration to obtain the object compound (10.9 g).

Reference Example 2

Synthesis of 2-amino-6-chloro-9-(3-hydroxypropyl)-7H-purin-8-one

A solution of 2,5-diamino-4,6-dichloropyrimidine (1.00 g), 3-amino-1-propanol (0.86 ml), and DIPEA (2.44 ml) in NMP (10 ml) was stirred overnight at 150° C. The reaction mixture was purified by column chromatography (Hexane/AcOEt/MeOH). To a solution of the product in THF (15 ml) was added CDI (2.72 g), and the mixture was stirred for 30 minutes. To the mixture were added 50% MeOH aqueous solution (5 ml) and 5 N NaOH aqueous solution (4.47 ml), and the mixture was stirred overnight. The reaction mixture was concentrated, 5 N HCl aqueous solution was added to the residue, and the solid precipitate was collected by filtration to obtain the object compound (1.11 g).

Reference Example 3

Synthesis of 2-amino-6-chloro-9-(4-hydroxy-2-methylbutan-2-yl)-7H-purin-8-one

A solution of 2,5-diamino-4,6-dichloropyrimidine (1.20 g), 3-amino-3-methyl-1-butanol hydrochloride (1.03 g), and DIPEA (2.93 ml) in NMP (6 ml) was stirred overnight at 150° C. The reaction mixture was purified by column chromatography (Hexane/AcOEt/MeOH). To a solution of the product in THF (15 ml) was added CDI (2.17 g), and the mixture was stirred for 30 minutes. To the mixture were added 50% MeOH aqueous solution (20 ml) and 5 N NaOH aqueous solution (5.36 ml), and the mixture was stirred overnight. The reaction mixture was concentrated, 5 N HCl aqueous solution was added to the residue, and the mixture was extracted with AcOEt. The organic layer was washed with saturated saline, dried with anhydrous sodium sulfate and filtered, and the filtrate was concentrated. The residue was purified by column chromatography (AcOEt/Hexane) to obtain the object compound (345 mg).

Reference Example 7

Synthesis of 4-chloro-2-iodo-9,9-dimethyl-7,8-dihydropurino[8,9-b][1,3]oxazine

To a solution of 6-chloro-9-(4-hydroxy-2-methylbutan-2-yl)-2-iodo-7H-purin-8-one (180 mg) in THF (5 ml) were added di-tert-butyl azodicarboxylate (163 mg) and triphenylphosphine (185 mg), and the mixture was stirred for 2 hours under nitrogen atmosphere at 0° C. The reaction mixture was concentrated, and the residue was purified by column chromatography (Hexane/AcOEt) to obtain the object compound (163 mg).

Reference Example 8

Synthesis of 4-chloro-2-iodo-8,8-dimethyl-7H-purino[8,9-b][1,3]oxazole

To a suspension solution of 2-amino-6-chloro-9-(1-hydroxy-2-methylpropan-2-yl)-7H-purin-8-one (10.90 g) and triphenylphosphine (13.31 g) in THF (200 ml) was added dropwise diisopropyl azodicarboxylate (40% toluene solution) (26.7 ml) at 0° C. under nitrogen atmosphere, and the mixture was stirred for 2 hours. The reaction mixture was concentrated, and the residue was purified by column chromatography (Hexane/AcOEt). To a solution of the product in THF (200 ml) were added copper(I) iodide (8.06 g), diiodomethane (10.24 ml), and tert-butyl nitrite (7.55 ml), and the mixture was stirred at 60° C. for 5 hours. The reaction mixture was filtered through Celite, and the filtrate was concentrated. The residue was purified by column chromatography (Hexane/AcOEt) to obtain the object compound (9.29 g).

Reference Example 10

Synthesis of (8R)-4-chloro-8-methyl-7,8-dihydropurino[8,9-b][1,3]thiazole-2-amine A solution of 2,5-diamino-4,6-dichloropyrimidine (2.00 g) and (2R)-2-amino-1-hydroxypropane (1.91 ml) in NMP (3 ml) was stirred overnight at 140° C. The reaction mixture was purified by column chromatography (Hexane/AcOEt/MeOH). To a solution of the product in THF (30 ml) was gradually added TCDI (5.58 g) at 0° C., and the mixture was stirred for 30 minutes, and then stirred overnight at room temperature. The reaction mixture was concentrated, water was added thereto at 0° C., and the solid precipitate was collected by filtration to obtain the object compound (1.53 g).

Reference Example 13

Synthesis of 4-chloro-8,9-dihydro-7H-purino[8,9-b][1,3]thiazine-2-amine 2,5-diamino-4,6-dichloropyrimidine (1.00 g) and 3-amino-1-propanol (0.940 ml) were mixed at 140° C. for 4 hours. The reaction mixture was purified by column chromatography (Hexane/AcOEt/MeOH). To a solution of the product in THF (10 ml) was gradually added TCDI (2.49 g) at 0° C., and the mixture was stirred for 30 minutes. The stirred mixture was brought to room temperature, DMF (15 ml) was added thereto, and the mixture was stirred overnight. Thereto was added $K_2CO_3$ (0.93 g), and the mixture was stirred for 1 hour. The reaction mixture was concentrated, thereto was added water, and the mixture was extracted with AcOEt. The organic layer was washed with saturated saline, dried with anhydrous sodium sulfate and filtered, and the filtrate was concentrated. The obtained solid was dispersed and washed with IPE to obtain the object compound (646 mg).

Reference Example 14

Synthesis of 4-chloro-2-iodo-8,8-dimethyl-7H-purino[8,9-b][1,3]thiazole

A suspension of 4-chloro-8,8-dimethyl-7H-purino[8,9-b][1,3]thiazole-2-amine (1.93 g), copper(I) iodide (1.44 g), diiodomethane (2.44 ml), and tert-butyl nitrite (1.35 ml) in THF (30 ml) was stirred overnight at 60° C. The reaction mixture was filtered through Celite, and the filtrate was concentrated. The residue was purified by column chromatography (Hexane/AcOEt) to obtain the object compound (1.63 g).

Reference Example 19

Synthesis of 4-chloro-2-iodo-7,8,9,10-tetrahydro-purino[8,9-b][1,3]thiazepine

A solution of 2,5-diamino-4,6-dichloropyrimidine (1.00 g) and 4-amino-1-butanol (1.13 ml) in NMP (1.5 ml) was stirred overnight at 140° C. The reaction mixture was purified by column chromatography (Hexane/AcOEt/MeOH). To a solution of the product in THF (15 ml) was gradually added TCDI (2.49 g) at 0° C., and the mixture was stirred for 30 minutes, and then stirred overnight at room temperature. The reaction mixture was concentrated, thereto was added water, and the solid precipitate was collected by filtration. This was suspended in THF/MeOH (3/1) (20 ml), thereto was added dropwise 5 N NaOH aqueous solution (2.24 ml) at 0° C., and the mixture was stirred overnight at room temperature. The reaction mixture was concentrated, and 5 N HCl aqueous solution was added to the residue at 0° C. The solid precipitate was collected by filtration. To a solution of the product in THF (20 ml) was added dropwise triphenylphosphine (1.47 g) and diisopropyl azodicarboxylate (40% toluene solution) (2.94 ml) at 0° C., and the mixture was stirred for 4 hours. The reaction mixture was concentrated, water was added to the residue, and the mixture was extracted with DCM. The organic layer was washed with saturated saline, dried with anhydrous sodium sulfate and filtered, and the filtrate was concentrated. The residue was purified by column chromatography (Hexane/AcOEt). To a solution of the product in THF (20 ml) were added copper(I) iodide (1.06 g), diiodomethane (1.35 ml), and tert-butyl nitrite (1.00 ml), and the mixture was stirred at 60° C. for 3 hours. The reaction mixture was filtered through Celite, and the filtrate was concentrated. The residue was purified by column chromatography (Hexane/AcOEt) to obtain the object compound (196 mg).

Reference Example 20

Synthesis of 4-chloro-2-iodo-8,8-dimethyl-7H-purino[8,9-b][1,3]thiazole 6-oxide

To a solution of 4-chloro-2-iodo-8,8-dimethyl-7H-purino[8,9-b][1,3]thiazole (100 mg) in THF/water (2/1) (3 ml) was added Oxone (registered trademark) (184 mg), and the mixture was stirred for 2 hours. The mixture was stirred at 60° C. for 1 hour, to the reaction mixture was then added water, and the mixture was extracted with AcOEt. The organic layer was washed with saturated saline, dried with anhydrous sodium sulfate and filtered, and the filtrate was concentrated. The residue was purified by column chromatography (Hexane/AcOEt) to obtain the object compound (70 mg).

Reference Example 21

Synthesis of (8R)-4-chloro-2-iodo-8-methyl-7,8-dihydropurino[8,9-b][1,3]thiazole 6-oxide To a solution of (8R)-4-chloro-2-iodo-8-methyl-7,8-dihydropurino[8,9-b][1,3]thiazole (200 mg) in DCM (4 ml) was added MCPBA (180 mg), and the mixture was stirred overnight. To the reaction mixture was added saturated $NaHCO_3$ aqueous solution, and the mixture was extracted with AcOEt. The organic layer was washed with saturated saline, dried with anhydrous sodium sulfate and filtered, and the filtrate was concentrated to obtain the object compound (150 mg).

Reference Example 22

Synthesis of tert-butyl N-[2-[3-bromo-4-(methoxymethoxy)phenyl]ethyl]carbamate

To a solution of tert-butyl N-[2-(3-bromo-4-hydroxyphenyl)ethyl]carbamate (9.40 g) in DCM (150 ml) were added DIPEA (7.79 ml) and chloromethyl methyl ether (2.94 ml) at 0° C., and the mixture was stirred at room temperature for 3 days. The reaction mixture was concentrated, and the residue was then purified by column chromatography (Hexane/AcOEt) to obtain the object compound (10.9 g).

Reference Example 23

Synthesis of tert-butyl N-[2-[4-(methoxymethoxy)-3-phenylphenyl]ethyl]carbamate

Under nitrogen atmosphere, a mixture of tert-butyl N-[2-[3-bromo-4-(methoxymethoxy)phenyl]ethyl]carbamate (500 mg), phenylboronic acid (254 mg), $K_3PO_4$ (589 mg), Pd(dppf)Cl$_2$DCM (113 mg), and DME/water (4/1) (5 ml) was heated under reflux for 5 hours. The reaction mixture was concentrated, and the residue was then purified by column chromatography (Hexane/AcOEt) to obtain the object compound (455 mg).

Reference Example 27

Synthesis of tert-butyl N-[2-[3-(5-cyano-2-fluorophenyl)-4-(methoxymethoxy)phenyl]ethyl]carbamate Under nitrogen atmosphere, a mixture of tert-butyl N-[2-[3-bromo-4-(methoxymethoxy)phenyl]ethyl]carbamate (50 mg), 5-cyano-2-fluorophenylboronic acid (29.8 mg), XPhos Pd G3 (11.75 mg), $K_3PO_4$ (58.9 mg), and THF/water (4/1) (2 ml) was heated under reflux overnight. The reaction mixture was concentrated, and the residue was then purified by column chromatography (Hexane/AcOEt) to obtain the object compound (37 mg).

Reference Example 37

Synthesis of 2-(2-fluorophenyl)-4-[2-[(2-iodo-8,8-dimethyl-7H-purino[8,9-b][1,3]oxazol-4-yl)amino]ethyl]phenol A solution of 4-chloro-2-iodo-8,8-dimethyl-7H-purino[8,9-b][1,3]oxazole (150 mg), 4-(2-aminoethyl)-2-(2-fluorophenyl)phenol hydrochloride (172 mg), DIPEA (0.22 ml) in DMSO (1 ml) was stirred overnight at 80° C. The reaction mixture was purified by column chromatography (Hexane/AcOEt) to obtain the object compound (135 mg).

Reference Example 46

Synthesis of 2-(5-fluoropyridin-3-yl)-4-[2-[(2-iodo-8,8-dimethyl-7H-purino[8,9-b][1,3]thiazol-4-yl)amino]ethyl]phenol A suspension of 4-chloro-2-iodo-8,8-dimethyl-7H-purino[8,9-b][1,3]thiazole (100 mg), 4-(2-aminoethyl)-2-(5-fluoropyridin-3-yl)phenol dihydrochloride (108 mg), and DIPEA (0.14 ml) in IPA (2 ml) was stirred overnight at 80° C. Water was added to the mixture, and the solid precipitate was collected by filtration to obtain the object compound (154 mg).

Reference Example 60

Synthesis of N-[2-(1H-indol-3-yl)ethyl]-2-iodo-8,9-dihydro-7H-purino[8,9-b][1,3]oxazine-4-amine A solution of 4-chloro-2-iodo-8,9-dihydro-7H-purino[8,9-b][1,3]oxazine (244 mg), tryptamine hydrochloride (214 mg), and DIPEA (0.25 ml) in IPA/DMSO (5/1) (6 ml) was stirred overnight at 70° C. To the reaction mixture was added water, and the mixture was extracted with AcOEt. The organic layer was washed with saturated saline, dried with anhydrous sodium sulfate and filtered, and the filtrate was concentrated. The residue was purified by column chromatography (Hexane/AcOEt) to obtain the object compound (133 mg).

Reference Example 78

Synthesis of Tert-Butyl 3-[1-[[(2-methylpropan-2-yl)oxycarbonylamino]methyl]cyclopropyl]indole-1-carboxylate To a suspension of LAH (0.14 g) in THF (10 ml) was added dropwise concentrated sulfuric acid (0.10 ml) under nitrogen atmosphere at −5° C., and the mixture was stirred for 30 minutes. Thereafter, a solution of tert-butyl 3-(1-cyanocyclopropyl)indole-1-carboxylate (0.67 g) in THF (5 ml) was added dropwise thereto, and the mixture was stirred at room temperature for 2 hours. Thereto were added 50% THF aqueous solution and 5 N NaOH aqueous solution, and the mixture was filtered through Celite. The filtrate was dried with anhydrous sodium sulfate and filtered, and the filtrate was concentrated. To the residual solution of EtOH (10 ml) was added DIBOC (0.66 ml), and the mixture was stirred at room temperature for 1 hour. The reaction mixture was concentrated, and the residue was then purified by column chromatography (Hexane/AcOEt) to obtain the object compound (0.30 g).

Reference Example 79

Synthesis of [1-(1H-indol-3-yl)cyclopropyl]methanamine Hydrochloride

To a solution of tert-butyl 3-[1-[[(2-methylpropan-2-yl)oxycarbonylamino]methyl]cyclopropyl]indole-1-carboxylate (0.30 g) in AcOEt/EtOH (1/1) (10 ml) was added 4 N HCl/AcOEt (6 ml), and the mixture was stirred at 50° C. for 6 hours. The reaction mixture was concentrated to obtain the object compound (0.18 g).

Reference Example 80

Synthesis of tert-butyl N-[2-[3-(2-fluorophenyl)-4-(methoxymethoxy)phenyl]ethyl]carbamate A mixture of tert-butyl N-[2-[3-bromo-4-(methoxymethoxy)phenyl]ethyl]carbamate (1.00 g), 2-fluorophenylboronic acid (621 mg), Pd(PPh$_3$)$_4$ (160 mg), Na$_2$CO$_3$ (883 mg), and 1,4-dioxane/water (4/1) (10 ml) was stirred at 90° C. for 6 hours under nitrogen atmosphere. To the reaction mixture was added water, and the mixture was extracted with AcOEt. The organic layer was concentrated, and the residue was then purified by column chromatography (Hexane/AcOEt) to obtain the object compound (1.14 g).

Reference Example 81

Synthesis of Tert-Butyl N-[2-[3-(2-chlorophenyl)-4-(methoxymethoxy)phenyl]ethyl]carbamate A mixture of tert-butyl N-[2-[3-bromo-4-(methoxymethoxy)phenyl]ethyl]carbamate (500 mg), 2-chlorophenylboronic acid (239 mg), Pd(dppf)Cl$_2$-DCM (56.7 mg), K$_3$PO$_4$ (589 mg), and 1,4-dioxane/water (4/1) (5 ml) was stirred at 90° C. for 2 hours under nitrogen atmosphere. Thereto was added 2-chlorophenylboronic acid (195 mg), and the mixture was stirred at 90° C. for 4 hours. The reaction mixture was concentrated, and the residue was then purified by column chromatography (Hexane/AcOEt). A mixture of the product, 2-chlorophenylboronic acid (434 mg), Pd(dppf)Cl$_2$-DCM (56.7 mg), K$_3$PO$_4$ (589 mg), and 1,4-dioxane/water (4/1) (5 ml) was stirred overnight at 90° C. under nitrogen atmosphere. The reaction mixture was concentrated, and the residue was then purified by column chromatography (Hexane/AcOEt) to obtain the object compound (487 mg).

Reference Example 90

Synthesis of Tert-Butyl N-[2-[3-(3-cyanophenyl)-4-(methoxymethoxy)phenyl]ethyl]carbamate A mixture of tert-butyl N-[2-[3-bromo-4-(methoxymethoxy)phenyl]ethyl]carbamate (350 mg), 3-cyanophenylboronic acid (186 mg), K$_3$PO$_4$ (412 mg), Pd(dppf)Cl$_2$-DCM (39.7 mg), and 1,4-dioxane/water (4/1) (5 ml) was stirred at 90° C. for 4 hours under nitrogen atmosphere. The reaction mixture was concentrated, and the residue was then purified by column chromatography (Hexane/AcOEt) to obtain the object compound (366 mg).

Reference Example 100

Synthesis of Tert-Butyl N-[2-[3-(5-fluoropyridin-3-yl)-4-(methoxymethoxy)phenyl]ethyl]carbamate A mixture of tert-butyl N-[2-[3-bromo-4-(methoxymethoxy)phenyl]ethyl]carbamate (600 mg), 5-fluoropyridine-3-boronic acid (352 mg), Pd(PPh$_3$)$_4$ (96 mg), Na$_2$CO$_3$ (530 mg), and 1,4-dioxane/water (4/1) (10 ml) was stirred at 90° C. for 2 hours under nitrogen atmosphere. The reaction mixture was concentrated, and the residue was then purified by column chromatography (Hexane/AcOEt) to obtain the object compound (643 mg).

Reference Example 106

Synthesis of 4-(2-aminoethyl)-2-(2-fluorophenyl)phenol hydrochloride

To a solution of tert-butyl N-[2-[3-(2-fluorophenyl)-4-(methoxymethoxy)phenyl]ethyl]carbamate (1.14 g) in EtOH (5 ml) was added 4 N HCU/AcOEt (5 ml), and the mixture was stirred overnight at room temperature. The reaction mixture was concentrated, and the residue was then dispersed and washed with Hexane/AcOEt to obtain the object compound (686 mg).

Reference Example 109

Synthesis of 4-(2-aminoethyl)-2-(3-chlorophenyl)phenol Hydrochloride

To a solution of tert-butyl N-[2-[3-(3-chlorophenyl)-4-(methoxymethoxy)phenyl]ethyl]carbamate (534 mg) in EtOH (3 ml) was added 4 N HCUAcOEt (3 ml), and the mixture was stirred overnight at room temperature. The reaction mixture was concentrated to obtain the object compound (408 mg).

Reference Example 117

Synthesis of 3-[5-(2-aminoethyl)-2-hydroxyphenyl]benzonitrile Hydrochloride

To a solution of tert-butyl N-[2-[3-(3-cyanophenyl)-4-(methoxymethoxy)phenyl]ethyl]carbamate (364 mg) in EtOH (2 ml) was added 4 N HCUAcOEt (2 ml), and the mixture was stirred at room temperature for 7 hours. The reaction mixture was concentrated to obtain the object compound (242 mg).

Reference Example 127

Synthesis of 4-(2-aminoethyl)-2-(5-fluoropyridin-3-yl)phenol Dihydrochloride To a solution of tert-butyl N-[2-[3-(5-fluoropyridin-3-yl)-4-(methoxymethoxy)phenyl]ethyl]carbamate (641 mg) in EtOH (4 ml) was added 4 N HCUAcOEt (4 ml), and the mixture was stirred at room temperature for 3 hours. The reaction mixture was concentrated, and the residue was then dispersed and washed with Hexane/AcOEt to obtain the object compound (477 mg).

Reference Example 132

Synthesis of 3-[5-(2-aminoethyl)-2-hydroxyphenyl]-N,N-dimethylbenzamide Hydrochloride To a solution of ethyl 3-[2-(methoxymethoxy)-5-[2-[(2-methylpropan-2-yl)oxycarbonylamino]ethyl]phenyl]benzoate (758 mg) in EtOH (7 ml) was added 5 N NaOH aqueous solution (0.642 ml), and the mixture was stirred at room temperature for 1 hour. Thereto was added 5 N NaOH aqueous solution (0.642 ml), and the mixture was stirred at room temperature for 4 hours. To the reaction mixture were added 5 N HCl aqueous solution (1.3 ml) and water, and the mixture was extracted with AcOEt. The organic layer was concentrated, the residue was then dissolved in DMF (7 ml), thereto were added WSC hydrochloride (462 mg), HOBt (326 mg), and 50% dimethylamine aqueous solution (0.488 ml), and the mixture was stirred at room temperature for 3 days. To the reaction mixture was added water, and the mixture was extracted with AcOEt. The organic layer was washed with water and saturated saline, and then concentrated. The residue was dissolved in EtOH (4 ml), thereto was added 4 N HCUAcOEt (4 ml), and the mixture was stirred at room temperature for 5 hours. The reaction mixture was concentrated to obtain the object compound (589 mg).

Reference Example 142

Synthesis of 3-[2-hydroxy-5-[2-[(2-iodo-8,8-dimethyl-7H-purino[8,9-b][1,3]oxazol-4-yl)amino]ethyl]phenyl]benzonitrile A suspension of 4-chloro-2-iodo-8,8-dimethyl-7H-purino[8,9-b][1,3]oxazole (150 mg), 3-[5-(2-aminoethyl)-2-hydroxyphenyl]benzonitrile hydrochloride (153 mg), and DIPEA (0.22 ml) in IPA (2 ml) was stirred overnight at 80° C. Water was added to the mixture, and the solid precipitate was collected by filtration to obtain the object compound (211 mg).

Reference Example 146

Synthesis of 4-[2-[(2-iodo-8,8-dimethyl-7H-purino[8,9-b][1,3]oxazol-4-yl)amino]ethyl]-2-thiophen-2-ylphenol Mixed were 4-chloro-2-iodo-8,8-dimethyl-7H-purino[8,9-b][1,3]oxazole (200 mg), 4-(2-aminoethyl)-2-thiophen-2-ylphenol hydrochloride (207 mg), and IPA (2 ml), thereto was added DIPEA (0.298 ml), and the mixture was stirred overnight at 80° C. The reaction mixture was allowed to cool to room temperature, and the solid precipitate was then collected by filtration to obtain the object compound (223 mg).

Reference Example 152

Synthesis of 2-(5-fluoropyridin-3-yl)-4-[2-[(2-iodo-8,8-dimethyl-7H-purino[8,9-b][1,3]oxazol-4-yl)amino]ethyl]phenol A solution of 4-chloro-2-iodo-8,8-dimethyl-7H-purino[8,9-b][1,3]oxazole (200 mg), 4-(2-aminoethyl)-2-(5-fluoropyridin-3-yl)phenol dihydrochloride (226 mg), and DIPEA (0.30 ml) in IPA (3 ml) was stirred overnight at 80° C. The reaction mixture was concentrated, and the residue was then purified by column chromatography (Hexane/AcOEt) to obtain the object compound (212 mg).

Reference Example 159

Synthesis of N-[2-(3-bromo-4-phenylmethoxyphenyl)ethyl]-2-(5-fluoropyridin-3-yl)-8,8-dimethyl-7H-purino[8,9-b][1,3]oxazole-4-amine To a solution of 2-bromo-4-[2-[[2-(5-fluoropyridin-3-yl)-8,8-dimethyl-7H-purino[8,9-b][1,3]oxazol-4-yl]amino]ethyl]phenol (107 mg) in DMF (1 ml) were added $K_2CO_3$ (38.5 mg) and benzylbromide (0.028 ml), and the mixture was stirred at room temperature for 2 hours. Water and IPE were added to the reaction mixture, and the solid precipitate was collected by filtration to obtain the object compound (111 mg).

Reference Example 160

Synthesis of 2-(5-fluoropyridin-3-yl)-N-[2-[3-(3-methoxyphenyl)-4-phenylmethoxyphenyl]ethyl]-8,8-dimethyl-7H-purino[8,9-b][1,3]oxazole-4-amine A mixture of N-[2-(3-bromo-4-phenylmethoxyphenyl)ethyl]-2-(5-fluoropyridin-3-yl)-8,8-dimethyl-7H-purino[8,9-b][1,3]oxazole-4-amine (109 mg), 3-methoxyphenylboronic acid (30.9 mg), Pd(dppf)Cl$_2$DCM (7.6 mg), $K_3PO_4$ (79.0 mg), and 1,4-dioxane/water (4/1) (1 ml) was stirred at 90° C. for 3 hours under nitrogen atmosphere. Thereto was added 3-methoxyphenylboronic acid (25.3 mg), and the mixture was stirred overnight at 90° C. The reaction mixture was purified by column chromatography (Hexane/AcOEt) to obtain the object compound (104 mg).

The compounds of Reference Examples 4 to 6, 9, 11, 12, 15 to 18, 24 to 26, 28 to 36, 38 to 45, 47 to 59, 61 to 77, 82 to 89, 91 to 99, 101 to 105, 107, 108, 110 to 116, 118 to 126, 128 to 131, 133 to 141, 143 to 145, 147 to 151, 153 to 158, and 161 to 167 were manufactured in the same manner as in Reference Examples 1 to 3, 7, 8, 10, 13, 14, 19 to 23, 27, 37, 46, 60, 78 to 81, 90, 100, 106, 109, 117, 127, 132, 142, 146, 152, 159, and 160. Structural formulae and physicochemical data of the compounds of Reference Examples 1 to 167 are shown in Tables 1-1 to 1-29.

TABLE 1-1

| REX | STR | | RProp | Data |
|---|---|---|---|---|
| 1 | (structure) | 1 | NMR1 (500 MHz); 11.16 (1H, s), 6.48 (2H, s), 4.87 (1H, t, J = 6.6 Hz), 3.79 (2H, d, J = 6.6 Hz), 1.60 (6H, s). | |
| 2 | (structure) | 2 | NMR1 (500 MHz); 11.23 (1H, s), 6.61 (2H, s), 4.55 (1H, t, J = 5.1 Hz), 3.77-3.70 (2H, m), 3.44 (2H, t, J = 5.4 Hz), 1.84-1.74 (2H, m). | |
| 3 | (structure) | 3 | NMR1 (500 MHz); 11.09 (1H, s), 6.42 (2H, s), 4.31 (1H, t, J = 4.9 Hz), 3.39 (2H, td, J = 7.0, 4.2 Hz), 2.20 (2H, t, J = 7.1 Hz), 1.72 (6H, s). | |

TABLE 1-1-continued

| REX | STR | | RProp Data |
|---|---|---|---|
| 4 | (structure) | 14 | NMR1 (500 MHz); 12.15 (1H, s), 4.53 (1H, t, J = 5.0 Hz), 3.84-3.79 (2H, m), 3.48-3.41 (2H, m), 1.86-1.77 (2H, m). |
| 5 | (structure) | 14 | NMR1 (500 MHz); 12.04 (1H, s), 4.29 (1H, t, J = 4.8 Hz), 3.42 (2H, td, J = 6.7, 4.8 Hz), 2.17 (2H, t, J = 6.7 Hz), 1.73 (6H, s). |
| 6 | (structure) | 7 | NMR2 (500 MHz); 4.66-4.60 (2H, m), 4.27-4.21 (2H, m), 2.40-2.30 (2H, m). |
| 7 | (structure) | 7 | NMR2 (500 MHz); 4.62-4.55 (2H, m), 2.25-2.19 (2H, m), 1.83 (6H, s). |
| 8 | (structure) | 8 | NMR1 (500 MHz); 5.02 (2H, s), 1.68 (6H, s). |
| 9 | (structure) | 10 | NMR1 (500 MHz); 6.79 (2H, s), 3.84 (2H, s), 1.67 (6H, s). |

TABLE 1-2
| REX | STR | RProp | Data |
|---|---|---|---|
| 10 | 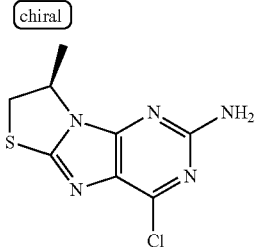 | 10 | NMR1 (500 MHz); 6.81 (2H, s), 4.81-4.71 (1H, m), 4.16 (1H, dd, J = 11.2, 7.2 Hz), 3.64 (1H, dd, J = 11.3, 5.2 Hz), 1.53 (3H, d, J = 6.3 Hz). |
| 11 | 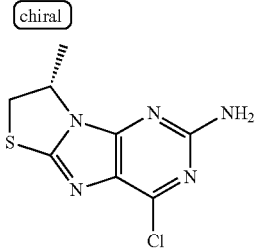 | 10 | NMR1 (500 MHz); 6.82 (2H, s), 4.81-4.71 (1H, m), 4.16 (1H, dd, J = 11.2, 7.2 Hz), 3.64 (1H, dd, J = 11.3, 5.2 Hz), 1.53 (3H, d, J = 6.4 Hz). |
| 12 | 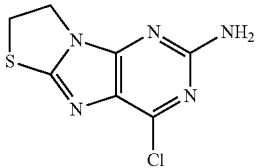 | 10 | NMR1 (500 MHz); 6.82 (2H, s), 4.25-4.19 (2H, m), 4.04-3.98 (2H, m). |
| 13 | 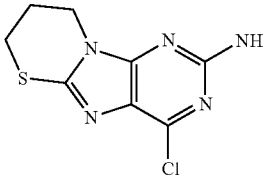 | 13 | NMR1 (500 MHz); 6.80 (2H, s), 4.08-4.03 (2H, m), 3.30-3.26 (2H, m), 2.52-2.48 (2H, m). |
| 14 | 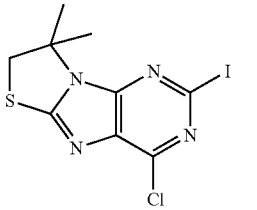 | 14 | NMR1 (500 MHz); 3.95 (2H, s), 1.72 6H, s). |
| 15 | 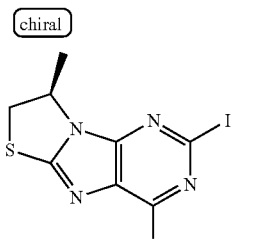 | 14 | NMR1 (500 MHz); 5.01-4.90 (1H, m), 4.23 (1H, dd, J = 11.3, 7.3 Hz), 3.75 (1H, dd, J = 11.3, 6.1 Hz), 1.60 (3H, d, J = 6.4 Hz). |

TABLE 1-2-continued
| REX | STR | RProp | Data |
|---|---|---|---|
| 16 | 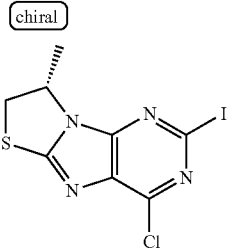 | 14 | NMR1 (500 MHz); 5.01-4.90 (1H, m), 4.23 (1H, dd, J = 11.3, 7.3 Hz), 3.75 (1H, dd, J = 11.3, 6.2 Hz), 1.60 (3H, d, J = 6.3 Hz). |
| 17 | 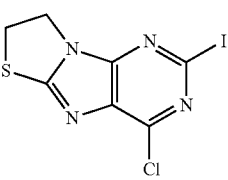 | 14 | NMR1 (500 MHz); 4.42 (2H, dd, J = 8.1, 6.7 Hz), 4.10 (2H, dd, J = 8.1, 6.7 Hz). |
| 18 | 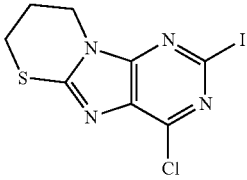 | 14 | NMR1 (500 MHz); 4.26-4.20 (m, 2H), 3.39-3.33 (m, 2H), 2.35-2.27 (m, 2H). |
TABLE 1-3
| REX | STR | RProp | Data |
|---|---|---|---|
| 19 | 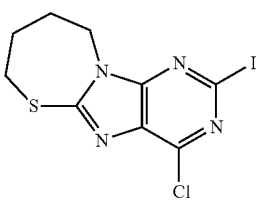 | 19 | NMR1 (500 MHz); 4.36-4.30 (2H, m), 3.13-3.07 (2H, m), 2.18-2.10 (2H, m), 1.94-1.86 (2H, m). |
| 20 | 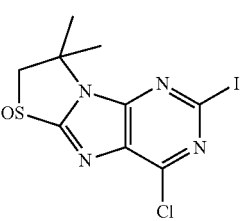 | 20 | NMR1 (500 MHz); 3.98 (1H, d, J = 14.3 Hz), 3.91 (1H, d, J = 14.3 Hz), 1.84 (6H, s). |
| 21 | 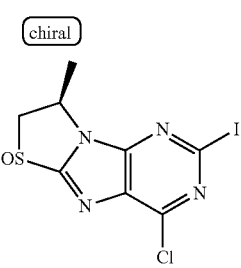 | 21 | NMR1 (500 MHz); 5.41-5.10 (1H, m), 4.34-4.03 (1H, m), 3.83-3.66 (1H, m), 1.79-1.73 (3H, m). MS m/z 369.13, 371.05 (M + 1). |

TABLE 1-3-continued

| REX | STR | RProp | Data |
|---|---|---|---|
| 22 | | 22 | NMR2 (500 MHz); 7.38 (1H, d, J = 1.9 Hz), 7.11-7.03 (2H, m), 5.22 (2H, s), 4.53 (1H, s), 3.52 (3H, s), 3.37-3.30 (2H, m), 2.72 (2H, t, J = 7.0 Hz), 1.44 (9H, s). |
| 23 | | 23 | NMR2 (500 MHz); 7.54-7.48 (2H, m), 7.44-7.37 (2H, m), 7.36-7.29 (1H, m), 7.18-7.13 (2H, m), 7.13-7.08 (1H, m), 5.09 (2H, s), 4.56 (1H, s), 3.41-3.34 (5H, m), 2.78 (2H, t, J = 7.0 Hz), 1.43 (9H, s). |
| 24 | | 23 | NMR2 (500 MHz); 7.40-7.32 (1H, m), 7.30-7.23 (2H, m), 7.18-7.11 (3H, m), 7.06-6.99 (1H, m), 5.11 (2H, s), 4.56 (1H, s), 3.40-3.34 (5H, m), 2.78 (2H, t, J = 7.1 Hz), 1.43 (9H, s). |

TABLE 1-3-continued

| REX | STR | RProp | Data |
|---|---|---|---|
| 25 | | 23 | NMR2 (500 MHz); 7.52-7.44 (2H, m), 7.17-7.05 (5H, m), 5.09 (2H, s), 4.56 (1H, s), 3.41-3.33 (5H, m), 2.78 (2H, t, J = 7.0 Hz), 1.43 (9H, s). |

TABLE 1-4

| REX | STR | RProp | Data |
|---|---|---|---|
| 26 | | 27 | NMR2 (400 MHz); 7.36-7.26 (1H, m), 7.22-7.15 (2H, m), 7.10 (1H, s), 7.01-6.90 (2H, m), 5.11 (2H, s), 4.58 (1H, s), 3.42-3.33 (5H, m), 2.78 (2H, t, J = 7.0 Hz), 1.43 (9H, s). |
| 27 | | 27 | NMR2 (500 MHz); 7.72-7.62 (2H, m), 7.27-7.16 (3H, m), 7.07 (1H, s), 5.12 (2H, s), 4.59 (1H, s), 3.42-3.33 (5H, m), 2.79 (2H, t, J = 7.0 Hz), 1.43 (9H, s). |

TABLE 1-4-continued
| REX | STR | RProp | Data |
|---|---|---|---|
| 28 | | 27 | NMR2 (500 MHz); 7.65-7.56 (2H, m), 7.30 (1H, t, J = 7.7 Hz), 7.25-7.17 (2H, m), 7.07 (1H, s), 5.13 (2H, s), 4.58 (1H, s), 3.42-3.33 (5H, m), 2.79 (2H, t, J = 7.1 Hz), 1.43 (9H, s). |
| 29 | | 27 | NMR2 (400 MHz); 7.63 (1H, t, J = 1.5 Hz), 7.52-7.48 (1H, m), 7.34-7.30 (1H, m), 7.19 (2H, s), 7.11 (1H, s), 5.15 (2H, s), 4.57 (1H, s), 3.41 (3H, s), 3.40-3.30 (2H, m), 2.79 (2H, t, J = 7.1 Hz), 1.43 (9H, s). |
| 30 | | 106 | NMR1 (500 MHz); 9.50 (1H, s), 7.90 (3H, s), 7.58-7.52 (2H, m), 7.43-7.36 (2H, m), 7.33-7.26 (1H, m), 7.14 (1H, d, J = 2.3 Hz), 7.04 (1H, dd, J = 8.2, 2.3 Hz), 6.91 (1H, d, J = 8.2 Hz), 3.07-2.97 (2H, m), 2.84-2.77 (2H, m). |
| 31 | | 106 | NMR1 (500 MHz); 9.59 (1H, s), 7.98 (3H, s), 7.63-7.55 (2H, m), 7.26-7.18 (2H, m), 7.14 (1H, d, J = 2.3 Hz), 7.04 (1H, dd, J = 8.2, 2.3 Hz), 6.93 (1H, d, J = 8.2 Hz), 3.06-2.96 (2H, m), 2.85-2.78 (2H, m). |
TABLE 1-5
| REX | STR | RProp | Data |
|---|---|---|---|
| 32 |  | 109 | NMR1 (500 MHz); 9.68 (1H, s), 7.99 (3H, s), 7.48-7.40 (1H, m), 7.17-7.11 (3H, m), 7.08-7.04 (1H, m), 6.94 (1H, d, J = 8.3 Hz), 3.03-2.96 (2H, m), 2.85-2.79 (2H, m). |

TABLE 1-5-continued

| REX | STR | RProp | Data |
|---|---|---|---|
| 33 | | 109 | NMR1 (400 MHz); 9.79 (1H, s), 8.00-7.88 (5H, m), 7.53-7.47 (1H, m), 7.19-7.10 (2H, m), 6.94 (1H, d, J = 8.2 Hz), 3.08-2.95 (2H, m), 2.86-2.77 (2H, m). |
| 34 | | 109 | NMR1 (400 MHz); 9.81 (1H, s), 7.99-7.88 (4H, m), 7.77 (1H, td, J = 7.6, 1.8 Hz), 7.46 (1H, t, J = 7.8 Hz), 7.20-7.10 (2H, m), 6.95 (1H, d, J = 8.3 Hz), 3.06-2.95 (2H, m), 2.86-2.78 (2H, m). |
| 35 | | 109 | NMR1 (400 MHz); 10.01 (1H, s), 7.99 (3H, s), 7.92 (1H, t, J = 1.4 Hz), 7.87-7.75 (2H, m), 7.30 (1H, d, J = 2.2 Hz), 7.13 (1H, dd, J = 8.3, 2.3 Hz), 6.98 (1H, d, J = 8.3 Hz), 3.04 (2H, brs), 2.87-2.79 (2H, m). |
| 36 | | 46 | NMR2 (500 MHz); 7.50-7.44 (4H, m), 7.41-7.35 (1H, m), 7.14-7.07 (2H, m), 6.91 (1H, d, J = 8.1 Hz), 5.41 (1H, s), 5.37 (1H, s), 4.72 (2H, s), 3.83 (2H, s), 2.88 (2H, t, J = 7.0 Hz), 1.72 (6H, s). |
| 37 | | 37 | NMR1 (500 MHz); 9.35 (1H, s), 7.66 (1H, s), 7.40-7.28 (2H, m), 7.24-7.17 (2H, m), 7.08 (1H, dd, J = 8.2, 2.3 Hz), 7.02 (1H, s), 6.84 (1H, d, J = 8.2 Hz), 4.85 (2H, s), 3.89-3.47 (2H, m), 2.83-2.75 (2H, m), 1.60 (6H, s). |
| 38 | | 37 | NMR1 (500 MHz); 9.49 (1H, s), 7.66 (1H, s), 7.46-7.38 (1H, m), 7.38-7.30 (2H, m), 7.16 (1H, s), 7.11 (1H, td, J = 8.6, 2.7 Hz), 7.05 (1H, dd, J = 8.2, 2.2 Hz), 6.86 (1H, d, J = 8.2 Hz), 4.85 (2H, s), 3.90-3.50 (2H, m), 2.79 (2H, t, J = 7.3 Hz), 1.60 (6H, s). |

TABLE 1-6

| REX | STR | RProp Data |
|---|---|---|
| 39 | | 37 NMR1 (500 MHz); 9.39 (1H, s), 7.66 (1H, s), 7.59-7.52 (2H, m), 7.25-7.16 (2H, m), 7.12 (1H, s), 7.02 (1H, dd, J = 8.2, 2.2 Hz), 6.85 (1H, d, J = 8.2 Hz), 4.85 (2H, s), 3.90-3.49 (2H, m), 2.78 (2H, t, J = 7.4 Hz), 1.60 (6H, s). |
| 40 | | 37 NMR2 (500 MHz); 7.39-7.30 (2H, m), 7.21 (1H, td, J = 7.6, 1.3 Hz), 7.18-7.10 (2H, m), 7.08 (1H, d, J = 2.2 Hz), 6.89 (1H, d, J = 8.2 Hz), 6.07 (1H, s), 5.69 (1H, s), 3.81 (2H, brs), 3.65 (2H, s), 2.88 (2H, t, J = 6.9 Hz), 1.77 (6H, s). |
| 41 | | 37 NMR2 (500 MHz); 7.43-7.35 (1H, m), 7.23 (1H, d, J = 7.7 Hz), 7.13 (1H, d, J = 9.8 Hz), 7.12-7.00 (3H, m), 6.85 (1H, d, J = 8.1 Hz), 6.17 (1H, s), 5.87 (1H, s), 3.91-3.73 (2H, m), 3.67 (2H, s), 2.88 (2H, t, J = 6.8 Hz), 1.78 (6H, s). |
| 42 | chiral | 37 NMR2 (500 MHz); 7.37-7.28 (2H, m), 7.19 (1H, td, J = 7.6, 1.2 Hz), 7.16-7.06 (3H, m), 6.88 (1H, d, J = 8.2 Hz), 6.61 (1H, s), 5.78 (1H, s), 4.86-4.76 (1H, m), 4.05 (1H, dd, J = 11.2, 7.3 Hz), 3.80 (2H, s), 3.47 (1H, dd, J = 11.2, 4.6 Hz), 2.87 (2H, t, J = 6.9 Hz), 1.63 (3H, d, J = 6.3 Hz). |
| 43 | chiral | 37 NMR2 (500 MHz); 7.97 (1H, s), 7.34-7.24 (1H, m), 7.18 (1H, d, J = 7.8 Hz), 7.05 (1H, d, J = 9.3 Hz), 7.03-6.92 (3H, m), 6.77 (1H, d, J = 8.0 Hz), 6.04 (1H, s), 4.86-4.76 (1H, m), 4.05 (1H, dd, J = 11.2, 7.3 Hz), 3.75 (2H, s), 3.48 (1H, dd, J = 11.2, 4.7 Hz), 2.83 (2H, t, J = 6.5 Hz), 1.63 (3H, d, J = 6.4 Hz). |

TABLE 1-6-continued
| REX | STR | RProp | Data |
|---|---|---|---|
| 44 | 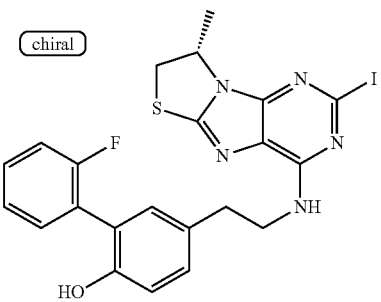 | 37 | NMR2 (500 MHz); 7.35-7.27 (2H, m), 7.18 (1H, td, J = 7.5, 1.3 Hz), 7.14-7.04 (3H, m), 6.96-6.77 (2H, m), 5.84 (1H, s), 4.85-4.75 (1H, m), 4.05 (1H, dd, J = 11.1, 7.3 Hz), 3.79 (2H, s), 3.47 (1H, dd, J = 11.2, 4.6 Hz), 2.86 (2H, t, J = 6.8 Hz), 1.62 (3H, d, J = 6.4 Hz). |
TABLE 1-7
| REX | STR | RProp | Data |
|---|---|---|---|
| 45 | 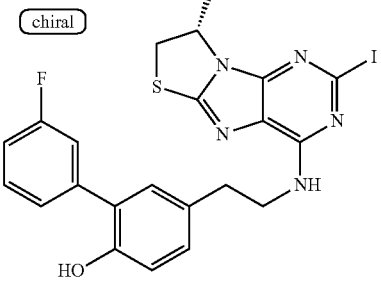 | 37 | NMR2 (500 MHz); 7.75 (1H, s), 7.35-7.27 (1H, m), 7.18 (1H, d, J = 7.6 Hz), 7.09-6.93 (4H, m), 6.78 (1H, d, J = 8.0 Hz), 5.99 (1H, s), 4.86-4.76 (1H, m), 4.06 (1H, dd, J = 11.1, 7.3 Hz), 3.76 (2H, s), 3.48 (1H, dd, J = 11.2, 4.7 Hz), 2.84 (2H, t, J = 6.6 Hz), 1.63 (3H, d, J = 6.4 Hz). |
| 46 | 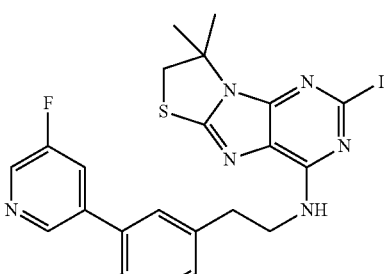 | 46 | NMR1 (500 MHz); 9.77 (1H, s), 8.59 (1H, d, J = 1.9 Hz), 8.49 (1H, d, J = 2.8 Hz), 7.96-7.90 (1H, m), 7.83 (1H, dt, J = 10.4, 2.3 Hz), 7.23 (1H, s), 7.11 (1H, dd, J = 8.2, 2.2 Hz), 6.90 (1H, d, J = 8.2 Hz), 3.84 (2H, s), 3.58 (2H, s), 2.82 (2H, t, J = 7.2 Hz), 1.65 (6H, s). |
| 47 | 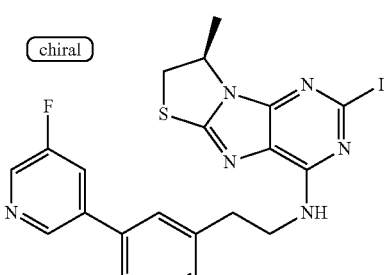 | 46 | NMR1 (500 MHz); 9.77 (1H, s), 8.62-8.59 (1H, m), 8.49 (1H, d, J = 2.8 Hz), 7.94 (1H, s), 7.86-7.79 (1H, m), 7.24 (1H, s), 7.11 (1H, dd, J = 8.2, 2.2 Hz), 6.90 (1H, dd, J = 8.2, 2.8 Hz), 4.84-4.75 (1H, m), 4.14 (1H, dd, J = 11.3, 7.2 Hz), 3.64 (1H, dd, J = 11.2, 5.4 Hz), 3.59 (2H, s), 2.82 (2H, t, J = 7.2 Hz), 1.51 (3H, d, J = 6.3 Hz). |

TABLE 1-7-continued

| REX | STR | RProp | Data |
|---|---|---|---|
| 48 | | 46 | NMR1 (500 MHz); 9.50 (1H, s), 7.66 (1H, s), 7.47-7.38 (1H, m), 7.16-7.08 (3H, m), 7.06-7.02 (1H, m), 6.88 (1H, d, J = 8.3 Hz), 4.85 (2H, s), 3.53 (2H, s), 2.78 (2H, t, J = 7.5 Hz), 1.60 (6H, s). |
| 49 | | 46 | NMR1 (500 MHz); 9.60 (1H, s), 7.95-7.81 (2H, m), 7.67 (1H, s), 7.48 (1H, t, J = 9.1 Hz), 7.17-7.09 (2H, m), 6.87 (1H, d, J = 8.2 Hz), 4.85 (2H, s), 3.56 (2H, s), 2.80 (2H, t, J = 7.4 Hz), 1.61 (6H, s). |
| 50 | | 46 | NMR1 (500 MHz); 9.62 (1H, s), 7.92-7.86 (1H, m), 7.75-7.68 (1H, m), 7.66 (1H, s), 7.44 (1H, t, J = 7.8 Hz), 7.15 (1H, dd, J = 8.3, 2.3 Hz), 7.09 (1H, s), 6.88 (1H, d, J = 8.2 Hz), 4.85 (2H, s), 3.56 (2H, s), 2.80 (2H, t, J = 7.4 Hz), 1.60 (6H, s). |

TABLE 1-8

| REX | STR | RProp | Data |
|---|---|---|---|
| 51 | | 46 | NMR1 (500 MHz); 9.65 (1H, s), 7.85 (1H, s), 7.78-7.72 (2H, m), 7.67 (1H, s), 7.27 (1H, s), 7.11 (1H, dd, J = 8.3, 2.2 Hz), 6.89 (1H, d, J = 8.3 Hz), 4.84 (2H, s), 3.96-3.50 (2H, m), 2.80 (2H, t, J = 7.2 Hz), 1.60 (6H, s). |

TABLE 1-8-continued

| REX | STR | RProp | Data |
|-----|-----|-------|------|
| 52 | | 37 | NMR2 (500 MHz); 7.40-7.32 (2H, m), 7.23 (1H, t, J = 7.5 Hz), 7.19-7.08 (3H, m), 6.92 (1H, d, J = 8.2 Hz), 6.16 (1H, s), 5.61 (1H, s), 3.90-3.76 (2H, m), 3.67 (1H, d, J = 14.1 Hz), 3.59 (1H, d, J = 14.1 Hz), 2.91 (2H, t, J = 7.0 Hz), 1.95 (3H, s), 1.90 (3H, s). |
| 53 | | 37 | NMR2 (500 MHz); 7.44-7.36 (1H, m), 7.27-7.22 (1H, m), 7.21-6.98 (4H, m), 6.88 (1H, d, J = 8.1 Hz), 6.18 (1H, s), 5.88 (1H, s), 3.89-3.77 (2H, m), 3.68 (1H, d, J = 14.1 Hz), 3.60 (1H, d, J = 14.1 Hz), 2.97-2.85 (2H, m), 1.96 (3H, s), 1.90 (3H, s). |
| 54 | | 46 | NMR1 (500 MHz); 9.03 (1H, s), 7.62 (1H, s), 6.94 (1H, d, J = 2.2 Hz), 6.84 (1H, dd, J = 8.0, 2.2 Hz), 6.67 (1H, d, J = 8.1 Hz), 4.85 (2H, s), 3.59-3.41 (2H, m), 2.73-2.66 (2H, m), 2.08 (3H, s), 1.61 (6H, s). |
| 55 | | 37 | MS m/z 493.42, 493.10 (M + 1). |

TABLE 1-8-continued
| REX | STR | RProp | Data |
|---|---|---|---|
| 56 | | 37 | NMR1 (500 MHz); 9.18 (1H, s), 7.62 (1H, s), 7.06-7.00 (2H, m), 6.70-6.64 (2H, m), 4.85 (2H, s), 3.87-3.43 (2H, m), 2.76-2.69 (2H, m), 1.61 (6H, s). |
TABLE 1-9
| REX | STR | RProp | Data |
|---|---|---|---|
| 57 | | 37 | NMR1 (500 MHz); 10.80 (1H, s), 7.83-7.70 (2H, m), 7.36-7.30 (1H, m), 7.17 (1H, d, J = 2.3 Hz), 7.10-7.03 (1H, m), 6.99 (1H, t, J = 7.5 Hz), 4.86 (2H, s), 3.61 (2H, s), 2.98-2.91 (2H, m), 1.62 (6H, s). |
| 58 | | 37 | NMR1 (500 MHz); 10.97 (1H, s), 7.64 (1H, s), 7.39 (1H, s), 7.33-7.26 (2H, m), 6.99 (1H, dd, J = 8.3, 1.7 Hz), 6.37-6.32 (1H, m), 4.85 (2H, s), 3.94-3.46 (2H, m), 2.93-2.87 (2H, m), 1.61 (6H, s). |
| 59 | | 37 | NMR2 (500 MHz); 7.84 (1H, s), 7.64-7.58 (1H, m), 7.30-7.22 (1H, m), 7.15-7.05 (2H, m), 5.62 (1H, s), 4.70 (2H, s), 3.79 (2H, s), 3.01 (2H, t, J = 7.2 Hz), 2.38 (3H, s), 1.72 (6H, s). |
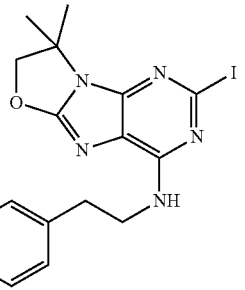

TABLE 1-9-continued
| REX | STR | RProp | Data |
|---|---|---|---|
| 60 | 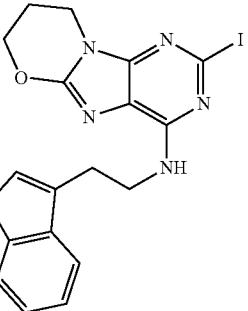 | 60 | NMR2 (500 MHz); 8.21 (1H, s), 7.73-7.68 (1H, m), 7.34 (1H, dt, J = 8.1, 1.0 Hz), 7.22-7.15 (1H, m), 7.15-7.09 (1H, m), 7.01 (1H, d, J = 2.3 Hz), 5.63 (1H, s), 4.50-4.44 (2H, m), 4.12-4.05 (2H, m), 3.93 (2H, s), 3.11-3.04 (2H, m), 2.28-2.20 (2H, m). |
| 61 | 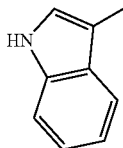 | 60 | NMR2 (500 MHz); 8.08 (1H, s), 7.71 (1H, d, J = 7.8 Hz), 7.35 (1H, dt, J = 8.1, 0.9 Hz), 7.23-7.16 (1H, m), 7.16-7.10 (1H, m), 7.04 (1H, d, J = 2.4 Hz), 5.45 (1H, s), 4.46-4.40 (2H, m), 3.92 (2H, s), 3.12-3.04 (2H, m), 2.15-2.09 (2H, m), 1.76 (6H, s). |
| 62 | 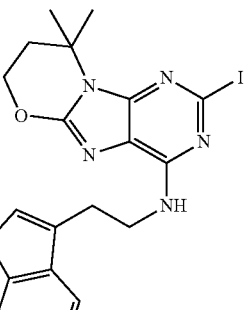 | 60 | NMR2 (500 MHz); 7.80 (1H, s), 7.01 (2H, d, J = 8.0 Hz), 6.68 (2H, d, J = 8.0 Hz), 5.69 (1H, s), 4.48-4.42 (2H, m), 3.80 (2H, s), 2.84 (2H, t, J = 6.4 Hz), 2.17-2.10 (2H, m), 1.78 (6H, s). |
TABLE 1-10
| REX | STR | RProp | Data |
|---|---|---|---|
| 63 | 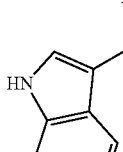 | 37 | NMR1 (500 MHz); 10.80 (1H, s), 8.01 (1H, s), 7.80-7.75 (1H, m), 7.33 (1H, dt, J = 8.1, 0.9 Hz), 7.17 (1H, d, J = 2.3 Hz), 7.10-7.04 (1H, m), 7.00 (1H, t, J = 7.3 Hz), 3.85 (2H, s), 3.62 (2H, s), 2.96 (2H, t, J = 7.8 Hz), 1.67 (6H, s). |

TABLE 1-10-continued
| REX | STR | RProp | Data |
|---|---|---|---|
| 64 | 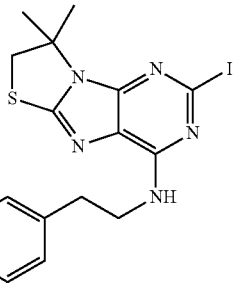 | 60 | NMR1 (500 MHz); 9.17 (1H, s), 7.89 (1H, t, J = 5.8 Hz), 7.06-7.00 (2H, m), 6.70-6.64 (2H, m), 3.84 (2H, s), 3.50 (2H, s), 2.77-2.70 (2H, m), 1.65 (6H, s). |
| 65 | 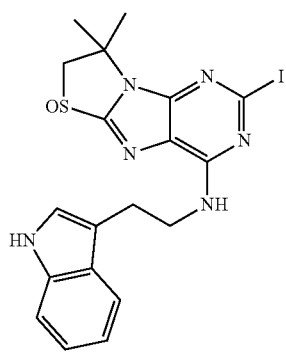 | 60 | MS m/z 507.25 (M + 1). |
| 66 | 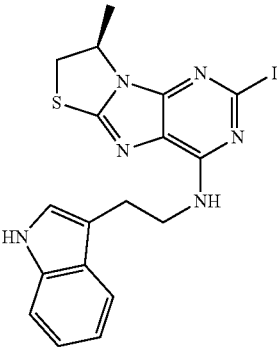 | 37 | NMR2 (500 MHz); 8.07 (1H, s), 7.70 (1H, d, J = 7.9 Hz), 7.35 (1H, dt, J = 8.1, 1.0 Hz), 7.24-7.16 (1H, m), 7.16-7.10 (1H, m), 7.01 (1H, d, J = 2.3 Hz), 5.81 (1H, s), 4.82-4.73 (1H, m), 4.02 (1H, dd, J = 11.1, 7.3 Hz), 3.92 (2H, s), 3.45 (1H, dd, J = 11.1, 4.6 Hz), 3.11-3.05 (2H, m), 1.62 (3H, d, J = 6.3 Hz). |
| 67 | 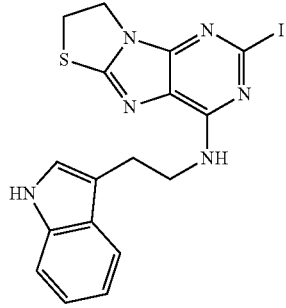 | 37 | NMR2 (500 MHz); 8.37 (1H, s), 7.70 (1H, d, J = 7.9 Hz), 7.35 (1H, dd, J = 8.1, 1.1 Hz), 7.22-7.16 (1H, m), 7.16-7.09 (1H, m), 7.02 (1H, d, J = 2.3 Hz), 5.95 (1H, s), 4.26 (2H, t, J = 7.3 Hz), 3.99-3.81 (4H, m), 3.09 (2H, t, J = 6.9 Hz). |

TABLE 1-10-continued

| REX | STR | RProp | Data |
|---|---|---|---|
| 68 | (chiral structure) | 37 | NMR2 (500 MHz); 8.10 (1H, s), 7.69 (1H, d, J = 7.9 Hz), 7.34 (1H, dt, J = 8.1, 0.9 Hz), 7.23-7.16 (1H, m), 7.16-7.10 (1H, m), 7.00 (1H, d, J = 2.3 Hz), 5.87 (1H, s), 4.81-4.72 (1H, m), 4.01 (1H, dd, J = 11.2, 7.3 Hz), 3.91 (2H, s), 3.44 (1H, dd, J = 11.2, 4.6 Hz), 3.11-3.04 (2H, m), 1.61 (3H, d, J = 6.4 Hz). |

TABLE 1-11

| REX | STR | RProp | Data |
|---|---|---|---|
| 69 | (structure) | 37 | NMR2 (400 MHz); 8.07 (1H, s), 7.74-7.67 (1H, m), 7.35 (1H, dt, J = 8.1, 1.0 Hz), 7.24-7.15 (1H, m), 7.18-7.09 (1H, m), 7.01 (1H, d, J = 2.3 Hz), 5.78 (1H, s), 4.21-4.14 (2H, m), 3.93 (2H, s), 3.23-3.16 (2H, m), 3.12-3.04 (2H, m), 2.40-2.30 (2H, m). |
| 70 | (structure) | 37 | NMR2 (500 MHz); 8.06 (1H, s), 7.71 (1H, dd, J = 7.9, 1.2 Hz), 7.36 (1H, dt, J = 8.1, 0.9 Hz), 7.24-7.17 (1H, m), 7.17-7.11 (1H, m), 7.06 (1H, d, J = 2.3 Hz), 5.89 (1H, s), 4.37-4.31 (2H, m), 3.92 (2H, s), 3.10 (2H, t, J = 6.9 Hz), 2.89-2.83 (2H, m), 2.26-2.18 (2H, m), 1.89-1.79 (2H, m). |
| 71 | (structure) | 46 | NMR1 (400 MHz); 9.35 (1H, s), 7.92 (1H, s), 7.41-7.15 (4H, m), 7.08 (1H, dd, J = 8.3, 2.2 Hz), 7.07-6.94 (1H, m), 6.84 (1H, dd, J = 8.2, 1.1 Hz), 4.27 (2H, t, J = 7.2 Hz), 4.01 (2H, t, J = 7.2 Hz), 3.83-3.49 (2H, m), 2.80 (2H, t, J = 7.4 Hz). |

TABLE 1-11-continued

| REX | STR | RProp | Data |
|---|---|---|---|
| 72 | | 46 | NMR1 (400 MHz); 9.36 (1H, s), 8.26 (1H, s), 7.41-7.26 (2H, m), 7.26-7.15 (2H, m), 7.14-6.93 (2H, m), 6.84 (1H, dd, J = 8.2, 1.4 Hz), 4.23-4.17 (2H, m), 4.08-3.53 (2H, m), 3.01-2.89 (2H, m), 2.81 (2H, t, J = 7.4 Hz), 2.13-2.09 (2H, m), 1.81-1.77 (2H, m). |
| 73 | | 37 | NMR1 (500 MHz); 9.95 (1H, s), 7.66 (1H, s), 7.05 (1H, s), 7.00 (1H, dd, J = 8.0, 2.0 Hz), 6.75 (1H, d, J = 8.0 Hz), 4.85 (2H, s), 3.91-3.46 (2H, m), 2.83 (2H, t, J = 7.4 Hz), 2.79-2.73 (2H, m), 2.45-2.39 (2H, m), 1.61 (6H, s). |
| 74 | | 37 | NMR2 (500 MHz); 7.24-7.14 (2H, m), 7.01-6.96 (2H, m), 5.37 (1H, s), 4.73 (2H, s), 3.82 (2H, s), 2.95-2.85 (2H, m), 1.73 (6H, s). |

TABLE 1-12

| REX | STR | RProp | Data |
|---|---|---|---|
| 75 | | 37 | NMR2 (500 MHz); 8.03 (1H, s), 7.78 (1H, dt, J = 8.0, 1.0 Hz), 7.34 (1H, dt, J = 8.1, 1.0 Hz), 7.23-7.16 (1H, m), 7.16-7.09 (1H, m), 7.06 (1H, d, J = 2.5 Hz), 5.41 (1H, s), 4.67 (2H, s), 3.77 (2H, s), 1.68 (6H, s), 0.99-0.91 (2H, m), 0.94-0.81 (2H, m). |

TABLE 1-12-continued

| REX | STR | RProp | Data |
|---|---|---|---|
| 76 | | 37 | NMR2 (500 MHz); 7.13 (1H, t, J = 7.8 Hz), 7.05 (1H, s), 6.76 (1H, dt, J = 7.6, 1.2 Hz), 6.72 (1H, t, J = 2.0 Hz), 6.70-6.65 (1H, m), 5.58 (1H, s), 4.74 (2H, s), 3.82 (2H, s), 2.87 (2H, t, J = 6.7 Hz), 1.73 (6H, s). |
| 77 | | 37 | NMR2 (500 MHz); 8.11 (1H, s), 7.63 (1H, d, J = 2.0 Hz), 7.26 (1H, d, J = 8.5 Hz), 7.13 (1H, dd, J = 8.6, 2.0 Hz), 7.07 (1H, d, J = 2.4 Hz), 5.50 (1H, s), 4.71 (2H, s), 3.88 (2H, s), 3.03 (2H, t, J = 6.9 Hz), 1.72 (6H, s). |
| 78 | | 78 | NMR2 (400 MHz); 8.12 (1H, s), 7.68 (1H, d, J = 7.7 Hz), 7.44 (1H, s), 7.35-7.29 (1H, m), 7.28-7.22 (1H, m), 4.57 (1H, s), 3.34 (2H, d, J = 5.8 Hz), 1.67 (9H, s), 1.39 (9H, s), 0.92-0.80 (4H, m). |
| 79 | | 79 | NMR1 (500 MHz); 11.05 (1H, s), 7.85 (3H, s), 7.65 (1H, d, J = 7.7 Hz), 7.38 (1H, d, J = 8.0 Hz), 7.25 (1H, d, J = 2.4 Hz), 7.10 (1H, t, J = 7.5 Hz), 7.02 (1H, t, J = 7.4 Hz), 3.02-2.95 (2H, m), 1.01-0.95 (2H, m), 0.87-0.79 (2H, m). |

TABLE 1-12-continued
| REX | STR | | RProp Data |
|---|---|---|---|
| 80 |  | 80 | NMR2 (500 MHz); 7.37-7.28 (2H, m), 7.23-7.07 (5H, m), 5.10 (2H, s), 4.57 (1H, s), 3.45-3.31 (5H, m), 2.78 (2H, t, J = 7.0 Hz), 1.43 (9H, s). |
TABLE 1-13
| REX | STR | | RProp Data |
|---|---|---|---|
| 81 | | 81 | NMR2 (500 MHz); 7.49-7.42 (1H, m), 7.32-7.26 (3H, m), 7.17 (2H, d, J = 1.3 Hz), 7.03 (1H, s), 5.07 (2H, s), 4.57 (1H, s), 3.42-3.31 (5H, m), 2.78 (2H, t, J = 6.8 Hz), 1.43 (9H, s). |
| 82 | | 23 | NMR2 (500 MHz); 7.51 (1H, t, J = 1.9 Hz), 7.40 (1H, dt, J = 7.5, 1.6 Hz), 7.37-7.27 (2H, m), 7.18-7.10 (3H, m), 5.11 (2H, s), 4.56 (1H, s), 3.43-3.31 (5H, m), 2.78 (2H, t, J = 6.7 Hz), 1.43 (9H, s). |

TABLE 1-13-continued

| REX | STR | RProp | Data |
|---|---|---|---|
| 83 | | 23 | NMR2 (500 MHz); 7.48-7.43 (2H, m), 7.40-7.35 (2H, m), 7.17-7.09 (3H, m), 5.10 (2H, s), 4.56 (1H, s), 3.45-3.30 (5H, m), 2.78 (2H, t, J = 7.1 Hz), 1.43 (9H, s). |
| 84 | | 81 | NMR2 (500 MHz); 7.21-7.15 (2H, m), 7.13-6.95 (4H, m), 5.12 (2H, s), 4.56 (1H, s), 3.41-3.34 (5H, m), 2.78 (2H, t, J = 7.0 Hz), 1.43 (9H, s). |
| 85 | | 81 | NMR2 (500 MHz); 7.20-7.06 (6H, m), 5.12 (2H, s), 4.57 (1H, s), 3.42-3.35 (5H, m), 2.78 (2H, t, J = 7.0 Hz), 1.43 (9H, s). |

TABLE 1-14
| REX | STR | RProp | Data |
|-----|-----|-------|------|
| 86 | 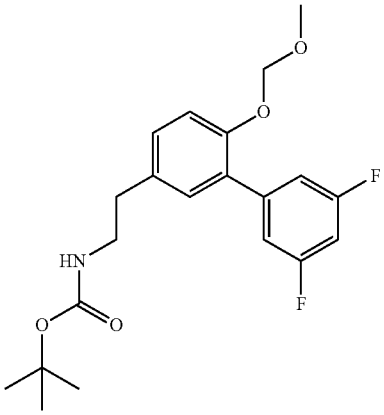 | 23 | NMR2 (500 MHz); 7.19-7.10 (3H, m), 7.10-7.02 (2H, m), 6.82-6.73 (1H, m), 5.13 (2H, s), 4.56 (1H, s), 3.43-3.35 (5H, m), 2.78 (2H, t, J = 7.0 Hz), 1.43 (9H, s). |
| 87 | 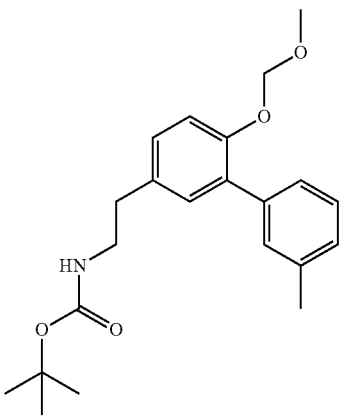 | 23 | NMR2 (500 MHz); 7.35-7.24 (3H, m), 7.18-7.07 (4H, m), 5.08 (2H, s), 4.56 (1H, s), 3.45-3.28 (5H, m), 2.78 (2H, t, J = 7.0 Hz), 2.40 (3H, s), 1.43 (9H, s). |
| 88 | 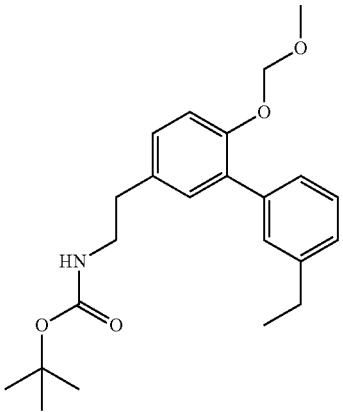 | 23 | NMR2 (500 MHz); 7.36-7.29 (3H, m), 7.21-7.06 (4H, m), 5.08 (2H, s), 4.56 (1H, s), 3.46-3.30 (5H, m), 2.78 (2H, t, J = 7.1 Hz), 2.70 (2H, q, J = 7.6 Hz), 1.43 (9H, s), 1.28 (3H, J = 7.6 Hz). |

TABLE 1-14-continued
| REX | STR | RProp | Data |
|---|---|---|---|
| 89 | | 23 | NMR2 (500 MHz); 7.81-7.76 (1H, m), 7.73-7.67 (1H, m), 7.63-7.56 (1H, m), 7.56-7.49 (1H, m), 7.18-7.12 (3H, m), 5.11 (2H, s), 4.57 (1H, s), 3.46-3.30 (5H, m), 2.80 (2H, t, J = 7.0 Hz), 1.43 (9H, s). |
| 90 | | 90 | NMR2 (500 MHz); 7.83 (1H, t, J = 1.7 Hz), 7.74 (1H, dt, J = 7.9, 1.5 Hz), 7.61 (1H, dt, J = 7.7, 1.4 Hz), 7.51 (1H, t, J = 7.8 Hz), 7.19-7.15 (2H, m), 7.12 (1H, s), 5.13 (2H, s), 4.57 (1H, s), 3.41-3.34 (5H, m), 2.79 (2H, t, J = 7.1 Hz), 1.43 (9H, s). |
TABLE 1-15
| REX | STR | RProp | Data |
|---|---|---|---|
| 91 | | 23 | NMR2 (500 MHz); 7.72-7.67 (2H, m), 7.66-7.60 (2H, m), 7.17 (2H, d, J = 1.3 Hz), 7.13 (1H, s), 5.12 (2H, s), 4.56 (1H, s), 3.44-3.32 (5H, m), 2.79 (2H, t, J = 7.0 Hz), 1.43 (9H, s). |
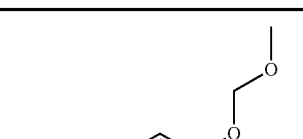

TABLE 1-15-continued

| REX | STR | RProp | Data |
|-----|-----|-------|------|
| 92 | | 23 | NMR2 (500 MHz); 7.43-7.37 (2H, m), 7.16-7.04 (3H, m), 6.91-6.84 (2H, m), 5.23 (1H, s), 5.08 (2H, s), 4.59 (1H, s), 3.46-3.29 (5H, m), 2.77 (2H, t, J = 7.1 Hz), 1.44 (9H, s). |
| 93 | | 23 | NMR2 (500 MHz); 8.79-8.75 (1H, m), 8.59-8.54 (1H, m), 7.86-7.81 (1H, m), 7.37-7.31 (1H, m), 7.21-7.13 (3H, m), 5.13 (2H, s), 4.57 (1H, s), 3.43-3.34 (5H, m), 2.80 (2H, t, J = 7.1 Hz), 1.43 (9H, s). |
| 94 | | 81 | NMR2 (400 MHz); 7.51-7.43 (2H, m), 7.34 (1H, dd, J = 5.1, 1.1 Hz), 7.17-7.02 (3H, m), 5.25 (2H, s), 4.56 (1H, s), 3.50 (3H, s), 3.43-3.31 (2H, m), 2.78 (2H, t, J = 7.0 Hz), 1.44 (9H, s). |

TABLE 1-15-continued

| REX | STR | RProp | Data |
|---|---|---|---|
| 95 | | 23 | NMR2 (500 MHz); 7.57 (1H, dd, J = 3.1, 1.3 Hz), 7.42 (1H, dd, J = 5.0, 1.3 Hz), 7.34 (1H, dd, J = 5.0, 3.0 Hz), 7.32-7.28 (1H, m), 7.14 (1H, d, J = 8.4 Hz), 7.07 (1H, dd, J = 8.4 Hz, 2.3 Hz), 5.17 (2H, s), 4.56 (1H, s), 3.44 (3H, s), 3.39-3.36 (2H, m), 2.78 (2H, t, J = 6.9 Hz), 1.43 (9H, s). |

TABLE 1-16

| REX | STR | RProp | Data |
|---|---|---|---|
| 96 | | 23 | NMR2 (500 MHz); 7.94-7.87 (1H, m), 7.68-7.60 (1H, m), 7.41 (1H, s), 7.39-7.31 (2H, m), 7.24-7.17 (3H, m), 5.03 (2H, s), 4.58 (1H, s), 3.43-3.34 (2H, m), 3.31 (3H, s), 2.80 (2H, t, J = 6.9 Hz), 1.43 (9H, s). |
| 97 | | 80 | NMR2 (500 MHz); 7.25-7.10 (6H, m), 6.98 (1H, s), 5.03 (2H, s), 4.55 (1H, s), 3.39-3.33 (2H, m), 3.31 (3H, s), 2.76 (2H, t, J = 7.0 Hz), 2.17 (3H, s), 1.43 (9H, s). |

TABLE 1-16-continued

| REX | STR | RProp | Data |
|---|---|---|---|
| 98 | | 80 | NMR2 (500 MHz); 7.37-7.28 (1H, m), 7.23 (1H, dd, J = 7.4, 1.7 Hz), 7.19-6.94 (5H, m), 5.05 (2H, s), 4.59 (1H, s), 3.77 (3H, s), 3.44-3.31 (5H, m), 2.77 (2H, t, J = 6.9 Hz), 1.43 (9H, s). |
| 99 | | 80 | NMR2 (500 MHz); 7.34-7.26 (1H, m), 7.20-7.13 (2H, m), 7.07 (1H, s), 6.97-6.84 (2H, m), 5.10 (2H, s), 4.57 (1H, s), 3.43-3.30 (5H, m), 2.78 (2H, t, J = 6.9 Hz), 1.43 (9H, s). |
| 100 | | 100 | NMR2 (500 MHz); 8.61-8.55 (1H, m), 8.45-8.41 (1H, m), 7.64-7.57 (1H, m), 7.21-7.16 (2H, m), 7.15 (1H, s), 5.15 (2H, s), 4.57 (1H, s), 3.42-3.36 (5H, m), 2.80 (2H, t, J = 7.1 Hz), 1.43 (9H, s). |

TABLE 1-17
| REX | STR | RProp | Data |
|---|---|---|---|
| 101 | 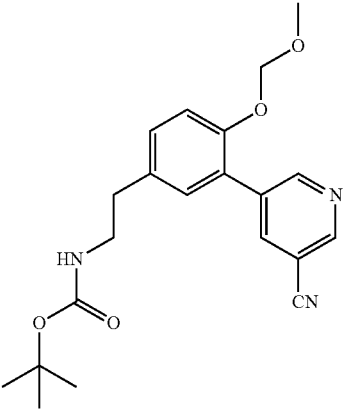 | 23 | NMR2 (500 MHz); 8.95 (1H, d, J = 2.2 Hz), 8.83 (1H, d, J = 2.0 Hz), 8.13 (1H, t, J = 2.1 Hz), 7.26-7.18 (2H, m), 7.14 (1H, s), 5.16 (2H, m), 4.58 (1H, s), 3.43-3.34 (5H, m), 2.81 (2H, t, J = 7.0 Hz), 1.43 (9H, s). |
| 102 | 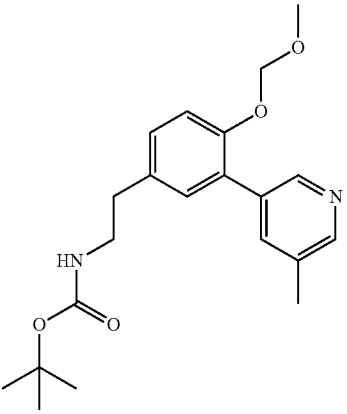 | 23 | NMR2 (500 MHz); 8.58 (1H, d, J = 2.1 Hz), 8.41-8.37 (1H, m), 7.64-7.60 (1H, m), 7.20-7.11 (3H, m), 5.12 (2H, s), 4.58 (1H, s), 3.43-3.34 (5H, m), 2.79 (2H, t, J = 6.9 Hz), 2.39 (3H, s), 1.43 (9H, s). |
| 103 | 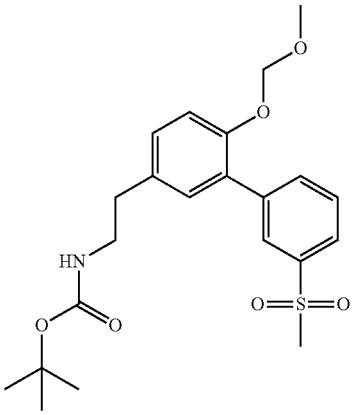 | 23 | NMR2 (500 MHz); 8.14-8.10 (1H, m), 7.93-7.87 (1H, m), 7.84-7.79 (1H, m), 7.61 (1H, t, J = 7.8 Hz), 7.21-7.14 (3H, m), 5.13 (2H, s), 4.58 (1H, s), 3.42-3.33 (5H, m), 3.09 (3H, s), 2.80 (2H, t, J = 7.2 Hz), 1.43 (9H, s). |

TABLE 1-17-continued
| REX | STR | RProp | Data |
|-----|-----|-------|------|
| 104 | 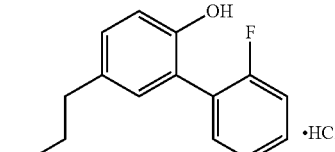 | 23 | NMR2 (500 MHz); 7.43-7.33 (3H, m), 7.27-7.21 (1H, m), 7.16-7.08 (3H, m), 5.08 (2H, s), 4.57 (1H, s), 3.77 (2H, s), 3.42-3.33 (5H, m), 3.03 (3H, s), 2.97 (3H, s), 2.78 (2H, t, J = 7.0 Hz), 1.43 (9H, s). |
| 105 | 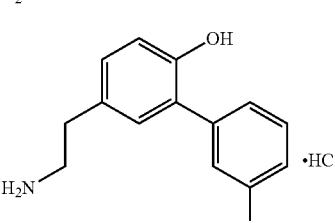 | 23 | NMR2 (500 MHz); 8.22-8.17 (1H, m), 8.04-7.98 (1H, m), 7.74-7.68 (1H, m), 7.48 (1H, t, J = 7.7 Hz), 7.19-7.11 (3H, m), 5.11 (2H, s), 4.57 (1H, s), 4.40 (2H, q, J = 7.1 Hz), 3.42-3.33 (5H, m), 2.80 (2H, t, J = 7.0 Hz), 1.43 (9H, s), 1.40 (3H, t, J = 7.1 Hz). |
TABLE 1-18
| REX | STR | RProp | Data |
|-----|-----|-------|------|
| 106 | 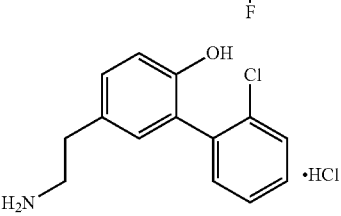 | 106 | NMR1 (500 MHz); 9.54 (1H, s), 7.94 (3H, s), 7.42-7.34 (2H, m), 7.27-7.18 (2H, m), 7.10 (1H, dd, J = 8.3, 2.3 Hz), 7.05 (1H, d, J = 2.2 Hz), 6.91 (1H, d, J = 8.2 Hz), 3.05-2.95 (2H, m), 2.84-2.77 (2H, m). |
| 107 | | 106 | NMR1 (500 MHz); 9.66 (1H, s), 7.82 (3H, s), 7.48-7.35 (3H, m), 7.19 (1H, d, J = 2.3 Hz), 7.17-7.10 (1H, m), 7.07 (1H, dd, J = 8.3, 2.3 Hz), 6.93 (1H, d, J = 8.2 Hz), 3.07-2.99 (2H, m), 2.80 (2H, t, J = 7.8 Hz). |
| 108 | | 106 | NMR1 (500 MHz); 9.46 (1H, s), 7.85 (3H, s), 7.54-7.46 (1H, m), 7.39-7.29 (3H, m), 7.09 (1H, dd, (J = 8.3, 2.3 Hz), 6.97 (1H, d, J = 2.3 Hz), 6.89 (1H, d, J = 8.3 Hz), 3.03-2.98 (2H, m), 2.82-2.76 (2H, m). |

TABLE 1-18-continued

| REX | STR | RProp | Data |
|---|---|---|---|
| 109 | | 109 | NMR1 (500 MHz); 9.72 (1H, s), 7.96 (3H, s), 7.62 (1H, t, J = 1.9 Hz), 7.58-7.51 (1H, m), 7.44 (1H, t, J = 7.9 Hz), 7.41-7.34 (1H, m), 7.19 (1H, d, J = 2.3 Hz), 7.08 (1H, dd, J = 8.2, 2.3 Hz), 6.95 (1H, d, J = 8.2 Hz), 3.03 (2H, s), 2.86-2.80 (2H, m). |
| 110 | | 106 | NMR1 (500 MHz); 9.63 (1H, s), 7.86 (3H, s), 7.62-7.56 (2H, m), 7.49-7.42 (2H, m), 7.15 (1H, d, J = 2.3 Hz), 7.06 (1H, dd, J = 8.2, 2.3 Hz), 6.92 (1H, d, J = 8.3 Hz), 3.07-2.97 (2H, m), 2.80 (2H, t, J = 8.2 Hz). |
| 111 | | 109 | NMR1 (500 MHz); 9.70 (1H, s), 8.01 (3H, s), 7.31-7.19 (3H, m), 7.12 (1H, dd, J = 8.3, 2.3 Hz), 7.09 (1H, d, J = 2.3 Hz), 6.93 (1H, d, J = 8.2 Hz), 3.05-2.96 (2H, m), 2.84-2.79 (2H, m). |

TABLE 1-19

| REX | STR | RProp | Data |
|---|---|---|---|
| 112 | | 106 | NMR1 (500 MHz); 9.72 (1H, s), 8.04 (3H,s), 7.45-7.35 (1H, m), 7.28-7.17 (2H, m), 7.14 (1H, dd, J = 8.3, 2.3 Hz), 7.09 (1H, d, J = 2.3 Hz), 6.95 (1H, d, J = 8.3 Hz), 3.05-2.95 (2H, m), 2.86-2.80 (2H, m). |
| 113 | | 109 | NMR1 (500 MHz); 9.89 (1H, s), 8.02 (3H, s), 7.35-7.09 (5H, m), 6.97 (1H, d, J = 8.3 Hz), 3.09-2.98 (2H, m), 2.83 (2H, t, J = 7.7 Hz). |
| 114 | | 109 | NMR1 (500 MHz); 9.47 (1H, s), 7.96 (3H, s), 7.37-7.32 (2H, m), 7.31-7.24 (1A, m), 7.14-7.07 (2H, m), 7.03 (1H, dd, J = 8.2, 2.3 Hz), 6.92 (1H, d, J = 8.2 Hz), 3.06-2.96 (2H, m), 2.85-2.79 (2H, m), 2.35 (3H, s). |

TABLE 1-19-continued

| REX | STR | RProp | Data |
|---|---|---|---|
| 115 | (biphenyl with OH, ethyl substituent, aminoethyl group) ·HCl | 109 | NMR1 (500 MHz); 9.46 (1H, s), 7.92 (3H, s), 7.41-7.34 (2H, m), 7.34-7.27 (1H, m), 7.17-7.11 (2H, m), 7.04 (1H, dd, J = 8.2, 2.3 Hz), 6.91 (1H, d, J = 8.2 Hz), 3.07-2.97 (2H, m), 2.85-2.78 (2H, m), 2.65 (2H, q, J = 7.6 Hz), 1.22 (3H, t, J = 7.6 Hz). |
| 116 | (biphenyl with OH, CF₃ substituent, aminoethyl group) ·HCl | 109 | NMR1 (500 MHz); 9.79 (1H, s), 7.98 (3H, s), 7.92-7.84 (2H, m), 7.70-7.62 (2H, m), 7.23 (1H, d, J = 2.2 Hz), 7.11 (1H, dd, J = 8.3, 2.2 Hz), 6.98 (1H, d, J = 8.2 Hz), 3.09-2.99 (2H, m), 2.84 (2H, t, J = 7.7 Hz). |
| 117 | (biphenyl with OH, CN substituent, aminoethyl group) ·HCl | 117 | NMR1 (500 MHz); 9.81 (1H, s), 7.99 (1H, t, J = 1.8 Hz), 7.97-7.88 (4H, m), 7.77 (1H, dt, J = 7.7, 1.4 Hz), 7.62 (1H, t, J =7.8 Hz), 7.24 (1H, d, J = 2.2 Hz), 7.11 (1H, dd, J = 8.3, 2.3 Hz), 6.96 (1H, d, J = 8.3 Hz), 3.09-2.98 (2H, m), 2.86-2.79 (2H, m). |

TABLE 1-20

| REX | STR | RProp | Data |
|---|---|---|---|
| 118 | (biphenyl with OH, CN substituent, aminoethyl group) ·HCl | 109 | NMR1 (500 MHz); 9.86 (1H, s), 7.94 (3H, s), 7.87 (2H, d, J = 8.3 Hz), 7.78 (2H, d, J = 8.3 Hz), 7.22 (1H, d, J = 2.3 Hz), 7.12 (1H, dd, J = 8.3, 2.3 Hz), 6.96 (1H, d, J = 8.3 Hz), 3.08-2.97 (2H, m), 2.82 (2H, t, J = 7.7 Hz). |
| 119 | (biphenyl with OH, OH substituent, aminoethyl group) ·HCl | 109 | NMR1 (500 MHz); 9.42 (1H, s), 9.35 (1H, s), 7.91 (3H, s), 7.40-7.31 (2H, m), 7.07 (1H, d, J = 2.3 Hz), 6.96 (1H, dd, J = 8.2, 2.3 Hz), 6.87 (1H, d, J = 8.2 Hz), 6.82-6.75 (2H, m), 3.05-2.95 (2H, m), 2.82-2.75 (2H, m). |
| 120 | (phenol with pyridine substituent, aminoethyl group) ·2HCl | 109 | NMR1 (500 MHz); 10.29 (1H, s), 9.10-9.06 (1H, m), 8.82-8.77 (1H, m), 8.72-8.66 (1H, m), 8.08 (3H, s), 8.04-7.97 (1H, m), 7.40 (1H, d, J = 2.2 Hz), 7.21 (1H, dd, J = 8.3, 2.3 Hz), 7.05 (1H, d, J = 8.3 Hz), 3.09-2.99 (2H, m), 2.90-2.83 (2H, m). |

TABLE 1-20-continued

| REX | STR | RProp | Data |
|---|---|---|---|
| 121 | (structure: 4-(2-aminoethyl)-2-(thiophen-2-yl)phenol ·HCl) | 109 | NMR1 (500 MHz); 10.23-10.19 (1H, m), 8.06 (3H, s), 7.60 (1H, dd, J = 3.7, 1.2 Hz), 7.53-7.47 (2H, m), 7.10 (1H, dd, J = 5.2, 3.6 Hz), 7.06-6.93 (2H, m), 3.07-2.97 (2H, m), 2.87-2.80 (2H, m). |
| 122 | (structure: 4-(2-aminoethyl)-2-(thiophen-3-yl)phenol ·HCl) | 109 | NMR1 (500 MHz); 9.76 (1H, s), 7.94 (3H, s), 7.83 (1H, dd, J = 2.7, 1.6 Hz), 7.58-7.52 (2H, m), 7.39 (1H, d, J = 2.2 Hz), 6.99 (1H, dd, J = 8.2, 2.3 Hz), 6.91 (1H, d, J = 8.2 Hz), 3.07-2.97 (2H, m), 2.84-2.78 (2H, m). |
| 123 | (structure: 4-(2-aminoethyl)-2-(benzothiophen-3-yl)phenol ·HCl) | 106 | NMR1 (500 MHz); 9.53 (1H, s), 8.05-7.99 (1H, m), 7.86 (3H, s), 7.66 (1H, s), 7.65-7.58 (1H, m), 7.42-7.32 (2H, m), 7.18 (1H, d, J = 2.3 Hz), 7.14 (1H, dd, J = 8.3, 2.3 Hz), 6.98 (1H, d, J = 8.2 Hz), 3.08-2.99 (2H, m), 2.86-2.79 (2H, m). |

TABLE 1-21

| REX | STR | RProp | Data |
|---|---|---|---|
| 124 | (structure: 4-(2-aminoethyl)-2'-methyl-[1,1'-biphenyl]-2-ol ·HCl) | 106 | NMR1 (500 MHz); 9.34 (1H, s), 7.93 (3H, s), 7.25-7.16 (3H, m), 7.14-7.08 (1H, m), 7.05 (1H, dd, J = 8.2, 2.3 Hz), 6.93-6.86 (2H, m), 3.05-2.95 (2H, m), 2.83-2.76 (2H, m), 2.12 (3H, s). |
| 125 | (structure: 4-(2-aminoethyl)-2'-methoxy-[1,1'-biphenyl]-2-ol ·HCl) | 106 | NMR1 (400 MHz); 9.10 (1H, s), 7.97 (3H, s), 7.35-7.26 (1H, m), 7.15 (1H, dd, J = 7.4, 1.8 Hz), 7.08-6.89 (4H, m), 6.84 (1H, d, J = 8.2 Hz), 3.70 (3H, s), 3.03-2.91 (2H, m), 2.82-2.74 (2H, m). |
| 126 | (structure: 4-(2-aminoethyl)-2',4'-difluoro-[1,1'-biphenyl]-2-ol ·HCl) | 106 | NMR1 (500 MHz); 9.60 (1H, s), 7.97 (3H, s), 7.46-7.37 (1H, m), 7.30-7.22 (1H, m), 7.17-7.08 (2H, m), 7.06-7.02 (1H, m), 6.91 (1H, d, J = 8.2 Hz), 3.05-2.95 (2H, m), 2.84-2.77 (2H, m). |

TABLE 1-21-continued

| REX | STR | RProp | Data |
|---|---|---|---|
| 127 | | 127 | NMR1 (500 MHz); 10.03 (1H, s), 8.75-8.70 (1H, m), 8.60-8.54 (1H, m), 8.04-7.97 (4H, m), 7.32 (1H, d, J = 2.2 Hz), 7.15 (1H, dd, J = 8.3, 2.3 Hz), 7.00 (1H, d, J = 8.3 Hz), 3.09-2.99 (2H, m), 2.88-2.81 (2H, m). |
| 128 | | 106 | NMR1 (500 MHz); 10.11 (1H, s), 9.09 (1H, d, J = 2.2 Hz), 8.96 (1H, d, J = 2.1 Hz), 8.50 (1H, t, J = 2.1 Hz), 8.10 (3H, s), 7.33 (1H, d, J = 2.2 Hz), 7.16 (1H, dd, J = 8.3, 2.3 Hz), 7.02 (1H, d, J = 8.2 Hz), 3.09-2.99 (2H, m), 2.90-2.82 (2H, m). |
| 129 | | 106 | NMR1 (500 MHz); 10.40 (1H, s), 8.98-8.94 (1H, m), 8.72 (1H, s), 8.64 (1H, s), 8.20 (3H, s), 7.43 (1H, d, J = 2.3 Hz), 7.21 (1H, dd, J = 8.4, 2.2 Hz), 7.09 (1H, d, J = 8.3 Hz), 3.09-2.99 (2H, m), 2.92-2.85 (2H, m), 2.54 (3H, s). |

TABLE 1-22

| REX | STR | RProp | Data |
|---|---|---|---|
| 130 | | 106 | NMR1 (500 MHz); 9.80 (1H, s), 8.09 (1H, t, J = 1.9 Hz), 7.98-7.81 (5H, m), 7.69 (1H, t, J = 7.8 Hz), 7.24 (1H, d, J = 2.3 Hz), 7.12 (1H, dd, J = 8.3, 2.3 Hz), 6.97 (1H, d, J = 8.2 Hz), 3.25 (3H, s), 3.09-2.98 (2H, m), 2.87-2.80 (2H, m). |
| 131 | | 109 | NMR1 (500 MHz); 9.50 (1H, s), 7.94 (3H, s), 7.44-7.38 (2H, m), 7.32 (1H, t, J = 7.5 Hz), 7.18-1.12 (1H, m), 7.11 (1H, d, J = 2.3 Hz), 7.04 (1H, dd, J = 8.2, 2.3 Hz), 6.91 (1H, d, J = 8.2 Hz), 3.72 (2H, s), 3.05-2.95 (5H, m), 2.85-2.78 (5H, m). |

TABLE 1-22-continued

| REX | STR | RProp | Data |
|---|---|---|---|
| 132 | | 132 | NMR1 (500 MHz); 9.66 (1H, s), 8.04 (3H, s), 7.66-7.61 (1H, m), 7.59-7.55 (1H, m), 7.46 (1H, t, J = 7.7 Hz), 7.35-7.29 (1H, m), 7.18 (1H, d, J = 2.3 Hz), 7.07 (1H, dd, J = 8.3, 2.3 Hz), 6.95 (1H, d, J = 8.2 Hz), 3.05-2.92 (8H, m), 2.87-2.80 (2H, m). |
| 133 | | 37 | NMR1 (500 MHz); 9.35 (1H, s), 7.70 (1H, s), 7.58-7.51 (1H, m), 7.44-7.37 (2H, m), 7.36-7.29 (1H, m), 7.14 (1H, dd, J = 8.3, 2.3 Hz), 7.00 (1H, s), 6.89 (1H, d, J = 8.2 Hz), 4.91 (2H, s), 3.97-3.52 (2H, m), 2.84 (2H, t, J = 7.4 Hz), 1.67 (6H, s). |
| 134 | | 37 | NMR1 (500 MHz); 9.51 (1H, s), 7.67 (1H, s), 7.59-7.55 (1H, m), 7.53-7.46 (1H, m), 7.42 (1H, t, J = 7.8 Hz), 7.38-7.32 (1H, m), 7.17 (1H, s), 7.06 (1H, dd, J = 8.2, 2.2 Hz), 6.87 (1H, d, J = 8.2 Hz), 4.85 (2H, s), 3.94-3.48 (2H, m), 2.80 (2H, t, J = 7.3 Hz), 1.61 (6H, s). |

TABLE 1-23

| REX | STR | RProp | Data |
|---|---|---|---|
| 135 | | 37 | NMR1 (500 MHz); 9.47 (1H, s), 7.67 (1H, s), 7.59-7.53 (2H, m), 7.47-7.41 (2H, m), 7.15 (1H, s), 7.05 (1H, dd, J = 8.2, 2.3 Hz), 6.86 (1H, d, J = 8.3 Hz), 4.86 (2H, s), 3.92-3.50 (2H, m), 2.79 (2H, t, J = 7.4 Hz), 1.61 (6H, s). |

TABLE 1-23-continued
| REX | STR | RProp | Data |
|---|---|---|---|
| 136 | 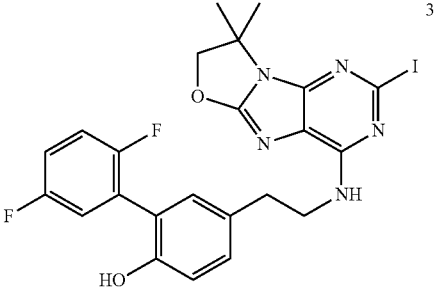 | 37 | NMR1 (500 MHz); 9.49 (1H, s), 7.65 (1H, s), 7.30-7.02 (5H, m), 6.86 (1H, d, J = 8.2 Hz), 4.84 (2H, s), 3.89-3.47 (2H, m), 2.78 (2H, t, J = 7.4 Hz), 1.60 (6H, s). |
| 137 | 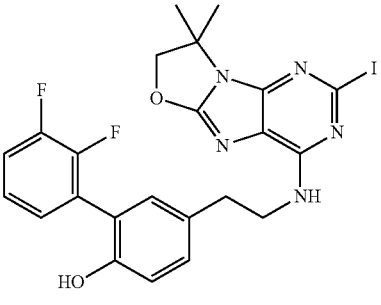 | 37 | NMR1 (500 MHz); 9.50 (1H, s), 7.66 (1H, s), 7.43-7.33 (1H, m), 7.26-7.18 (1H, m), 7.17-7.09 (2H, m), 7.08-7.04 (1H, m), 6.86 (1H, d, J = 8.2 Hz), 4.85 (2H, s), 3.91-3.47 (2H, m), 2.79 (2H, t, J = 7.3 Hz), 1.60 (6H, s). |
| 138 | 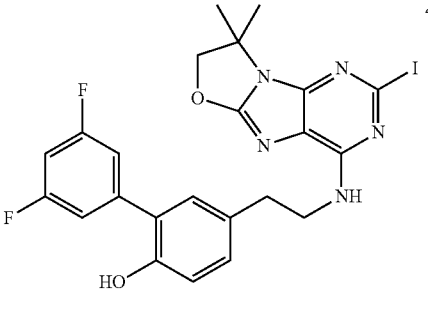 | 46 | NMR1 (500 MHz); 9.66 (1H, s), 7.66 (1H, s), 7.27-7.05 (5H, m), 6.87 (1H, d, J = 8.3 Hz), 4.84 (2H, s), 3.91-3.48 (2H, m), 2.79 (2H, t, J = 7.2 Hz), 1.60 (6H, s). |
| 139 | 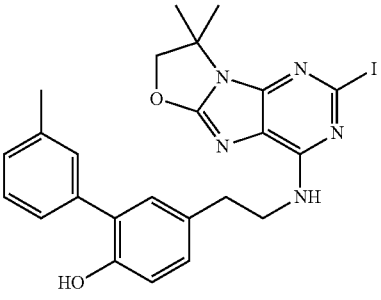 | 46 | NMR1 (500 MHz); 9.27 (1H, s), 7.66 (1H, s), 7.34-7.29 (2H, m), 7.26 (1H, t, J = 7.8 Hz), 7.13-7.07 (2H, m), 7.02 (1H, dd, J = 8.2, 2.2 Hz), 6.84 (1H, d, J = 8.2 Hz), 4.85 (2H, s), 3.93-3.47 (2H, m), 2.79 (2H, t, J = 7.4 Hz), 2.34 (3H, s), 1.61 (6H, s). |

TABLE 1-24

| REX | STR | RProp | Data |
|---|---|---|---|
| 140 | | 46 | NMR1 (500 MHz); 9.27 (1H, s), 7.66 (1H, s), 7.36-7.31 (2H, m), 7.28 (1H, t, J = 7.8 Hz), 7.16-7.10 (2H, m), 7.02 (1H, dd, J = 8.2, 2.3 Hz), 6.84 (1H, d, J = 8.2 Hz), 4.85 (2H, s), 3.91-3.49 (2H, m), 2.79 (2H, t, J = 7.4 Hz), 2.64 (2H, q, J =7.6 Hz), 1.61 (6H, s), 1.21 (3H, t, J = 7.6 Hz). |
| 141 | | 37 | NMR1 (500 MHz); 9.58 (1H, s), 7.86 (1H, s), 7.84-7.79 (1H, m), 7.69-7.61 (3H, m), 7.20 (1H, s), 7.08 (1H, dd, J = 8.2, 2.2 Hz), 6.88 (1H, d, J = 8.2 Hz), 4.84 (2H, s), 3.91-3.51 (2H, m), 2.81 (2H, t, J = 7.3 Hz), 1.60 (6H, s). |
| 142 | | 142 | NMR1 (500 MHz); 9.62 (1H, s), 7.95 (1H, s), 7.88 (1H, d, J = 7.9 Hz), 7.75 (1H, d, J = 7.7 Hz), 7.67 (1H, s), 7.60 (1H, t, J = 7.8 Hz), 7.22 (1H, s), 7.08 (1H, dd, J = 8.3, 2.2 Hz), 6.88 (1H, d, J = 8.2 Hz), 4.85 (2H, s), 3.92-3.51 (2H, m), 2.80 (2H, t, J = 7.3 Hz), 1.60 (6H, s). |
| 143 | | 37 | NMR1 (500 MHz); 9.66 (1H, s), 7.84 (2H, d, J = 8.4 Hz), 7.75 (2H, d, J = 8.3 Hz), 7.67 (1H, s), 7.21 (1H, s), 7.10 (1H, dd, J = 8.3, 2.2 Hz), 6.88 (1H, d, J = 8.2 Hz), 4.85 (2H, s), 3.90-3.47 (2H, m), 2.80 (2H, t, J = 7.4 Hz), 1.60 (6H, s). |
| 144 | | 37 | NMR1 (500 MHz); 9.35 (1H, s), 9.16 (1H, s), 7.64 (1H, s), 7.36-7.30 (2H, m), 7.05 (1H, s), 6.95 (1H, dd, J = 8.2, 2.3 Hz), 6.83-6.74 (3H, m), 4.85 (2H, s), 3.89-3.45 (2H, m), 2.77 (2H, t, J = 7.4 Hz), 1.60 (6H, s). |

TABLE 1-25

| REX | STR | RProp | Data |
|---|---|---|---|
| 145 | | 37 | NMR1 (500 MHz); 9.56 (1H, s), 8.69 (1H, d, J = 2.3 Hz), 8.48 (1H, dd, J = 4.8, 1.7 Hz), 7.91 (1H, dt, J = 7.9, 2.0 Hz), 7.67 (1H, s), 7.41 (1H, dd, J = 7.9, 4.8 Hz), 7.18 (1H, s), 7.08 (1H, dd, J = 8.3, 2.2 Hz), 6.88 (1H, d, J = 8.2 Hz), 4.85 (2H, s), 3.91-3.48 (2H, m), 2.81 (2H, t, J = 7.3 Hz), 1.60 (6H, s). |
| 146 | | 146 | NMR1 (500 MHz); 9.96 (1H, s), 7.67 (1H, s), 7.56 (1H, d, J = 3.6 Hz), 7.48 (2H, d, J = 5.1 Hz), 7.11-7.08 (1H, m), 7.00 (1H, dd, J = 8.2, 2.1 Hz), 6.86 (1H, d, J = 8.2 Hz), 4.85 (2H, s), 3.90-3.50 (2H, m), 2.80 (2H, t, J = 7.4 Hz), 1.61 (6H, s). |
| 147 | | 146 | NMR1 (500 MHz); 9.57 (1H, s), 7.79-7.75 (1H, m), 7.66 (1H, s), 7.56-7.49 (2H, m), 7.37 (1H, s), 6.98 (1H, dd, J = 8.2, 2.2 Hz), 6.84 (1H, d, J = 8.2 Hz), 4.85 (2H, s), 3.93-3.47 (2H, m), 2.79 (2H, t, J = 7.4 Hz), 1.60 (6H, s). |
| 148 | | 46 | NMR1 (500 MHz); 9.36 (1H, s), 8.03-7.98 (1H, m), 7.67 (1H, s), 7.63-7.55 (2H, m), 7.40-7.30 (2H, m), 7.17-7.09 (2H, m), 6.92 (1H, d, J = 8.2 Hz), 4.85 (2H, s), 3.91-3.47 (2H, m), 2.81 (2H, t, J = 7.3 Hz), 1.60 (6H, s). |
| 149 | | 46 | NMR1 (500 MHz); 9.15 (1H, s), 7.62 (1H, s), 7.23-7.13 (3H, m), 7.08-7.01 (2H, m), 6.86 (1H, s), 6.81 (1H, d, J = 8.2 Hz), 4.85 (2H, s), 3.91-3.47 (2H, m), 2.77 (2H, t, J = 7.5 Hz), 2.08 (3H, s), 1.60 (6H, s). |

TABLE 1-26

| REX | STR | RProp | Data |
|-----|-----|-------|------|
| 150 | | 46 | NMR1 (500 MHz); 8.91 (1H, s), 7.63 (1H, s), 7.32-7.25 (1H, m), 7.11 (1H, dd, J = 7.5, 1.8 Hz), 7.05-6.97 (2H, m), 6.97-6.91 (2H, m), 6.78 (1H, d, J = 8.2 Hz), 4.85 (2H, s), 3.85-3.46 (2H, m), 3.69 (3H, s), 2.75 (2H, t, J = 3.6 Hz), 1.60 (6H, s). |
| 151 | | 46 | NMR1 (500 MHz); 9.40 (1H, s), 7.66 (1H, s), 7.41-7.32 (1H, m), 7.28-7.20 (1H, m), 7.14-7.06 (2H, m), 7.02 (1H, d, J = 2.3 Hz), 6.84 (1H, d, J = 8.2 Hz), 4.85 (2H, s), 3.90-3.47 (2H, m), 2.78 (2H, t, J = 7.5 Hz), 1.60 (6H, s). |
| 152 | | 152 | NMR1 (500 MHz); 9.74 (1H, s), 8.60 (1H, t, J = 1.8 Hz), 8.49 (1H, d, J = 2.8 Hz), 7.87-7.80 (1H, m), 7.67 (1H, s), 7.24 (1H, s), 7.12 (1H, dd, J = 8.3, 2.2 Hz), 6.90 (1H, d, J = 8.2 Hz), 4.85 (2H, s), 3.93-3.50 (2H, m), 2.81 (2H, t, J = 7.3 Hz), 1.60 (6H, s). |
| 153 | | 146 | NMR1 (500 MHz); 9.84 (1H, s), 9.01 (1H, d, J = 2.2 Hz), 8.93 (1H, d, J = 1.9 Hz), 8.41 (1H, t, J = 2.1 Hz), 7.68 (1H, s), 7.29 (1H, s), 7.14 (1H, dd, J = 8.3, 2.2 Hz), 6.91 (1H, d, J = 8.2 Hz), 4.85 (2H, s), 3.91-3.50 (2H, m), 2.81 (2H, t, J = 7.2 Hz), 1.60 (6H, s). |
| 154 | | 37 | NMR1 (500 MHz); 9.84 (1H, s), 9.06-8.98 (1H, m), 8.95-8.91 (1H, m), 8.44-8.39 (1H, m), 7.96-7.90 (1H, m), 7.29 (1H, s), 7.17-7.11 (1H, m), 6.91 (1H, d, J = 8.3 Hz), 3.84 (2H, s), 3.80-3.53 (2H, m), 2.83 (2H, t, J = 7.2 Hz), 1.65 (6H, s). |

TABLE 1-27
| REX | STR | RProp | Data |
|---|---|---|---|
| 155 | 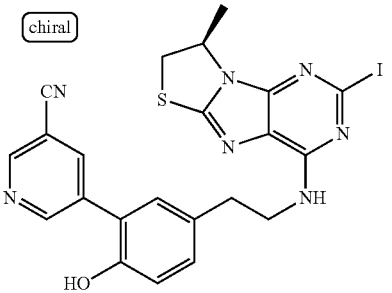 | 146 | NMR1 (500 MHz); 9.84 (1H, s), 9.01 (1H, d, J = 2.2 Hz), 8.93 (1H, d, J = 2.0 Hz), 8.41 (1H, t, J = 2.1 Hz), 3.96-7.92 (1H, m), 7.29 (1H, s), 7.14 (1H, dd, J = 8.3, 2.2 Hz), 6.91 (1H, d, J = 8.2 Hz), 4.84-4.76 (1H, m), 4.14 (1H, dd, J = 11.2, 7.2 Hz), 4.01-3.53 (3H, m), 2.83 (2H, t, J = 7.2 Hz), 1.51 (3H, d, J = 6.3 Hz). |
| 156 | 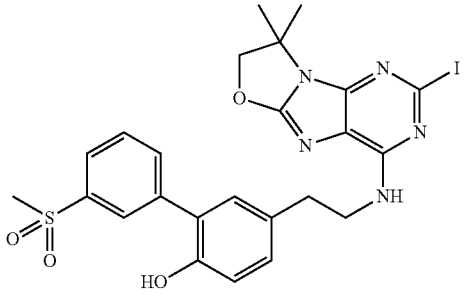 | 37 | NMR1 (500 MHz); 9.62 (1H, s), 8.08 (1H, t, J = 1.8 Hz), 7.90-7.82 (2H, m), 7.71-7.64 (2H, m), 7.22 (1H, s), 7.10 (1H, dd, J = 8.2, 2.2 Hz), 6.89 (1H, d, J = 8.2 Hz), 4.85 (2H, s), 3.90-3.50 (2H, m), 3.24 (3H, s), 2.81 (2H, t, J = 7.4 Hz), 1.60 (6H, s). |
| 157 | 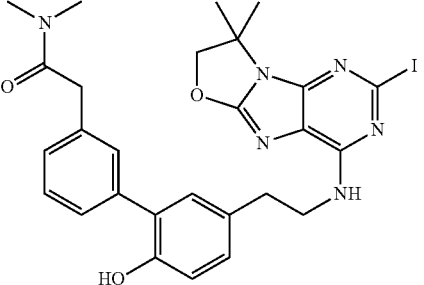 | 37 | NMR1 (500 MHz); 9.32 (1H, s), 7.66 (1H, s), 7.41-7.35 (2H, m), 7.30 (1H, t, J = 7.9 Hz), 7.16-7.09 (2H, m), 7.02 (1H, dd, J = 8.2, 2.2 Hz), 6.84 (1H, d, J = 8.2 Hz), 4.85 (2H, s), 3.71 (2H, s), 3.87-3.48 (2H, m), 3.02 (3H, s), 2.83 (3H, s), 2.78 (2H, t, J = 7.4 Hz), 1.60 (6H, s). |
| 158 | 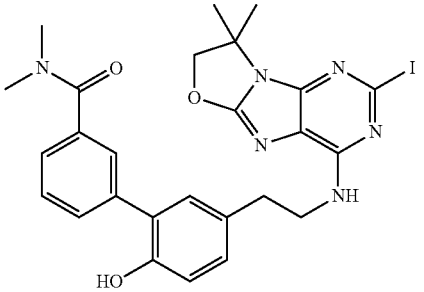 | 37 | NMR1 (500 MHz); 9.43 (1H, s), 7.67 (1H, s), 7.61-7.56 (1H, m), 7.56-7.52 (1H, m), 7.44 (1H, t, J = 7.7 Hz), 7.33-7.28 (1H, m), 7.17 (1H, s), 7.04 (1H, dd, J = 8.2, 2.2 Hz), 6.86 (1H, d, J = 8.2 Hz), 4.85 (2H, s), 3.91-3.48 (2H, m), 2.99 (3H, s), 2.95 (3H, s), 2.79 (2H, t, J = 7.3 Hz), 1.60 (6H, s). |

TABLE 1-28

| REX | STR | RProp | Data |
|-----|-----|-------|------|
| 159 | | 159 | NMR1 (500 MHz); 9.34 (1H, s), 8.63 (1H, d, J = 2.9 Hz), 8.38-8.32 (1H, m), 7.55-7.51 (2H, m), 7.47-7.37 (4H, m), 7.36-7.29 (1H, m), 7.22 (1H, dd, J = 8.4, 2.1 Hz), 7.08 (1H, d, J = 8.4 Hz), 5.13 (2H, s), 4.91 (2H, s), 3.77 (2H, s), 2.92-2.86 (2H, m), 1.71 (6H, s). |
| 160 | | 160 | NMR1 (500 MHz); 9.33 (1H, s), 8.62 (1H, d, J = 2.9 Hz), 8.37-8.31 (1H, m), 7.55 (1H, s), 7.39-7.20 (8H, m), 7.12-6.98 (3H, m), 6.84 (1H, dd, J = 8.2, 2.6 Hz), 5.04 (2H, s), 4.91 (2H, s), 3.81 (2H, s), 3.69 (3H, s), 2.94 (2H, t, J = 7.2 Hz), 1.70 (6H, s). |
| 161 | | 37 | NMR2 (500 MHz); 7.36-7.29 (2H, m), 7.22-7.05 (4H, m), 6.90 (1H, d, J = 8.2 Hz), 6.45 (1H, s), 5.66 (1H, s), 4.53-4.46 (2H, m), 4.16-4.08 (2H, m), 3.80 (2H, s), 2.86 (2H, t, J = 6.9 Hz), 2.31-2.22 (2H, m). |
| 162 | | 37 | NMR1 (500 MHz); 9.35 (1H, s), 7.97 (1H, t, J = 5.9 Hz), 7.40-7.33 (1H, m), 7.30 (1H, t, J = 7.5 Hz), 7.25-7.16 (2H, m), 7.11-6.99 (2H, m), 6.84 (1H, d, J = 8.2 Hz), 4.11-4.07 (2H, m), 3.98-3.51 (2H, m), 3.30-3.25 (2H, m), 2.81-2.78 (2H, m), 2.29-2.24 (2H, m). |
| 163 | | 46 | NMR1 (500 MHz); 9.64 (1H, s), 7.99-7.91 (2H, m), 7.86 (1H, dt, J = 8.0, 1.4 Hz), 7.75 (1H, d, J = 7.7 Hz), 7.60 (1H, t, J = 7.8 Hz), 7.21 (1H, s), 7.08 (1H, dd, J = 8.4, 2.1 Hz), 6.88 (1H, d, J = 8.0 Hz), 3.84 (2H, s), 3.58 (2H, s), 2.81 (2H, t, J = 7.3 Hz), 1.64 (6H, s). |

TABLE 1-29

| REX | STR | RProp | Data |
|---|---|---|---|
| 164 | (chiral) [structure] | 46 | NMR1 (500 MHz); 9.62 (1H, s), 7.98-7.91 (2H, m), 7.86 (1H, dt, J = 8.1, 1.4 Hz), 7.75 (1H, d, J = 7.7 Hz), 7.60 (1H, t, J = 7.6 Hz), 7.20 (1H, s), 7.08 (1H, dd, J = 8.3, 2.2 Hz), 6.88 (1H, d, J = 8.2 Hz), 4.85-4.75 (1H, m), 4.15 (1H, dd, J = 11.3, 7.2 Hz), 4.00-3.52 (3H, m), 2.81 (2H, t, J = 7.2 Hz), 1.51 (3H, d, J = 6.4 Hz). |
| 165 | [structure] | 60 | NMR1 (500 MHz); 9.51 (1H, s), 8.50 (1H, d, J = 2.2 Hz), 8.31 (1H, d, J = 2.1 Hz), 7.74-7.61 (2H, m), 7.16 (1H, s), 7.07 (1H, dd, J = 8.2, 2.2 Hz), 6.87 (1H, d, J = 8.3 Hz), 4.85 (2H, s), 3.89-3.50 (2H, m), 2.80 (2H, t, J = 7.3 Hz), 2.33 (3H, s), 1.60 (6H, s). |
| 166 | [structure] | 46 | NMR1 (500 MHz); 9.51 (1H, s), 8.52-8.48 (1H, m), 8.33-8.29 (1H, m), 7.94-7.91 (1H, m), 7.68 (1H, s), 7.15 (1H, s), 7.07 (1H, dd, J = 8.3, 2.2 Hz), 6.87 (1H, d, J = 8.2 Hz), 3.84 (2H, s), 3.57 (2H, s), 2.81 (2H, t, J = 7.3 Hz), 2.34 (3H, s), 1.66 (6H, s). |
| 167 | (chiral) [structure] | 46 | NMR1 (500 MHz); 9.51 (1H, s), 8.51 (1H, d, J =2.1 Hz), 8.31 (1H, s), 7.93 (1H, s), 7.68 (1H, s), 7.15 (1H, s), 7.07 (1H, dd, J = 8.2, 2.2 Hz), 6.87 (1H, d, J = 8.2 Hz), 4.85-4.75 (1H, m), 4.23-4.11 (1H, m), 3.98-3.51 (3H, m), 2.81 (2H, t, J = 7.1 Hz), 2.34 (3H, s), 1.52 (3H, d, J = 6.3 Hz). |

Example 1

Synthesis of 4-[2-[[2-(5-fluoropyridin-3-yl)-8,8-dimethyl-7H-purino[8,9-b][1,3]oxazol-4-yl]amino]ethyl]J-2-phenylphenol Under nitrogen atmosphere, a mixture of 4-[2-[(2-iodo-8,8-dimethyl-7H-purino[8,9-b][1,3]oxazol-4-yl)amino]ethyl]-2-phenylphenol (60.0 mg), 5-fluoropyridine-3-boronic acid (24.1 mg), Pd(dppf)Cl$_2$'DCM (9.3 mg), K$_3$PO$_4$ (48.3 mg), and DME/water (4/1) (2 ml) was stirred under reflux with heating for 2 hours. The reaction mixture was concentrated, and the residue was then purified by column chromatography (Hexane/AcOEt). The product was washed with Hexane/AcOEt to obtain the object compound (39.0 mg).

Example 2

Synthesis of 2-(2-fluorophenyl)-4-[2-[[2-(5-fluoropyridin-3-yl)-8,8-dimethyl-7H-purino[8,9-b][1,3]oxazol-4-yl]amino]ethyl]phenol Under nitrogen atmosphere, a mixture of 2-(2-fluorophenyl)-4-[2-[(2-iodo-8,8-dimethyl-7H-purino[8,9-b][1,3]oxazol-4-yl)amino]ethyl]phenol (60.0 mg), 5-fluoropyridine-3-boronic acid (23.3 mg), Pd(dppf)Cl$_2$ DCM (9.0 mg), K$_3$PO$_4$ (46.7 mg), and DME/water (4/1) (2 ml) was stirred under reflux with heating for 2 hours. The reaction mixture was concentrated, and the residue was then purified by column chromatography (Hexane/AcOEt). The product was washed with Hexane/AcOEt to obtain the object compound (36.0 mg).

Example 13

Synthesis of 4-[2-[[2-(5-fluoropyridin-3-yl)-8,8-dimethyl-7H-purino[8,9-b][1,3]oxazol-4-yl]amino]ethyl]-2-(3-methoxyphenyl)phenol To a solution of 2-(5-fluoropyridin-3-yl)-N-[2-[3-(3-methoxyphenyl)-4-phenylmethoxyphenyl]ethyl]-8,8-dimethyl-7H-purino[8,9-b][1,3]oxazole-4-amine (102 mg) in THF/EtOH (2 ml) was added palladium hydroxide-carrying carbon (102 mg), and the mixture was stirred at room temperature for 3 hours under hydrogen atmosphere. Thereto was added AcOH (0.5 ml), and the mixture was further stirred for 3 hours. The reaction mixture was filtered, the filtrate was concentrated, and the residue was then purified by column chromatography (Hexane/AcOEt). The product was crystallized with EtOH/water to obtain the object compound (52.1 mg).

Example 17

Synthesis of 3-[5-[2-[[2-(5-fluoropyridin-3-yl)-8,8-dimethyl-7H-purino[8,9-b][1,3]oxazol-4-yl]amino]ethyl]-2-hydroxyphenyl]benzonitrile A mixture of 3-[2-hydroxy-5-[2-[(2-iodo-8,8-dimethyl-7H-purino[8,9-b][1,3]oxazol-4-yl)amino]eth yl]phenyl]benzonitrile (244 mg), 5-fluoropyridine-3-boronic acid (93 mg), Pd(dppf)Cl$_2$-DCM (18.0 mg), K$_3$PO$_4$ (188 mg), and 1,4-dioxane/water (4/1) (1 ml) was stirred at 90° C. for 3 hours under nitrogen atmosphere. The reaction mixture was purified by column chromatography (Hexane/AcOEt). The product was washed with Hexane/AcOEt to obtain the object compound (197 mg).

Example 19

Synthesis of 4-[2-[[2-(5-fluoropyridin-3-yl)-8,8-dimethyl-7H-purino[8,9-b][1,3]oxazol-4-yl]amino]ethyl]-2-(4-hydroxyphenyl)phenol A mixture of 2-(4-hydroxyphenyl)-4-[2-[(2-iodo-8,8-dimethyl-7H-purino[8,9-b][1,3]oxazol-4-yl)amino]ethyl]phenol (70.0 mg), 5-fluoropyridine-3-boronic acid (27.2 mg), Pd(dppf)Cl$_2$ DCM (5.3 mg), K$_3$PO$_4$ (54.7 mg), and 1,4-dioxane/water (4/1) (1 ml) was stirred at 90° C. for 2 hours under nitrogen atmosphere. Thereto were added water and N-acetyl-L-cysteine (21.0 mg), the mixture was allowed to cool to room temperature, and the solid precipitate was collected by filtration to obtain the object compound (58.2 mg).

Example 32

Synthesis of 4-[2-[[2-(5-fluoropyridin-3-yl)-8,8-dimethyl-7H-purino[8,9-b][1,3]oxazol-4-yl]amino]ethyl]-2-pyridin-3-ylphenol A mixture of 4-[2-[(2-iodo-8,8-dimethyl-7H-purino[8,9-b][1,3]oxazol-4-yl)amino]ethyl]-2-pyridin-3-ylphenol (88.8 mg), 5-fluoropyridine-3-boronic acid (35.5 mg), Pd(dppf)Cl$_2$'DCM (6.9 mg), K$_3$PO$_4$ (71.4 mg), and 1,4-dioxane/water (4/1) (1 ml) was stirred at 90° C. for 2 hours under nitrogen atmosphere. The reaction mixture was purified by column chromatography (Hexane/AcOEt/MeOH). The product was washed with EtOH/water and then dissolved in DME, thereto was added 2,4,6-mercaptotriazine-carrying silica gel, and the mixture was stirred at room temperature for 1 hour. The insoluble substance was removed by filtration, and the filtrate was concentrated. The residue was washed with Hexane to obtain the object compound (2.2 mg).

Example 43

Synthesis of 2-(5-fluoropyridin-3-yl)-4-[2-[[2-(5-fluoropyridin-3-yl)-8,8-dimethyl-7H-purino[8,9-b][1,3]oxazol-4-yl]amino]ethyl]phenol A mixture of 2-(5-fluoropyridin-3-yl)-4-[2-[(2-iodo-8,8-dimethyl-7H-purino[8,9-b][1,3]oxazol-4-yl) amino]ethyl] phenol (82.6 mg), 5-fluoropyridine-3-boronic acid (32.0 mg), Pd(dppf)Cl$_2$ DCM (6.2 mg), K$_3$PO$_4$ (64.2 mg), and 1,4-dioxane/water (4/1) (1.5 ml) was stirred at 90° C. for 2 hours under nitrogen atmosphere. The reaction mixture was purified by column chromatography (Hexane/AcOEt). The product was washed with Hexane/AcOEt to obtain the object compound (62.9 mg).

Example 46

Synthesis of 5-[4-[2-(4-hydroxy-3-phenylphenyl)ethylamino]-8,8-dimethyl-7H-purino[8,9-b][1,3]oxazol-2-yl]pyridine-3-carbonitrile Under nitrogen atmosphere, a mixture of 4-[2-[(2-iodo-8,8-dimethyl-7H-purino[8,9-b][1,3]oxazol-4-yl)amino]ethyl]-2-phenylphenol (84.0 mg), 5-cyanopyridine-3-boronic acid (35.3 mg), Pd(dppf)Cl$_2$DCM (13.0 mg), K$_3$PO$_4$ (67.6 mg), and DME/water (4/1) (3 ml) was stirred under reflux with heating for 5 hours. The reaction mixture was filtered through Celite, and the filtrate was concentrated. The product was washed with MeOH/AcOEt to obtain the object compound (44.6 mg).

Example 62

Synthesis of 3-[5-[2-[[2-[5-(difluoromethyl)pyridin-3-yl]-8,8-dimethyl-7H-purino[8,9-b][1,3]oxazol-4-yl]amino]ethyl]-2-hydroxyphenyl]benzonitrile A mixture of 5-difluoromethylpyridine-3-bromide (56.5 mg), bispinacol diborane (83.0 mg), Pd(dppf)Cl$_2$-DCM (29.6 mg), AcOK (71.1 mg), and 1,4-dioxane (4 ml) was stirred at 100° C. for 2 hours under nitrogen atmosphere. The mixture was cooled to room temperature, thereto were then added 3-[2-hydroxy-5-[2-[(2-iodo-8,8-dimethyl-7H-purino[8,9-b][1,3]oxazol-4-yl)amino]eth yl]phenyl]benzonitrile (100 mg), Pd(dppf)Cl$_2$-DCM (14.8 mg), K$_3$PO$_4$ (77.0 mg), and water (1 ml), and the mixture was stirred at 100° C. for 16 hours. The reaction mixture was filtered through Celite, the filtrate was concentrated, and the residue was then purified by column chromatography (Hexane/AcOEt). The product was washed with DCM/hexane to obtain the object compound (63.2 mg).

Example 121

Synthesis of 2-cyclohexyl-N-[2-(1H-indol-3-yl)ethyl]-8,8-dimethyl-7H-purino[8,9-b][1,3]oxazole-4-amine To a solution of 2-(cyclohexen-1-yl)-N-[2-(1H-indol-3-yl)ethyl]-8,8-dimethyl-7H-purino[8,9-b][1,3]ox azole-4- amine (30 mg) in THF/EtOH (1/1) (2 ml) was added palladium hydroxide-carrying carbon (15 mg), and the mixture was stirred at room temperature for 5 hours under hydrogen atmosphere. The reaction mixture was filtered, the filtrate was concentrated, and the residue was then purified by column chromatography (Hexane/AcOEt). The product was washed with Hexane/AcOEt to obtain the object compound (21 mg).

Example 127

Synthesis of 2-bromo-4-[2-[[2-(5-fluoropyridin-3-yl)-8,8-dimethyl-7H-purino[8,9-b][1,3]oxazol-4-yl]amino]ethyl]phenol To a solution of 4-[2-[[2-(5-fluoropyridin-3-yl)-8,8-dimethyl-7H-purino[8,9-b][1,3]oxazol-4-yl]amino]ethyl]phenol (388 mg) in DMF (10 ml) was added NBS (181 mg) at 0° C., and the mixture was stirred at 0° C. for 1 hour. Thereafter, NBS (57 mg) was added in portions thereto, and the mixture was stirred overnight. To the reaction mixture was added water, and the mixture was extracted with AcOEt. The organic layer was washed with water and saturated saline, dried with anhydrous sodium sulfate and filtered, and the filtrate was concentrated. The residue was purified by column chromatography (Hexane/AcOEt) to obtain the object compound (155 mg).

Example 139

Synthesis of N-[2-(1H-indol-3-yl)ethyl]-8,8-dimethyl-2-[5-(methylamino)pyridin-3-yl]-7H-purino[8,9-b][1,3]oxazole-4-amine To a suspension of tert-butyl N-[5-[4-[2-(1H-indol-3-yl)ethylamino]-8,8-dimethyl-7H-purino[8,9-b][1,3]oxazol-2-yl]pyridin-3-yl]-N-methylcarbamate (55 mg) in MeCN (3 ml) were added sodium iodide (74.3 mg) and trimethylsilyl chloride (0.051 ml), and the mixture was stirred at room temperature for 16 hours. To the reaction mixture was added water, and the mixture was extracted with AcOEt. The organic layer was washed with water, dried with anhydrous sodium sulfate and filtered, and the filtrate was concentrated. To the residue was added MeCN (3 ml), thereto was added silver carbonate (54.7 mg) at 0° C., and the mixture was stirred at 80° C. for 2 hours. The insoluble substance was filtered, the filtrate was concentrated, and the residue was then purified by column chromatography (Hexane/AcOEt). The obtained solid was washed with DCM/Hexane to obtain the object compound (13.7 mg).

The compounds of Examples 3 to 12, 14 to 16, 18, 20 to 31, 33 to 42, 44 to 45, 47 to 61, 63 to 120, 122 to 126, 128 to 138, and 140 to 146 were manufactured in the same manner as in Examples 1, 2, 13, 17, 19, 32, 43, 46, 62, 121, 127 and 139. Structural formulae and physicochemical data of the compounds of Examples 1 to 146 are shown in Tables 2-1 to 2-34.

TABLE 2-1

| EX | STR | Prop | Data |
| --- | --- | --- | --- |
| 1 | | 1 | NMR1 (500 MHz); 9.35 (1H, s), 9.30 (1H, s), 8.63 (1H, d, J = 2.8 Hz), 8.39-8.32 (1H, m), 7.54 (1H, s), 7.51-7.46 (2H, m), 7.37-7.30 (2H, m), 7.29-7.22 (1H, m), 7.15 (1H, d, J = 2.2 Hz), 7.06 (1H, dd, J = 8.2, 2.3 Hz), 6.85 (1H, d, J = 8.2 Hz), 4.91 (2H, s), 3.78 (2H, s), 2.89 (2H, t, J = 7.3 Hz), 1.71 (6H, s). |
| 2 | | 2 | NMR1 (500 MHz); 9.37-9.31 (2H, m), 8.62 (1H, d, J = 2.8 Hz), 8.38-8.31 (1H, m), 7.53 (1H, s), 7.39-7.31 (1H, m), 7.31-7.25 (1H, m), 7.21-7.10 (3H, m), 7.10-7.03 (1H, m), 6.84 (1H, d, J = 8.2 Hz), 4.91 (2H, s), 3.77 (2H, s), 2.88 (2H, t, J = 7.4 Hz), 1.71 (6H, s). |
| 3 | | 1 | NMR1 (500 MHz); 9.46 (1H, s), 9.34 (1H, s), 8.62 (1H, d, J = 2.9 Hz), 8.37-8.31 (1H, m), 7.54 (1H, s), 7.40-7.25 (3H, m), 7.21-7.17 (1H, m), 7.13-7.05 (2H, m), 6.85 (1H, d, J = 8.2 Hz), 4.91 (2H, s), 3.79 (2H, s), 2.89 (2H, t, J = 7.2 Hz), 1.71 (6H, s). |

TABLE 2-1-continued

| EX | STR | Prop | Data |
| --- | --- | --- | --- |
| 4 | | 1 | NMR1 (500 MHz); 9.38 (1H, s), 9.35 (1H, s), 8.63 (1H, d, J = 2.9 Hz), 8.38-8.32 (1H, m), 7.56-7.49 (3H, m), 7.20-7.11 (3H, m), 7.06 (1H, dd, J = 8.2, 2.2 Hz), 6.85 (1H, d, J = 8.2 Hz), 4.91 (2H, s), 3.78 (2H, s), 2.88 (2H, t, J = 7.4 Hz), 1.71 (6H, s). |

TABLE 2-2

| EX | STR | Prop | Data |
| --- | --- | --- | --- |
| 5 | | 17 | NMR1 (500 MHz); 9.35-9.31 (1H, m), 9.27 (1H, s), 8.61 (1H, d, J = 2.8 Hz), 8.36-8.30 (1H, m), 7.51 (1H, s), 7.45 (1H, dd, J = 7.4, 1.7 Hz), 7.35-7.20 (3H, m), 7.12 (1H, dd, J = 8.3, 2.3 Hz), 6.98 (1H, d, J = 2.3 Hz), 6.83 (1H, d, J = 8.2 Hz), 4.91 (2H, s), 3.77 (2H, s), 2.91-2.84 (2H, m), 1.71 (6H, s). |
| 6 | | 17 | NMR1 (500 MHz); 9.47 (1H, s), 9.34 (1H, s), 8.62 (1H, d, J = 2.9 Hz), 8.39-8.30 (1H, m), 7.55-7.49 (2H, m), 7.44 (1H, d, J = 7.6 Hz), 7.39-7.30 (2H, m), 7.18 (1H, d, J = 2.2 Hz), 7.10 (1H, dd, J = 8.2, 2.2 Hz), 6.85 (1H, d, J = 8.2 Hz), 4.91 (2H, s), 3.79 (2H, s), 2.89 (2H, t, J = 7.1 Hz), 1.71 (6H, s). |
| 7 | | 17 | NMR1 (500 MHz); 9.43 (1H, s), 9.35 (1H, s), 8.63 (1H, d, J = 2.9 Hz), 8.35 (1H, d, J = 9.7 Hz), 7.55-7.49 (3H, m), 7.41-7.35 (2H, m), 7.18 (1H, d, J = 2.2 Hz), 7.08 (1H, dd, J = 8.2, 2.2 Hz), 6.85 (1H, d, J = 8.2 Hz), 4.91 (2H, s), 3.78 (2H, s), 2.89 (2H, t, J = 7.2 Hz), 1.71 (6H, s). |
| 8 | | 1 | NMR1 (500 MHz); 9.35 (1H, s), 9.33 (1H, s), 8.63 (1H, d, J = 2.9 Hz), 8.38-8.32 (1H, m), 7.81 (1H, s), 7.38-7.30 (1H, m), 7.27-7.23 (1H, m), 7.21-7.10 (3H, m), 7.07 (1H, s), 6.84 (1H, d, J = 8.2 Hz), 3.90 (2H, s), 3.78 (2H, s), 2.89 (2H, t, J = 7.4 Hz), 1.78 (6H, s). |

TABLE 2-3

| EX | STR | Prop | Data |
|---|---|---|---|
| 9 | | 1 | NMR1 (500 MHz); 9.46 (1H, s), 9.35 (1H, s), 8.63 (1H, d, J = 2.9 Hz), 8.35 (1H, d, J = 10.1 Hz), 7.82 (1H, s), 7.41-7.33 (1H, m), 7.33-7.25 (2H, m), 7.21-7.17 (1H, m), 7.13-7.05 (2H, m), 6.85 (1H, d, J = 8.2 Hz), 3.90 (2H, s), 3.80 (2H, s), 2.90 (2H, t, J = 6.8 Hz), 1.77 (6H, s). |
| 10 | | 17 | NMR1 (500 MHz); 9.46 (1H, s), 9.33 (1H, s), 8.61 (1H, d, J = 2.9 Hz), 8.36-8.30 (1H, m), 7.53 (1H, s), 7.27-7.04 (5H, m), 6.85 (1H, d, J = 8.2 Hz), 4.90 (2H, s), 3.78 (2H, s), 2.88 (2H, t, J = 7.3 Hz), 1.71 (6H, s). |
| 11 | | 17 | NMR1 (500 MHz); 9.48 (1H, s), 9.33 (1H, s), 8.61 (1H, d, J = 2.9 Hz), 8.37-8.30 (1H, m), 7.53 (1H, s), 7.40-7.31 (1H, m), 7.20-7.05 (4H, m), 6.86 (1H, d, J = 8.2 Hz), 4.91 (2H, s), 3.78 (2H, s), 2.89 (2H, t, J = 7.3 Hz), 1.71 (6H, s). |
| 12 | | 17 | NMR1 (500 MHz); 9.61 (1H, s), 9.32 (1H, s), 8.61 (1H, d, J = 2.8 Hz), 8.36-8.29 (1H, m), 7.53 (1H, s), 7.25-7.07 (5H, m), 6.85 (1H, d, J = 8.2 Hz), 4.90 (2H, s), 3.79 (2H, s), 2.89 (2H, t, J = 7.1 Hz), 1.71 (6H, s). |
| 13 | | 13 | NMR1 (500 MHz); 9.34 (1H, s), 9.29 (1H, s), 8.62 (1H, d, J = 2.9 Hz), 8.38-8.31 (1H, m), 7.52 (1H, s), 7.24 (1H, t, J = 8.2 Hz), 7.15 (1H, d, J = 2.3 Hz), 7.10-7.01 (3H, m), 6.87-6.81 (2H, m), 4.91 (2H, s) 3.87-3.70 (5H, m), 2.89 (2H, t, J = 7.3 Hz), 1.71 (6H, s). |

TABLE 2-4

| EX | STR | Prop | Data |
|---|---|---|---|
| 14 | | 17 | NMR1 (500 MHz); 9.35 (1H, s), 9.24 (1H, s), 8.62 (1H, d, J = 2.8 Hz), 8.38-8.32 (1H, m), 7.53 (1H, s), 7.30-7.25 (2H, m), 7.21 (1H, t, J = 7.8 Hz), 7.15-7.11 (1H, m), 7.10-7.02 (2H, m), 6.83 (1H, d, J = 8.1 Hz), 4.91 (2H, s), 3.78 (2H, s), 2.89 (2H, t, J = 7.2 Hz), 2.31 (3H, s), 1.71 (6H, s). |
| 15 | | 17 | NMR1 (500 MHz); 9.35 (1H, s), 9.25 (1H, s), 8.62 (1H, d, J = 2.9 Hz), 8.38-8.32 (1H, m), 7.53 (1H, s), 7.32-7.27 (2H, m), 7.24 (1H, t, J = 7.8 Hz), 7.14 (1H, d, J = 2.3 Hz), 7.12-7.08 (1H, m), 7.05 (1H, dd, J = 8.2, 2.3 Hz), 6.84 (1H, d, J = 8.1 Hz), 4.91 (2H, s), 3.78 (2H, s), 2.89 (2H, t, J = 7.2 Hz), 2.60 (2H, q, J = 7.6 Hz), 1.71 (6H, s), 1.18 (3H, t, J = 7.6 Hz). |
| 16 | | 17 | NMR1 (500 MHz); 9.54 (1H, s), 9.33 (1H, s), 8.61 (1H, d, J = 2.8 Hz), 8.36-8.30 (1H, m), 7.82 (1H, s), 7.78 (1H, d, J = 7.7 Hz), 7.66-7.50 (3H, m), 7.23 (1H, s), 7.12 (1H, dd, J = 8.3, 2.2 Hz), 6.88 (1H, d, J = 8.2 Hz), 4.91 (2H, s), 3.80 (2H, s), 2.91 (2H, t, J = 7.2 Hz), 1.71 (6H, s). |
| 17 | | 17 | NMR1 (500 MHz); 9.58 (1H, s), 9.34 (1H, s), 8.61 (1H, d, J = 2.9 Hz), 8.37-8.30 (1H, m), 7.90 (1H, s), 7.84 (1H, d, J = 7.9 Hz), 7.73 (1H, dt, J = 7.8, 1.4 Hz), 7.59-7.52 (2H, m), 7.24 (1H, s), 7.12 (1H, dd, J = 8.2, 2.2 Hz), 6.87 (1H, d, J = 8.2 Hz), 4.91 (2H, s), 3.79 (2H, s), 2.90 (2H, t, J = 7.2 Hz), 1.71 (6H, s). |

TABLE 2-5

| EX | STR | Prop | Data |
|---|---|---|---|
| 18 | | 17 | NMR1 (500 MHz); 9.64 (1H, s), 9.35 (1H, s), 8.64 (1H, d, J = 2.9 Hz), 8.35 (1H, d, J = 9.9 Hz), 7.80 (2H, d, J = 8.4 Hz), 7.72 (2H, d, J = 8.3 Hz), 7.55 (1H, s), 7.24 (1H, d, J = 2.2 Hz), 7.14 (1H, dd, J = 8.3, 2.2 Hz), 6.88 (1H, d, J = 8.3 Hz), 4.92 (2H, s), 3.80 (2H, s), 2.90 (2H, t, J = 7.3 Hz), 1.71 (6H, s). |

TABLE 2-5-continued

| EX | STR | Prop | Data |
|---|---|---|---|
| 19 | | 19 | NMR1 (500 MHz); 9.40-9.32 (2H, m), 9.15 (1H, s), 8.63 (1H, d, J = 2.9 Hz), 8.36 (1H, d, J = 10.1 Hz), 7.52 (1H, s), 7.30 (2H, d, J = 8.4 Hz), 7.09 (1H, s), 6.99 (1H, dd, J = 8.1, 2.2 Hz), 6.60 (1H, d, J = 8.1 Hz), 6.72 (2H, d, J = 8.5 Hz), 4.91 (2H, s), 3.76 (2H, s), 2.87 (2H, t, J = 7.4 Hz), 1.71 (6H, s). |
| 20 | | 1 | NMR1 (500 MHz) 9.40 (1H, s), 9.35 (1H, s) 8.68 (1H, d, J = 2.9 Hz), 8.54 (1H, t, J = 5.8 Hz), 8.45-8.38 (1H, m), 7.37-7.29 (1H, m), 7.25-7.11 (4H, m), 7.10-7.06 (1H, m), 6.83 (1H, d, J = 8.2 Hz), 3.97 (1H, d, J = 14.2 Hz), 3.93-3.79 (3H, m), 2.94 (2H, t, J = 7.1 Hz), 1.93 (3H, s), 1.88 (3H, s). |
| 21 | | 1 | NMR1 (500 MHz); 9.46 (1H, s), 9.40 (1H, s), 8.68 (1H, d, J = 2.9 Hz), 8.54 (1H, t, J = 5.7 Hz), 8.42 (1H, s), 7.40-7.33 (1H, m), 7.36-7.24 (2H, m), 7.24-7.20 (1H, m), 7.13-7.04 (2H, m), 6.84 (1H, d, J = 8.2 Hz), 3.96 (1H, d, J = 14.2 Hz), 3.91-3.81 (3H, m), 2.95 (2H, t, J = 7.1 Hz), 1.93 (3H, s), 1.88 (3H, s). |

TABLE 2-6

| EX | STR | Prop | Data |
|---|---|---|---|
| 22 | | 1 | NMR1 (500 MHz); 9.32 (1H, s), 9.30 (1H, s), 8.47-8.42 (1H, m), 8.40 (1H, s), 7.54-7.48 (2H, m), 7.45 (1H, s), 7.37-7.31 (2H, m), 7.30-7.23 (1H, m), 7.16 (1H, d, J = 2.2 Hz), 7.08 (1H, dd, J = 8.1, 2.2 Hz), 6.86 (1H, d, J = 8.2 Hz), 4.90 (2H, s), 3.77 (2H, s), 2.89 (2H, t, J = 7.4 Hz), 2.34 (3H, s), 1.71 (6H, s). |

TABLE 2-6-continued

| EX | STR | Prop | Data |
|---|---|---|---|
| 23 | | 1 | NMR1 (500 MHz); 9.37 (1H, s), 9.28 (1H, s), 8.46-8.42 (1H, m), 8.39 (1H, s), 7.46 (1H, s), 7.38-7.28 (2H, m), 7.24-7.11 (3H, m), 7.08 (1H, d, J = 2.2 Hz), 6.86 (1H, d, J = 8.2 Hz), 4.90 (2H, s), 3.75 (2H, s), 2.88 (2H, t, J = 7.5 Hz), 2.32 (3H, s), 1.71 (6H, s). |
| 24 | | 1 | NMR1 (500 MHz); 9.48 (1H, s), 9.28 (1H, s), 8.46-8.42 (1H, m), 8.39 (1H, s), 7.45 (1H, s), 7.42-7.27 (3H, m), 7.20 (1H, d, J = 2.2 Hz), 7.14-7.06 (2H, m), 6.87 (1H, d, J = 8.2 Hz), 4.90 (2H, s), 3.78 (2H, s), 2.90 (2H, t, J = 7.4 Hz), 2.34 (3H, s), 1.71 (6H, s). |
| 25 | | 1 | NMR1 (500 MHz); 9.41 (1H, s), 9.29 (1H, s), 8.45 (1H, d, J = 2.2 Hz), 8.39 (1H, s), 7.58-7.50 (2H, m), 7.45 (1H, s), 7.20-7.12 (3H, m), 7.07 (1H, dd, J = 8.2, 2.2 Hz), 6.86 (1H, d, J = 8.1 Hz), 4.90 (2H, s), 3.77 (2H, s), 2.89 (2H, t, J = 7.4 Hz), 2.34 (3H, s), 1.71 (6H, s). |

TABLE 2-7

| EX | STR | Prop | Data |
|---|---|---|---|
| 26 | | 1 | NMR1 (500 MHz); 9.35 (1H, s), 9.29 (1H, s), 8.45 (1H, s), 8.40 (1H, s), 7.74 (1H, s), 7.39-7.32 (1H, m), 7.28 (1H, t, J = 7.8 Hz), 7.23-7.11 (3H, m), 7.08 (1H, s), 6.86 (1H, d, J = 8.2 Hz), 3.89 (2H, s), 3.76 (2H, s), 2.89 (2H, t, J = 7.5 Hz), 2.32 (3H, s), 1.78 (6H, s). |

TABLE 2-7-continued

| EX | STR | Prop | Data |
|---|---|---|---|
| 27 | | 1 | NMR1 (500 MHz); 9.48 (1H, s), 9.30 (1H, s), 8.45 (1H, d, J = 2.2 Hz), 8.40 (1H, s), 7.73 (1H, s), 7.41-7.27 (3H, m), 7.20 (1H, s), 7.13-7.06 (2H, m), 6.87 (1H, d, J = 8.2 Hz), 3.89 (2H, s), 3.78 (2H, s), 2.91 (2H, t, J = 7.4 Hz), 2.34 (3H, s), 1.78 (6H, s). |
| 28 | chiral | 1 | NMR1 (500 MHz); 9.34 (2H, s), 8.63 (1H, d, J = 2.9 Hz), 8.37-8.30 (1H, m), 7.82 (1H, s), 7.38-7.30 (1H, m), 7.27-7.23 (1H, m), 7.21-7.09 (3H, m), 7.07 (1H, s), 6.83 (1H, d, J = 8.2 Hz), 4.95-4.85 (1H, m), 4.20 (1H, dd, J = 11.2, 7.1 Hz), 3.79 (2H, s), 3.71 (1H, dd, J = 11.1, 6.1 Hz), 2.89 (2H, t, J = 7.3 Hz), 1.67 (3H, d, J = 6.3 Hz). |
| 29 | chiral | 1 | NMR1 (400 MHz); 9.47 (1H, s), 9.34 (1H, s), 8.63 (1H, d, J = 2.9 Hz), 8.34 (1H, d, J = 10.1 Hz), 7.81 (1H, s), 7.42-7.23 (3H, m), 7.19 (1H, s), 7.13-7.04 (2H, m), 6.85 (1H, d, J = 8.2 Hz), 4.94-4.85 (1H, m), 4.20 (1H, dd, J = 11.2, 7.1 Hz), 3.81 (2H, s), 3.71 (1H, dd, J = 11.3, 6.1 Hz), 2.98-2.83 (2H, m), 1.67 (3H, d, J = 6.3 Hz). |

TABLE 2-8

| EX | STR | Prop | Data |
|---|---|---|---|
| 30 | chiral | 1 | NMR1 (500 MHz); 9.34 (2H, s), 8.63 (1H, d, J = 2.9 Hz), 8.37-8.30 (1H, m), 7.82 (1H, s), 7.38-7.30 (1H, m), 7.27-7.23 (1H, m), 7.21-7.09 (3H, m), 7.07 (1H, s), 6.84 (1H, d, J = 8.2 Hz), 4.95-4.85 (1H, m), 4.20 (1H, dd, J = 11.2, 7.1 Hz), 3.79 (2H, s), 3.71 (1H, dd, J = 11.2, 6.1 Hz), 2.90 (2H, t, J = 7.4 Hz), 1.67 (3H, d, J = 6.4 Hz). |

TABLE 2-8-continued

| EX | STR | Prop | Data |
|---|---|---|---|
| 31 | (chiral) | 1 | NMR1 (500 MHz); 9.47 (1H, s), 9.34 (1H, s), 8.63 (1H, d, J = 2.9 Hz), 8.37-8.31 (1H, m), 7.82 (1H, s), 7.41-7.23 (3H, m), 7.19 (1H, s), 7.13-7.05 (2H, m), 6.85 (1H, d, J = 8.2 Hz), 4.94-4.84 (1H, m), 4.20 (1H, dd, J = 11.2, 7.1 Hz), 3.80 (2H, s), 3.71 (1H, dd, J = 11.2, 6.1 Hz), 2.91 (2H, t, J = 7.1 Hz), 1.67 (3H, d, J = 6.4 Hz). |
| 32 | | 32 | NMR1 (500 MHz); 9.54 (1H, s), 9.33 (1H, s), 8.68-8.60 (2H, m), 8.46 (1H, dd, J = 4.7, 1.7 Hz), 8.37-8.31 (1H, m), 7.90-7.84 (1H, m), 7.54 (1H, s), 7.37 (1H, dd, J = 7.9, 4.7 Hz), 7.20 (1H, s), 7.12 (1H, dd, J = 8.2, 2.3 Hz), 6.87 (1H, d, J = 8.2 Hz), 4.91 (2H, s), 3.79 (2H, s), 2.90 (2H, t, J = 7.2 Hz), 1.71 (6H, s). |
| 33 | | 17 | NMR1 (500 MHz); 9.95 (1H, s), 9.36 (1H, s), 8.63 (1H, d, J = 2.9 Hz), 8.37 (1H, d, J = 9.8 Hz), 7.58-7.48 (3H, m), 7.45 (1H, dd, J = 5.1, 1.2 Hz), 7.09-7.01 (2H, m), 6.85 (1H, d, J = 8.2 Hz), 4.91 (2H, s), 3.79 (2H, s), 2.89 (2H, t, J = 7.4 Hz), 1.71 (6H, s). |

TABLE 2-9

| EX | STR | Prop | Data |
|---|---|---|---|
| 34 | | 17 | NMR1 (500 MHz); 9.55 (1H, s), 9.36 (1H, s), 8.63 (1H, d, J = 2.9 Hz), 8.37 (1H, d, J = 9.8 Hz), 7.77-7.72 (1H, m), 7.59-7.47 (3H, m), 7.40 (1H, s), 7.02 (1H, dd, J = 8.2, 2.2 Hz), 6.84 (1H, d, J = 8.2 Hz), 4.91 (2H, s), 3.78 (2H, s), 2.88 (2H, t, J = 7.4 Hz), 1.71 (6H, s). |

TABLE 2-9-continued

| EX | STR | Prop | Data |
|---|---|---|---|
| 35 | | 17 | NMR1 (500 MHz); 9.36-9.31 (2H, m), 8.61 (1H, d, J = 2.9 Hz), 8.36-8.30 (1H, m), 8.03-7.96 (1H, m), 7.61-7.50 (3H, m), 7.38-7.31 (1H, m), 7.28 (1H, t, J = 7.4 Hz), 7.20-7.14 (2H, m), 6.92 (1H, d, J = 8.0 Hz), 4.91 (2H, s), 3.80 (2H, s), 2.91 (2H, t, J = 7.3 Hz), 1.71 (6H, s). |
| 36 | | 1 | NMR1 (500 MHz); 9.66 (1H, d, J = 2.1 Hz), 9.46 (1H, s), 9.05 (1H, d, J = 2.0 Hz), 8.94 (1H, s), 7.57 (1H, s), 7.43-7.21 (3H, m), 7.18 (1H, s), 7.13-7.04 (2H, m), 6.85 (1H, d, J = 8.1 Hz), 4.91 (2H, s), 3.81 (2H, s), 2.90 (2H, t, J = 7.1 Hz), 1.72 (6H, s) |
| 37 | | 1 | NMR1 (500 MHz); 9.67 (1H, s), 9.46 (1H, s), 9.06 (1H, d, J = 2.0 Hz), 8.95 (1H, s), 7.85 (1H, s), 7.40-7.32 (1H, m), 7.30-7.21 (2H, m), 7.18 (1H, s), 7.13-7.04 (2H, m), 6.84 (1H, d, J = 8.2 Hz), 3.90 (2H, s), 3.82 (2H, s), 2.94-2.87 (2H, m), 1.78 (6H, s). |
| 38 | | 1 | NMR1 (500 MHz); 9.68 (1H, s), 9.33 (1H, s), 9.07 (1H, d, J = 2.1 Hz), 8.96 (1H, s), 7.84 (1H, s), 7.37-7.29 (1H, m), 7.25-7.11 (4H, m), 7.06 (1H, s), 6.83 (1H, d, J = 8.2 Hz), 3.91 (2H, s), 3.81 (2H, s), 2.89 (2H, t, J = 7.3 Hz), 1.79 (6H, s). |

TABLE 2-10
| EX | STR | Prop | Data |
|----|-----|------|------|
| 39 | 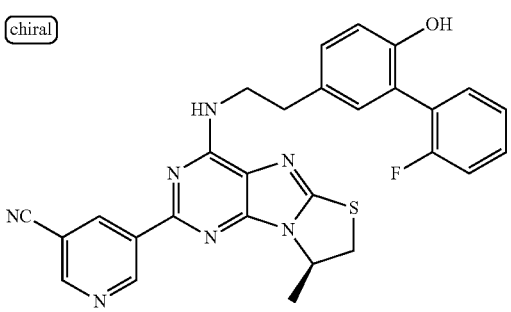 | 1 | NMR1 (500 MHz); 9.66 (1H, s), 9.32 (1H, s), 9.06 (1H, d, J = 2.1 Hz), 8.93 (1H, s), 7.84 (1H, s), 7.37-7.29 (1H, m), 7.26-7.10 (4H, m), 7.07 (1H, s), 6.83 (1H, d, J = 8.2 Hz), 4.95-4.85 (1H, m), 4.20 (1H, dd, J = 11.2, 7.1 Hz), 3.81 (2H, s), 3.71 (1H, dd, J = 11.2, 6.1 Hz), 2.90 (2H, t, J = 7.3 Hz), 1.68 (3H, d, J = 6.4 Hz). |
| 40 | 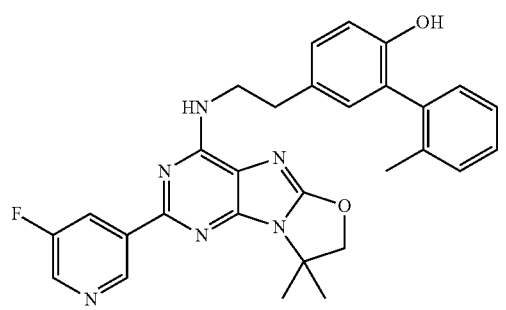 | 17 | NMR1 (500 MHz); 9.32 (1H, s), 9.12 (1H, s), 8.64-8.59 (1H, m), 8.36-8.29 (1H, m), 7.49 (1H, s), 7.20-7.06 (4H, m), 7.01 (1H, d, J = 7.4 Hz), 6.90 (1H, s), 6.81 (1H, d, J = 8.1 Hz), 4.91 (2H, s), 3.78 (2H, s), 2.87 (2H, t, J = 7.4 Hz), 2.03 (3H, s), 1.71 (6H, s). |
| 41 | 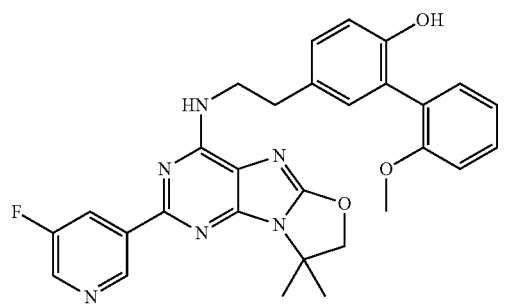 | 17 | NMR1 (500 MHz); 9.34 (1H, s), 8.90 (1H, s), 8.62 (1H, d, J = 2.7 Hz), 8.38-8.31 (1H, m), 7.51 (1H, s), 7.31-7.24 (1H, m), 7.11-6.88 (5H, m), 6.61-6.76 (1H, m), 4.91 (2H, s), 3.75 (2H, s), 3.67 (3H, s), 2.86 (2H, t, J = 7.5 Hz), 1.71 (6H, s). |
| 42 | 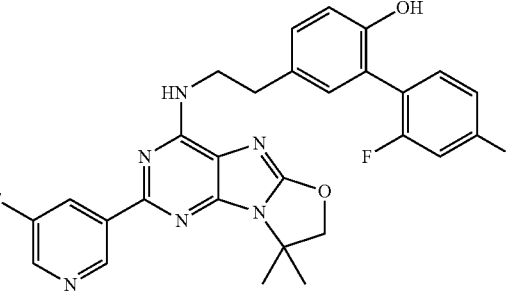 | 17 | NMR1 (500 MHz); 9.38 (1H, s), 9.34 (1H, s), 8.62 (1H, d, J = 2.8 Hz), 8.37-8.31 (1H, m), 7.53 (1H, s), 7.37-7.29 (1H, m), 7.21 (1H, td, J = 9.8, 2.6 Hz), 7.13 (1H, dd, J = 8.2, 2.3 Hz), 7.09-7.01 (2H, m), 6.64 (1H, d, J = 8.2 Hz), 4.91 (2H, s), 3.77 (2H, s), 2.91-2.64 (2H, m), 1.71 (6H, s). |

TABLE 2-11

| EX | STR | Prop | Data |
|---|---|---|---|
| 43 | | 43 | NMR1 (500 MHz); 9.69 (1H, s), 9.32 (1H, s), 8.61 (1H, d, J = 2.9 Hz), 8.56 (1H, s), 8.47 (1H, d, J = 2.8 Hz), 8.36-8.30 (1H, m), 7.80-7.74 (1H, m), 7.54 (1H, s), 7.27 (1H, s), 7.15 (1H, dd, J = 8.3, 2.2 Hz), 6.88 (1H, d, J = 8.2 Hz), 4.90 (2H, s), 3.80 (2H, s), 2.91 (2H, t, J = 7.2 Hz), 1.71 (6H, s). |
| 44 | | 1 | NMR1 (500 MHz); 9.47 (1H, s), 9.34 (1H, s), 8.61 (1H, d, J = 2.9 Hz), 8.37-8.31 (1H, m), 7.53 (1H, s), 7.46-7.36 (1H, m), 7.18 (1H, dd, J = 8.4, 2.3 Hz), 7.14-7.05 (3H, m), 6.88 (1H, d, J = 8.2 Hz), 4.91 (2H, s), 3.77 (2H, s), 2.88 (2H, t, J = 7.5 Hz), 1.71 (6H, s). |
| 45 | | 1 | NMR1 (500 MHz); 9.70-9.65 (1H, m), 9.47 (1H, s), 9.05 (1H, d, J = 2.1 Hz), 8.95 (1H, s), 7.56 (1H, s), 7.44-7.35 (1H, m), 7.18 (1H, dd, J = 8.4, 2.3 Hz), 7.11-7.04 (3H, m), 6.87 (1H, d, J = 8.3 Hz), 4.91 (2H, s), 3.79 (2H, s), 2.89 (2H, t, J = 7.4 Hz), 1.72 (6H, s). |
| 46 | | 46 | NMR2 (500 MHz); 9.79 (1H, d, J = 2.1 Hz), 8.92 (1H, t, J = 2.1 Hz), 8.87 (1H, d, J = 2.1 Hz), 7.49-7.42 (4H, m), 7.41-7.33 (1H, m), 7.15 (1H, dd, J = 8.2, 2.2 Hz), 7.11 (1H, d, J = 2.3 Hz), 6.93 (1H, d, J = 8.2 Hz), 5.54-5.50 (1H, m), 5.41 (1H, s), 4.80 (2H, s), 4.00-3.92 (2H, m), 2.97 (2H, t, J = 6.9 Hz), 1.81 (6H, s). |

TABLE 2-12
| EX | STR | Prop | Data |
|---|---|---|---|
| 47 | 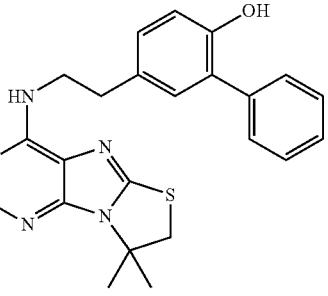 | 1 | NMR1 (500 MHz); 9.36 (1H, s), 9.30 (1H, s), 8.64 (1H, d, J = 2.9 Hz), 8.36 (1H, d, J = 10.1 Hz), 7.82 (1H, s), 7.46 (2H, d, J = 7.4 Hz), 7.33 (2H, t, J = 7.5 Hz), 7.29-7.22 (1H, m), 7.15 (1H, s), 7.06 (1H, dd, J = 8.2, 2.2 Hz), 6.84 (1H, d, J = 8.2 Hz), 3.90 (2H, s), 3.79 (2H, s), 2.90 (2H, t, J = 7.2 Hz), 1.78 (6H, s). |
| 48 | 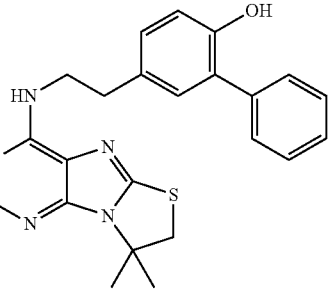 | 1 | NMR1 (500 MHz); 9.69 (1H, s), 9.28 (1H, s), 9.08 (1H, d, J = 2.1 Hz), 8.97 (1H, s), 7.85 (1H, s), 7.43 (2H, d, J = 7.3 Hz), 7.32 (2H, t, J = 7.5 Hz), 7.28-7.21 (1H, m), 7.13 (1H, s), 7.07 (1H, dd, J = 7.8, 2.2 Hz), 6.83 (1H, d, J = 8.2 Hz), 3.91 (2H, s), 3.81 (2H, s), 2.92-2.88 (2H, m), 1.78 (6H, s). |
| 49 | 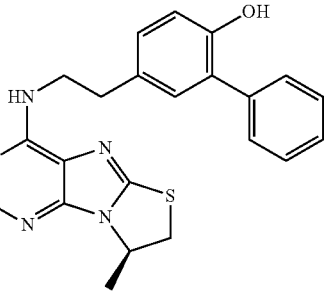 | 1 | NMR1 (500 MHz); 9.35 (1H, s), 9.29 (1H, s), 8.64 (1H, d, J = 2.9 Hz), 8.35 (1H, d, J = 10.1 Hz), 7.82 (1H, s), 7.46 (2H, d, J = 7.4 Hz), 7.33 (2H, t, J = 7.5 Hz), 7.29-7.22 (1H, m), 7.14 (1H, s), 7.06 (1H, dd, J = 8.1, 2.3 Hz), 6.83 (1H, d, J = 8.2 Hz), 4.95-4.85 (1H, m), 4.20 (1H, dd, J = 11.2, 7.1 Hz), 3.80 (2H, s), 3.71 (1H, dd, J = 11.2, 6.1 Hz), 2.90 (2H, s), 1.67 (3H, d, J = 6.4 Hz). |
| 50 | 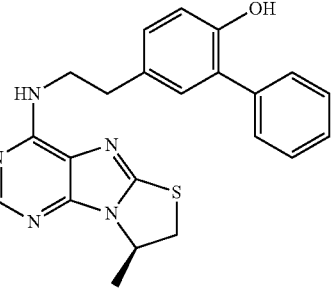 | 46 | NMR1 (500 MHz); 9.68 (1H, s), 9.27 (1H, s), 9.08 (1H, d, J = 2.1 Hz), 8.95 (1H, s), 7.86 (1H, s), 7.43 (2H, d, J = 6.9 Hz), 7.32 (2H, t, J = 7.4 Hz), 7.28-7.21 (1H, m), 7.13 (1H, s), 7.07 (1H, d, J = 8.3 Hz), 6.82 (1H, d, J = 8.2 Hz), 4.94-4.86 (1H, m), 4.21 (1H, dd, J = 11.2, 7.1 Hz), 3.82 (2H, s), 3.72 (1H, dd, J = 11.2, 6.1 Hz), 2.92-2.88 (2H, m), 1.68 (3H, d, J = 6.4 Hz). |

TABLE 2-13

| EX | STR | Prop | Data |
|---|---|---|---|
| 51 | | 1 | NMR1 (500 MHz); 9.36 (1H, s), 9.04 (1H, s), 8.64 (1H, d, J = 2.9 Hz), 8.40-8.34 (1H, m), 7.51 (1H, s), 6.99 (1H, d, J = 2.3 Hz), 6.88 (1H, dd, J =8.2, 2.2 Hz), 6.67 (1H, d, J = 8.0 Hz), 4.91 (2H, s), 3.70 (2H, s), 2.79 (2H, t, J = 7.6 Hz), 2.08 (3H, s), 1.72 (6H, s). |
| 52 | | 1 | NMR1 (500 MHz); 9.39 (1H, s), 9.31 (1H, s), 8.18-8.12 (1H, m), 8.05 (1H, s), 7.68 (1H, s), 7.63-7.54 (2H, m), 7.37-7.24 (2H, m), 7.21-7.09 (4H, m), 6.85 (1H, d, J = 8.2 Hz), 3.93-3.76 (4H, m), 2.93-2.87 (2H, m), 1.80 (6H, s). |
| 53 | | 1 | NMR1 (500 MHz); 9.47 (1H, s), 9.39 (1H, s), 8.17-8.12 (1H, m), 8.07 (1H, s), 7.68 (1H, s), 7.61-7.55 (2H, m), 7.39-7.28 (3H, m), 7.23 (1H, s), 7.15-7.05 (2H, m), 6.86 (1H, d, J = 8.1 Hz), 3.92-3.78 (9H, m), 2.91 (2H, t, J = 7.0 Hz), 1.79 (6H, s). |
| 54 | | 1 | NMR1 (500 MHz); 9.60 (1H, s), 9.33 (1H, s), 8.60 (1H, d, J = 2.9 Hz), 8.36-8.30 (1H, m), 7.91-7.84 (1H, m), 7.79 (1H, dd, J = 6.8, 2.2 Hz), 7.54 (1H, s), 7.48-7.41 (1H, m), 7.20-7.13 (2H, m), 6.86 (1H, d, J = 8.1 Hz), 4.91 (2H, s), 3.78 (2H, s), 2.89 (2H, t, J = 7.3 Hz), 1.71 (6H, s). |

TABLE 2-14

| EX | STR | Prop | Data |
|---|---|---|---|
| 55 | | 1 | NMR1 (500 MHz); 9.61 (1H, s), 9.33 (1H, s), 8.61 (1H, d, J = 2.9 Hz), 8.36-8.30 (1H, m), 7.89-7.84 (1H, m), 7.70-7.64 (1H, m), 7.57-7.51 (1H, m), 7.39 (1H, t, J = 7.7 Hz), 7.18 (1H, dd, J = 8.3, 2.2 Hz), 7.16-7.12 (1H, m), 6.87 (1H, d, J = 8.2 Hz), 4.91 (2H, s), 3.80 (2H, s), 2.90 (2H, t, J = 7.3 Hz), 1.11 (6H, s). |
| 56 | | 1 | NMR1 (500 MHz); 9.76 (1H, s), 9.32 (1H, s), 8.60 (1H, d, J = 2.9 Hz), 8.36-8.29 (1H, m), 7.80 (1H, s), 7.77-7.65 (2H, m), 7.54 (1H, s), 7.29 (1H, s), 7.14 (1H, dd, J = 8.3, 2.2 Hz), 6.87 (1H, d, J = 8.2 Hz), 4.90 (2H, s), 3.80 (2H, s), 2.90 (2H, t, J = 7.2 Hz), 1.71 (6H, s). |
| 57 | | 1 | NMR1 (500 MHz); 9.60 (1H, s), 9.35 (1H, s), 8.62 (1H, d, J = 2.8 Hz), 8.34 (1H, d, J = 10.2 Hz), 7.90 (1H, s), 7.82 (2H, d, J = 7.8 Hz), 7.76-7.70 (1H, m), 7.55 (1H, t, J = 7.8 Hz), 7.24 (1H, s), 7.12 (1H, dd, J = 8.3, 2.3 Hz), 6.86 (1H, d, J = 8.2 Hz), 3.90 (2H, s), 3.80 (2H, s), 2.91 (2H, t, J = 7.3 Hz), 1.77 (6H, s). |
| 58 | chiral | 1 | NMR1 (500 MHz); 9.58 (1H, s), 9.34 (1H, s), 8.62 (1H, d, J = 2.9 Hz), 8.33 (1H, d, J = 10.2 Hz), 7.93-7.77 (3H, m), 7.73 (1H, dt, J = 7.8, 1.4 Hz), 7.55 (1H, t, J = 7.8 Hz), 7.24 (1H, s), 7.12 (1H, dd, J = 8.3, 2.2 Hz), 6.86 (1H, d, J = 8.2 Hz), 4.94-4.84 (1H, m), 4.19 (1H, dd, J = 11.2, 7.1 Hz), 3.81 (2H, s), 3.71 (1H, dd, J = 11.1, 6.1 Hz), 2.91 (2H, t, J = 7.2 Hz), 1.67 (3H, d, J = 6.3 Hz). |

TABLE 2-15

| EX | STR | Prop | Data |
|---|---|---|---|
| 59 | | 1 | NMR1 (500 MHz); 9.66 (1H, s), 9.59 (1H, s), 9.05 (1H, d, J = 2.1 Hz), 8.94 (1H, s), 7.90-7.79 (2H, m), 7.72 (1H, dt, J = 7.8, 1.4 Hz), 7.63-7.52 (2H, m), 7.23 (1H, s), 7.13 (1H, dd, J = 8.2, 2.2 Hz), 6.86 (1H, d, J = 8.2 Hz), 4.91 (2H, s), 3.81 (2H, s), 2.90 (2H, t, J = 7. Hz), 1.71 (6H, s). |
| 60 | | 1 | NMR1 (500 MHz); 9.67 (1H, s), 9.58 (1H, s), 9.06 (1H, d, J = 2.1 Hz), 8.95 (1H, s), 7.91-7.76 (3H, m), 7.72 (1H, dt, J = 7.7, 1.4 Hz), 7.54 (1H, t, J = 7.8 Hz), 7.24 (1H, s), 7.13 (1H, dd, J = 8.2, 2.2 Hz), 6.86 (1H, d, J = 8.3 Hz), 3.90 (2H, s), 3.82 (2H, s), 2.91 (2H, t, J = 7.0 Hz), 1.78 (6H, s). |
| 61 | (chiral) | 46 | NMR1 (500 MHz); 9.66 (1H, s), 9.56 (1H, s), 9.06 (1H, d, J = 2.1 Hz), 8.93 (1H, s), 7.92-7.75 (3H, m), 7.72 (1H, d, J = 7.7 Hz), 7.54 (1H, t, J = 7.8 Hz), 7.23 (1H, s), 7.15-7.09 (1H, m), 6.85 (1H, d, J = 8.2 Hz), 4.93-4.86 (1H, m), 4.20 (1H, dd, J = 11.2, 7.1 Hz), 3.83 (2H, s), 3.71 (1H, dd, J = 11.2, 6.1 Hz), 2.95-2.89 (2H, m), 1.67 (3H, d, J = 6.3 Hz). |
| 62 | | 62 | NMR1 (500 MHz); 9.61 (2H, s), 8.82 (1H, q, J = 1.6 Hz), 8.75 (1H, s), 7.91 (1H, s), 7.84 (1H, d, J = 7.9 Hz), 7.73 (1H, dt, J = 7.7, 1.4 Hz), 7.61-7.52 (2H, m), 7.38-7.11 (3H, m), 6.88 (1H, d, J = 8.2 Hz), 4.91 (2H, s), 3.79 (2H, s), 2.91 (2H, t, J = 7.4 Hz), 1.72 (6H, s). |

TABLE 2-16

| EX | STR | Prop | Data |
|---|---|---|---|
| 63 | | 1 | NMR1 (500 MHz); 9.59 (1H, s), 9.36 (1H, s), 8.13 (1H, dd, J = 9.5, 1.7 Hz), 8.05 (1H, s), 7.95-7.91 (1H, m), 7.85 (1H, d, J = 8.0 Hz), 7.74-7.69 (1H, m), 7.61-7.50 (3H, m), 7.41-7.38 (1H, m), 7.27 (1H, s), 7.15 (1H, dd, J = 8.3, 2.2 Hz), 6.88 (1H, d, J = 8.2 Hz), 4.90 (2H, s), 3.84 (2H, s), 2.92 (2H, t, J = 7.2 Hz), 1.72 (6H, s). |
| 64 | | 1 | NMR1 (500 MHz); 9.60 (1H, s), 8.29 (1H, d, J = 5.3 Hz), 8.14 (1H, d, J = 5.2 Hz), 7.89 (1H, s), 7.86-7.81 (2H, m), 7.76-7.71 (1H, m), 7.60-7.52 (2H, m), 7.24 (1H, s), 7.12 (1H, dd, J = 8.3, 2.2 Hz), 6.87 (1H, d, J = 8.2 Hz), 4.92 (2H, s), 3.80 (2H, s), 2.90 (2H, t, J = 7.3 Hz), 1.71 (6H, s). |
| 65 | | 1 | NMR1 (500 MHz); 9.66 (1H, s), 9.56 (1H, s), 9.04 (1H, s), 8.94 (1H, s), 7.90-7.83 (1H, m), 7.75 (1H, d, J = 6.6 Hz), 7.58 (1H, s), 7.43 (1H, t, J = 9.1 Hz), 7.21-7.13 (2H, m), 6.85 (1H, d, J = 8.2 Hz), 4.91 (2H, s), 3.81 (2H, s), 2.90 (2H, t, J = 7.2 Hz), 1.72 (6H, s). |
| 66 | | 1 | NMR1 (500 MHz); 9.60 (1H, s), 9.28 (1H, s), 8.43 (1H, s), 8.39 (1H, s), 7.92-7.86 (1H, m), 7.83 (1H, dd, J = 6.8, 2.2 Hz), 7.51-7.41 (2H, m), 7.22-7.14 (2H, m), 6.88 (1H, d, J = 8.2 Hz), 4.90 (2H, s), 3.77 (2H, s), 2.90 (2H, t, J = 7.4 Hz), 2.33 (3H, s), 1.71 (6H, s). |

TABLE 2-17

| EX | STR | Prop | Data |
|----|-----|------|------|
| 67 | | 1 | NMR1 (500 MHz); 9.65 (1H, d, J = 2.1 Hz), 9.59 (1H, s), 9.04 (1H, d, J = 2.1 Hz), 8.93 (1H, t, J = 2.1 Hz), 7.85 (1H, s), 7.65 (1H, t, J = 7.2 Hz), 7.59-7.55 (1H, m), 7.37 (1H, t, J = 7.8 Hz), 7.18 (1H, dd, J = 8.3, 2.3 Hz), 7.14 (1H, d, J = 2.2 Hz), 6.86 (1H, d, J = 8.2 Hz), 4.91 (2H, s), 3.81 (2H, s), 2.90 (2H, t, J = 7.2 Hz), 1.72 (6H, s). |
| 68 | | 1 | NMR1 (500 MHz); 9.62 (1H, s), 9.27 (1H, s), 8.43 (1H, d, J = 2.2 Hz), 8.38 (1H, s), 7.90-7.84 (1H, m), 7.72-7.65 (1H, m), 7.46 (1H, s), 7.39 (1H, t, J = 7.7 Hz), 7.19 (1H, dd, J = 8.3, 2.2 Hz), 7.14 (1H, d, J = 2.2 Hz), 6.88 (1H, d, J = 8.2 Hz), 4.90 (2H, s), 3.78 (2H, s), 2.90 (2H, t, J = 7.3 Hz), 2.33 (3H, s), 1.71 (6H, s). |
| 69 | | 1 | NMR1 (500 MHz); 9.74 (1H, s), 9.65 (1H, s), 9.04 (1H, d, J = 2.1 Hz), 8.93 (1H, s), 7.77 (1H, s), 7.75-7.69 (1H, m), 7.66 (1H, d, J = 10.3 Hz), 7.58 (1H, s), 7.29 (1H, s), 7.15 (1H, dd, J = 8.2, 2.2 Hz), 6.86 (1H, d, J = 8.2 Hz), 4.91 (2H, s), 3.82 (2H, s), 2.90 (2H, t, J = 7.1 Hz), 1.71 (6H, s). |
| 70 | | 1 | NMR1 (500 MHz); 9.71 (1H, s), 9.33 (1H, s), 8.62 (1H, d, J = 2.9 Hz), 8.55 (1H, s), 8.47 (1H, d, J = 2.8 Hz), 8.34 (1H, d, J = 9.8 Hz), 7.90-7.71 (2H, m), 7.27 (1H, s), 7.15 (1H, dd, J = 8.2, 2.2 Hz), 6.87 (1H, d, J = 8.2 Hz), 3.90 (2H, s), 3.81 (2H, s), 2.92 (2H, t, J = 7.2 Hz), 1.77 (6H, s). |

TABLE 2-18

| EX | STR | Prop | Data |
|---|---|---|---|
| 71 (chiral) | | 1 | NMR1 (500 MHz); 9.69 (1H, s), 9.32 (1H, s), 8.64-8.60 (1H, m), 8.56 (1H, s), 8.49-8.45 (1H, m), 8.32 (1H, d, J = 10.1 Hz), 7.89-7.70 (2H, m), 7.28 (1H, s), 7.15 (1H, d, J = 8.3 Hz), 6.87 (1H, d, J = 8.3 Hz), 4.93-4.85 (1H, m), 4.19 (1H, dd, J = 11.3, 7.0 Hz), 3.84-3.79 (2H, m), 3.71 (1H, dd, J = 11.3, 6.1 Hz), 2.92 (2H, t, J = 7.1 Hz), 1.67 (3H, d, J = 6.3 Hz). |
| 72 | | 1 | NMR1 (500 MHz); 9.50 (1H, s), 9.33 (1H, s), 8.61 (1H, d, J = 2.9 Hz), 8.47 (1H, s), 8.38-8.28 (2H, m), 7.66 (1H, s), 7.53 (1H, s), 7.19 (1H, s) 7.11 (1H, dd, J = 8.2, 2.2 Hz), 6.86 (1H, d, J = 8.0 Hz), 4.91 (2H, s), 3.79 (2H, s), 2.90 (2H, t, J = 7.3 Hz), 2.31 (3H, s), 1.71 (6H, s). |
| 73 | | 1 | NMR1 (500 MHz); 9.48 (1H, s), 9.34 (1H, s), 8.63 (1H, d, J = 2.9 Hz), 8.46 (1H, s), 8.34 (1H, d, J = 10.1 Hz), 8.29 (1H, d, J = 2.2 Hz), 7.82 (1H, s), 7.64 (1H, s), 7.19 (1H, s), 7.11 (1H, dd, J = 8.2, 2.2 Hz), 6.85 (1H, d, J = 8.2 Hz), 3.90 (2H, s), 3.79 (2H, s), 2.91 (2H, s), 2.31 (3H, s), 1.78 (6H, s). |
| 74 (chiral) | | 1 | NMR1 (500 MHz); 9.47 (1H, s), 9.33 (1H, s), 8.62 (1H, d, J = 2.8 Hz), 8.47 (1H, s), 8.36-8.27 (2H, m), 7.82 (1H, s), 7.63 (1H, s), 7.19 (1H, s), 7.10 (1H, dd, J = 8.2, 2.3 Hz), 6.85 (1H, d, J = 8.2 Hz), 4.94-4.84 (1H, m), 4.19 (1H, dd, J = 11.2, 7.1 Hz), 3.80 (2H, s), 3.71 (1H, dd, J = 11.2, 6.1 Hz), 2.91 (2H, t, J = 7.1 Hz), 2.31 (3H, s), 1.67 (3H, d, J = 6.3 Hz). |

TABLE 2-19

| EX | STR | Prop | Data |
|---|---|---|---|
| 75 | | 17 | NMR1 (500 MHz); 9.80 (1H, s), 9.32 (1H, s), 8.99-8.95 (1H, m), 8.91 (1H, d, J = 1.9 Hz), 8.60 (1H, d, J = 2.9 Hz), 8.39-8.30 (2H, m), 7.55 (1H, s), 7.32 (1H, s), 7.17 (1H, dd, J = 8.3, 2.2 Hz), 6.89 (1H, d, J = 8.2 Hz), 4.91 (2H, s), 3.81 (2H, s), 2.91 (2H, t, J = 7.2 Hz), 1.71 (6H, s). |
| 76 | | 17 | NMR1 (500 MHz); 9.80 (1H, s), 9.33 (1H, s), 8.96 (1H, s), 8.91 (1H, d, J = 2.0 Hz), 8.62 (1H, d, J = 2.8 Hz), 8.39-8.31 (2H, m), 7.83 (1H, s), 7.33 (1H, s), 7.17 (1H, dd, J = 8.3, 2.2 Hz), 6.88 (1H, d, J = 8.2 Hz), 3.90 (2H, s), 3.82 (2H, s), 2.92 (2H, t, J = 7.2 Hz), 1.77 (6H, s). |
| 77 | (chiral) | 17 | NMR1 (500 MHz); 9.79 (1H, s), 9.32 (1H, s), 8.96 (1H, s), 8.91 (1H, d, J = 2.0 Hz), 8.61 (1H, d, J = 2.9 Hz), 8.39-8.29 (2H, m), 7.84 (1H, s), 7.33 (1H, s), 7.17 (1H, dd, J = 8.3, 2.2 Hz), 6.88 (1H, d, J = 8.2 Hz), 4.94-4.84 (1H, m), 4.19 (1H, dd, J = 11.2, 7.2 Hz), 3.82 (2H, s), 3.71 (1H, dd, J = 11.2, 6.1 Hz), 2.92 (2H, t, J = 7.2 Hz), 1.67 (3H, d, J = 6.3 Hz). |
| 78 | | 17 | NMR1 (500 MHz); 9.59 (1H, s), 9.34 (1H, s), 8.62 (1H, d, J = 2.9 Hz), 8.38-8.32 (1H, m), 8.10-8.05 (1H, m), 7.87-7.81 (2H, m), 7.63 (1H, t, J = 7.8 Hz), 7.55 (1H, s), 7.25 (1H, s), 7.14 (1H, dd, J = 8.3, 2.2 Hz), 6.89 (1H, d, J = 8.2 Hz), 4.91 (2H, s), 3.79 (2H, s), 3.23 (3H, s), 2.92 (2H, t, J = 7.8 Hz), 1.71 (6H, s). |

TABLE 2-20
| EX | STR | Prop | Data |
|---|---|---|---|
| 79 | 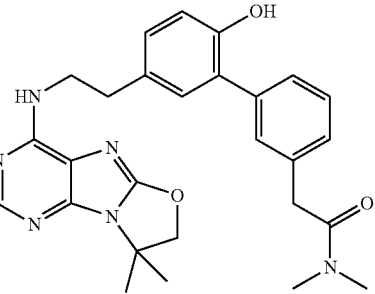 | 17 | NMR1 (500 MHz); 9.40-9.27 (2H, m), 8.66-8.61 (1H, m), 8.36 (1H, d, J = 10.1 Hz), 7.54 (1H, s), 7.40-7.33 (2H, m), 7.31-7.23 (1H, m), 7.17-7.04 (3H, m), 6.88-6.82 (1H, m), 4.91 (2H, s), 3.77 (2H, s), 3.70 (2H, d, J = 3.8 Hz), 3.03-2.98 (3H, m), 2.92-2.86 (2H, m), 2.84-2.80 (3H, m), 1.71 (6H, s). |
| 80 | 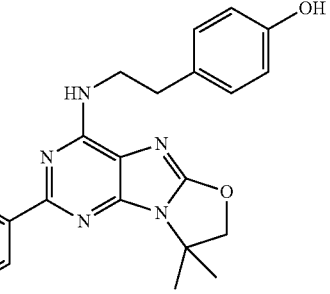 | 1 | NMR1 (500 MHz); 9.35 (1H, s), 9.16 (1H, s), 8.64 (1H, d, J = 2.9 Hz), 8.39-8.33 (1H, m), 7.50 (1H, s), 7.11-7.04 (2H, m), 6.71-6.65 (2H, m), 4.91 (2H, s), 3.71 (2H, s), 2.83 (2H, t, J = 7.5 Hz), 1.72 (6H, s). |
| 81 | 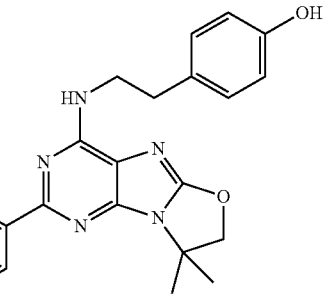 | 1 | NMR1 (500 MHz); 9.29 (1H, s), 9.17 (1H, s), 8.46 (1H, s), 8.41 (1H, s), 7.42 (1H, s), 7.12-7.05 (2H, m), 6.72-6.66 (2H, m), 4.90 (2H, s), 3.70 (2H, s), 2.83 (2H, t, J = 7.6 Hz), 2.40 (3H, s), 1.71 (6H, s). |
| 82 | 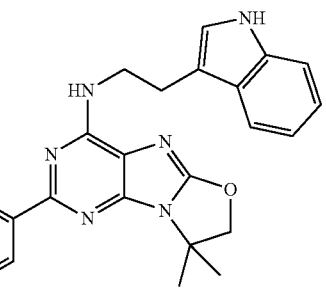 | 1 | NMR1 (500 MHz); 10.82 (1H, s), 9.37 (1H, s), 8.64 (1H, d, J = 2.9 Hz), 8.40-8.33 (1H, m), 7.65 (1H, d, J = 7.8 Hz), 7.60-7.55 (1H, m), 7.34 (1H, d, J = 8.0 Hz), 7.21 (1H, d, J = 2.3 Hz), 7.07 (1H, t, J = 7.5 Hz), 6.97 (1H, t, J = 7.4 Hz), 4.92 (2H, s), 3.85 (2H, s), 3.05 (2H, t, J = 7.7 Hz), 1.72 (6H, s). |
| 83 | 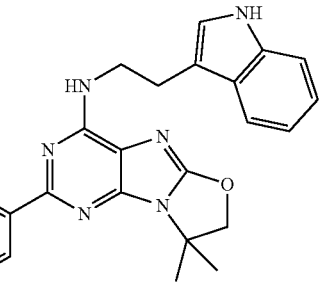 | 1 | NMR1 (500 MHz); 10.83 (1H, s), 9.31 (1H, s), 8.46 (1H, s), 8.43 (1H, s), 7.66 (1H, d, J = 7.9 Hz), 7.49 (1H, s), 7.34 (1H, dd, J = 8.1, 1.0 Hz), 7.22 (1H, d, J = 2.4 Hz), 7.11-7.04 (1H, m), 7.01-6.94 (1H, m), 4.91 (2H, s), 3.85 (2H, s), 3.05 (2H, t, J = 7.7 Hz), 2.39 (3H, s), 1.72 (6H, s). |

TABLE 2-21

| EX | STR | Prop | Data |
|---|---|---|---|
| 84 | | 1 | NMR1 (500 MHz); 10.81 (1H, s), 9.37 (1H, s), 8.63 (1H, d, J = 2.9 Hz), 8.39-8.32 (1H, m), 7.70-7.55 (2H, m), 7.33 (1H, d, J = 8.1 Hz), 7.20 (1H, d, J = 2.3 Hz), 7.10-7.04 (1H, m), 7.01-6.94 (1H, m), 4.58-4.53 (2H, m), 4.16 (2H, t, J = 6.1 Hz), 3.86 (2H, s), 3.05 (2H, t, J = 7.6 Hz), 2.29-2.20 (2H, m). |
| 85 | | 1 | NMR1 (500 MHz); 10.82 (1H, s), 8.20 (1H, d, J = 7.8 Hz), 8.08 (1H, d, J = 10.3 Hz), 7.67 (1H, d, J = 7.9 Hz), 7.54-7.42 (2H, m), 7.36-7.32 (1H, m), 7.31-7.23 (1H, m), 7.21 (1H, d, J = 2.3 Hz), 7.11-7.04 (1H, m), 7.01-6.95 (1H, m), 4.90 (2H, s), 3.85 (2H, s), 3.05 (2H, t, J = 7.7 Hz), 1.72 (6H, s). |
| 86 | | 1 | NMR1 (500 MHz); 10.79 (1H, s), 7.79 (1H, t, J = 7.3 Hz), 7.64 (1H, d, J = 7.9 Hz), 7.57-7.46 (2H, m), 7.35-7.24 (2H, m), 7.17 (1H, d, J = 2.3 Hz), 7.09-7.02 (1H, m), 6.91 (1H, t, J = 7.4 Hz), 4.91 (2H, s), 3.76 (2H, s), 3.05-2.99 (2H, m), 1.68 (6H, s). |
| 87 | | 1 | NMR1 (500 MHz); 10.79 (1H, s), 7.76 (1H, s), 7.64 (1H, d, J = 7.9 Hz), 7.52 (1H, s), 7.38-7.29 (3H, m), 7.18 (1H, d, J = 2.3 Hz), 7.09-7.02 (1H, m), 6.91 (1H, t, J = 7.4 Hz), 4.91 (2H, s), 3.76 (2H, s), 3.05-2.98 (2H, m), 1.68 (6H, s). |
| 88 | | 1 | NMR1 (500 MHz); 10.82 (1H, s), 8.29-8.21 (1H, m), 8.21-8.15 (1H, m), 7.65 (1H, d, J = 7.9 Hz), 7.56-7.44 (2H, m), 7.34 (1H, d, J = 8.1 Hz), 7.21 (1H, d, J = 2.3 Hz), 7.11-7.04 (1H, m), 7.02-6.95 (1H, m), 4.90 (2H, s), 3.84 (2H, s), 3.04 (2H, t, J = 7.7 Hz), 1.71 (6H, s). |

TABLE 2-22
| EX | STR | Prop | Data |
|---|---|---|---|
| 89 | 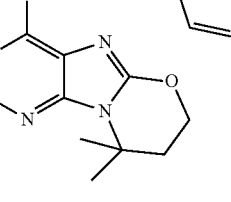 | 1 | NMR1 (500 MHz); 10.81 (1H, s), 9.38 (1H, s), 8.64 (1H, d, J = 2.9 Hz), 8.36 (1H, d, J = 10.1 Hz), 7.68-7.58 (2H, m), 7.34 (1H, d, J = 8.1 Hz), 7.21 (1H, d, J = 2.3 Hz), 7.07 (1H, t, J = 7.5 Hz), 6.97 (1H, t, J = 7.4 Hz), 4.56-4.50 (2H, m), 3.85 (2H, s), 3.04 (2H, t, J = 7.7 Hz), 2.22-2.16 (2H, m), 1.81 (6H, s). |
| 90 | 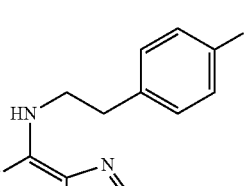 | 1 | NMR1 (500 MHz); 9.36 (1H, s), 9.18 (1H, s), 8.63 (1H, d, J = 2.9 Hz), 8.38-8.32 (1H, m), 7.53 (1H, s), 7.11-7.04 (2H, m), 6.71-6.65 (2H, m), 4.55-4.50 (2H, m), 3.71 (2H, s), 2.83 (2H, t, J = 7.5 Hz), 2.22-2.16 (2H, m), 1.81 (6H, s). |
| 91 | 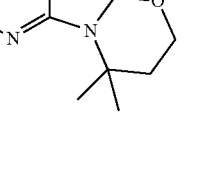 | 1 | NMR1 (500 MHz); 10.82 (1H, s), 8.53 (1H, s), 8.37 (1H, d, J = 10.1 Hz), 7.93 (1H, d, J = 8.1 Hz), 7.65 (1H, d, J = 7.7 Hz), 7.60 (1H, s), 7.33 (1H, d, J = 8.1 Hz), 7.20 (1H, s), 7.07 (1H, t, J = 7.5 Hz), 7.00 (1H, t, J = 7.5 Hz), 4.92 (2H, s), 3.85 (2H, s), 3.04 (2H, t, J = 7.7 Hz), 1.73 (6H, s). |
| 92 | 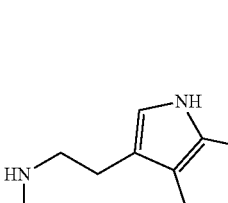 | 1 | NMR1 (500 MHz); 10.81 (1H, s), 9.70 (1H, s), 9.08 (1H, d, J = 2.1 Hz), 8.95 (1H, t, J = 2.1 Hz), 7.67-7.62 (2H, m), 7.36-7.30 (1H, m), 3.21 (1H, d, J = 2.3 Hz), 7.10-7.03 (1H, m), 7.03-6.96 (1H, m), 4.92 (2H, s), 3.86 (2H, s), 3.05 (2H, t, J = 7.6 Hz), 1.73 (6H, s). |

TABLE 2-23

| EX | STR | Prop | Data |
|---|---|---|---|
| 93 | | 1 | NMR1 (500 MHz); 10.82 (1H, s), 9.45-9.41 (1H, m), 8.69 (1H, d, J = 2.4 Hz), 8.62 (1H, t, J = 2.1 Hz), 7.70-7.53 (2H, m), 7.37-7.31 (1H, m), 7.21 (1H, d, J = 2.4 Hz), 7.10-7.03 (1H, m), 7.02-6.95 (1H, m), 4.92 (2H, s), 3.84 (2H, s), 3.05 (2H, t, J = 7.7 Hz), 1.72 (6H, s). |
| 94 | | 1 | NMR1 (500 MHz); 10.78 (1H, s), 9.49 (1H, s), 8.64-8.56 (2H, m), 7.64 (1H, d, J = 7.9 Hz), 7.51-7.45 (1H, m), 7.42 (1H, s), 7.36-7.31 (1H, m), 7.21 (1H, d, J = 2.4 Hz), 7.11-7.03 (1H, m), 7.02-6.92 (1H, m), 4.90 (2H, s), 3.87 (2H, s), 3.06 (2H, t, J = 7.7 Hz), 1.72 (6H, s). |
| 95 | | 1 | NMR1 (500 MHz); 10.82 (1H, s), 9.38 (1H, s), 8.65 (1H, d, J = 2.8 Hz), 8.41-8.34 (1H, m), 7.87 (1H, s), 7.67-7.62 (1H, m), 7.34 (1H, d, J = 8.0 Hz), 7.22 (1H, d, J = 2.4 Hz), 7.10-7.04 (1H, m), 7.01-6.94 (1H, m), 3.91 (2H, s), 3.86 (2H, s), 3.06 (2H, t, J = 7.6 Hz), 1.79 (6H, s). |
| 96 | | 1 | NMR1 (500 MHz); 10.83 (1H, s), 9.33 (1H, s), 8.49-8.45 (1H, m), 8.44 (1H, s), 7.77 (1H, s), 7.65 (1H, d, J = 7.6 Hz), 7.37-7.31 (1H, m), 7.22 (1H, d, J = 2.3 Hz), 7.11-7.04 (1H, m), 7.01-6.94 (1H, m), 3.90 (2H, s), 3.86 (2H, s), 3.06 (2H, t, J = 7.7 Hz), 2.39 (3H, s), 1.79 (6H, s). |
| 97 | | 1 | NMR1 (500 MHz); 9.36 (1H, s), 9.17 (1H, s), 8.65 (1H, d, J = 2.9 Hz), 8.37 (1H, d, J = 10.0 Hz), 7.79 (1H, s), 7.11-7.04 (2H, m), 6.71-6.65 (2H, m), 3.90 (2H, s), 3.72 (2H, s), 2.84 (2H, t, J = 7.6 Hz), 1.78 (6H, s). |

TABLE 2-24
| EX | STR | Prop | Data |
|---|---|---|---|
| 98 | 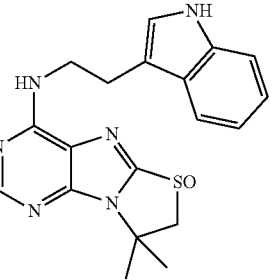 | 1 | NMR1 (500 MHz); 10.81 (1H, s), 9.43 (1H, s), 8.70 (1H, d, J = 2.8 Hz), 8.59 (1H, t, J = 5.9 Hz), 8.46-8.39 (1H, m), 7.65 (1H, d, J = 7.8 Hz), 7.33 (1H, d, J = 8.1 Hz), 7.23 (1H, d, J = 2.4 Hz), 7.07 (1H, t, J = 7.5 Hz), 6.98 (1H, t, J = 7.4 Hz), 4.00-3.89 (3H, m), 3.85 (1H, d, J = 14.2 Hz), 3.10 (2H, t, J = 7.6 Hz), 1.94 (3H, s), 1.89 (3H, s). MS m/z 476.50 (M + 1). |
| 99 | 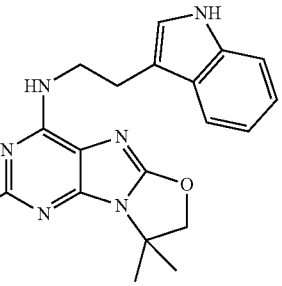 | 1 | NMR1 (500 MHz); 10.84 (1H, s), 9.46 (1H, s), 8.77 (2H, s), 7.67-7.62 (2H, m), 7.34 (1H, d, J = 8.0 Hz), 7.22 (1H, d, J = 2.4 Hz), 7.07 (1H, t, J = 7.5 Hz), 7.00 (1H, t, J = 7.4 Hz), 4.92 (2H, s), 3.83 (2H, s), 3.05 (2H, t, J = 7.7 Hz), 1.72 (6H, s). |
| 100 | 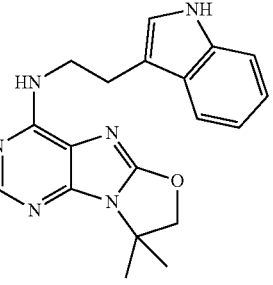 | 1 | NMR1 (500 MHz); 10.83 (1H, s), 8.34 (1H, d, J = 5.2 Hz), 8.18-8.13 (1H, m), 7.83 (1H, s), 7.72-7.60 (2H, m), 7.34 (1H, d, J = 8.0 Hz), 7.22 (1H, d, J = 2.3 Hz), 7.11-7.04 (1H, m), 7.02-6.95 (1H, m), 4.93 (2H, s), 3.85 (2H, s), 3.05 (2H, t, J = 7.6 Hz), 1.72 (6H, s). |
| 101 | 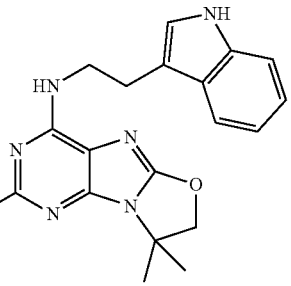 | 62 | NMR2 (500 MHz); 9.75 (1H, s), 8.81-8.75 (2H, m), 8.06 (1H, s), 7.68 (1H, d, J = 7.8 Hz), 7.41-7.34 (1H, m), 7.23-7.09 (3H, m), 6.93-6.67 (1H, m), 5.56-5.52 (1H, m), 4.78 (2H, s), 4.10-4.02 (2H, m), 3.17 (2H, t, J = 7.0 Hz), 1.81 (6H, s). |

TABLE 2-25
| EX | STR | Prop | Data |
|---|---|---|---|
| 102 | 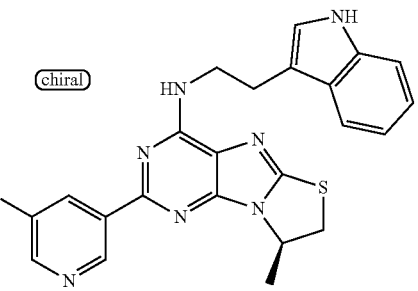 | 1 | NMR1 (500 MHz); 10.82 (1H, s), 9.37 (1H, s), 8.65 (1H, d, J = 2.9 Hz), 8.39-8.33 (1H, m), 7.87 (1H, s), 7.67-7.62 (1H, m), 7.34 (1H, d, J = 8.0 Hz), 7.21 (1H, d, J = 2.4 Hz), 7.10-7.03 (1H, m), 7.01-6.94 (1H, m), 4.96-4.86 (1H, m), 4.21 (1H, dd, J = 11.2, 7.1 Hz), 3.86 (2H, s), 3.72 (1H, dd, J = 11.2, 6.1 Hz), 3.06 (2H, t, J = 7.6 Hz), 1.68 (3H, d, J = 6.3 Hz). |
| 103 | 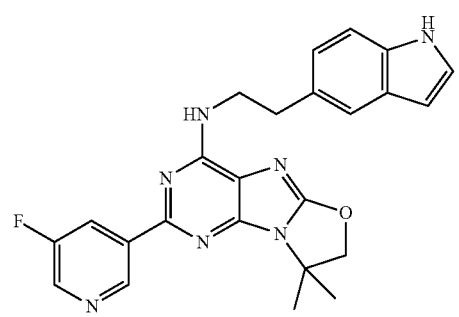 | 1 | NMR1 (500 MHz); 10.97 (1H, s), 9.38 (1H, s), 8.64 (1H, d, J = 2.9 Hz), 8.39 (1H, d, J = 10.0 Hz), 7.53 (1H, s), 7.44 (1H, s), 7.32 (1H, d, J = 8.2 Hz), 7.29 (1H, t, J = 2.8 Hz), 7.04 (1H, dd, J = 8.2, 1.7 Hz), 6.34 (1H, s), 4.91 (2H, s), 3.79 (2H, s), 3.03-2.97 (2H, m), 1.72 (6H, s). |
| 104 | 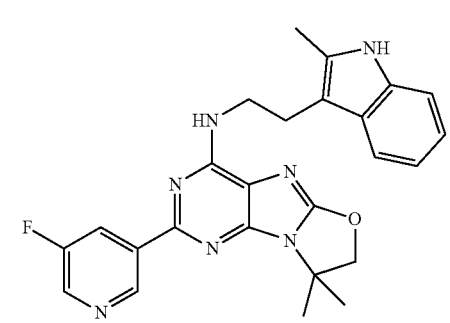 | 1 | NMR1 (500 MHz); 10.71 (1H, s), 9.37 (1H, s), 8.64 (1H, d, J = 2.8 Hz), 8.38-8.31 (1H, m), 7.57-7.52 (2H, m), 7.22 (1H, d, J = 7.8 Hz), 7.01-6.90 (2H, m), 4.92 (2H, s), 3.71 (2H, s), 3.00-2.94 (2H, m), 2.34 (3H, s), 1.73 (6H, s). |
| 105 | 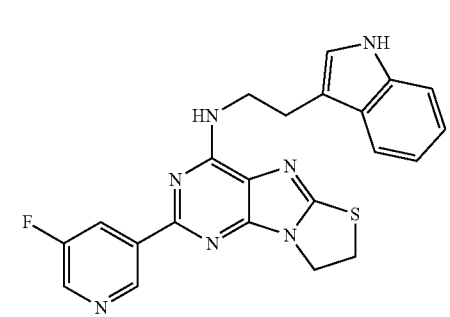 | 1 | NMR1 (500 MHz); 10.82 (1H, s), 9.37 (1H, s), 8.65 (1H, d, J = 2.8 Hz), 8.35 (1H, d, J = 10.1 Hz), 7.87 (1H, s), 7.67-7.62 (1H, m), 7.33 (1H, d, J = 8.0 Hz), 7.21 (1H, d, J = 2.4 Hz), 7.07 (1H, t, J = 7.5 Hz), 6.97 (1H, t, J = 7.4 Hz), 4.39 (2H, t, J = 7.2 Hz), 4.08 (2H, t, J = 7.2 Hz), 3.87 (2H, s), 3.07 (2H, t, J = 7.6 Hz). |

TABLE 2-26
| EX | STR | Prop | Data |
|---|---|---|---|
| 106 | 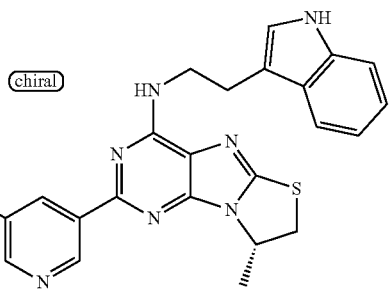 | 1 | NMR1 (400 MHz); 10.82 (1H, s), 9.37 (1H, s), 8.65 (1H, d, J = 2.9 Hz), 8.36 (1H, d, J = 10.1 Hz), 7.87 (1H, s), 7.65 (1H, d, J = 7.7 Hz), 7.34 (1H, d, J = 8.0 Hz), 7.21 (1H, d, J = 2.4 Hz), 7.07 (1H, t, J = 7.5 Hz), 6.98 (1H, t, J = 7.4 Hz), 4.97-4.86 (1H, m), 4.20 (1H, dd, J = 11.2, 7.1 Hz), 3.87 (2H, s), 3.72 (1H, dd, J = 11.2, 6.1 Hz), 3.06 (2H, t, J = 7.6 Hz), 1.68 (3H, d, J = 6.3 Hz). |
| 107 | 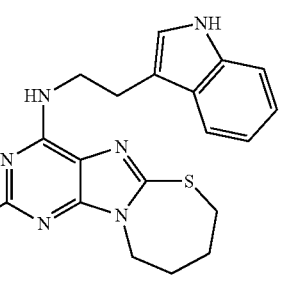 | 1 | NMR1 (500 MHz); 10.82 (1H, s), 9.43 (1H, s), 8.66 (1H, d, J = 2.9 Hz), 8.43 (1H, d, J = 10.0 Hz), 8.25-8.19 (1H, m), 7.64 (1H, d, J = 7.9 Hz), 7.33 (1H, d, J = 8.0 Hz), 7.22 (1H, d, J = 2.3 Hz), 7.10-7.03 (1H, m), 6.98 (1H, t, J = 7.4 Hz), 4.44-4.39 (2H, m), 3.93-3.85 (2H, m), 3.07 (2H, t, J = 7.7 Hz), 3.00-2.95 (2H, m), 2.20-2.12 (2H, m), 1.91-1.85 (2H, m). |
| 108 | 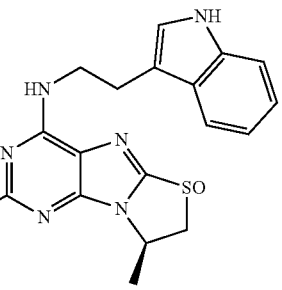 | 1 | MS m/z 462.38 (M + 1). |
| 109 | 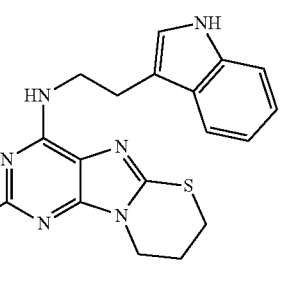 | 1 | NMR1 (500 MHz); 10.81 (1H, s), 9.39 (1H, s), 8.64 (1H, d, J = 2.9 Hz), 8.41-8.35 (1H, m), 7.93 (1H, s), 7.64 (1H, d, J = 7.7 Hz), 7.33 (1H, dd, J = 8.1, 0.9 Hz), 7.21 (1H, d, J = 2.3 Hz), 7.10-7.03 (1H, m), 6.98 (1H, t, J = 7.4 Hz), 4.27 (2H, t, J = 5.8 Hz), 3.87 (2H, s), 3.37-3.33 (2H, m), 3.06 (2H, t, J = 7.7 Hz), 2.36-2.30 (2H, m). |

TABLE 2-27

| EX | STR | Prop | Data |
|---|---|---|---|
| 110 | | 1 | NMR2 (400 MHz); 9.18-9.13 (1H, m), 8.26 (1H, dd, J = 9.6, 1.7 Hz), 8.04 (1H, s), 7.75-7.61 (4H, m), 7.39 (1H, dt, J = 8.1, 0.9 Hz), 7.25-7.09 (3H, m), 5.46 (1H, t, J = 5.8 Hz), 4.78 (2H, s), 4.10-4.03 (2H, m), 3.22-3.14 (2H, m), 1.82 (6H, s). |
| 111 | | 1 | NMR2 (500 MHz); 9.68-9.64 (1H, m), 8.61 (1H, dd, J = 9.3, 1.6 Hz), 8.39 (1H, s), 8.03 (1H, s), 7.77 (1H, d, J = 9.3 Hz), 7.69 (1H, d, J = 7.9 Hz), 7.38 (1H, d, J = 8.1 Hz), 7.24-7.10 (3H, m), 5.52-5.49 (1H, m), 4.79 (2H, s), 4.12-4.03 (2H, m), 3.21-3.15 (2H, m), 1.81 (6H, s). |
| 112 | | 17 | NMR1 (500 MHz); 9.41 (1H, s), 9.34 (1H, s), 8.62 (1H, d, J = 2.9 Hz), 8.38-8.32 (1H, m), 7.57-7.51 (3H, m), 7.40 (1H, t, J = 7.6 Hz), 7.32-7.26 (1H, m), 7.20 (1H, d, J = 2.2 Hz), 7.09 (1H, dd, J = 8.2, 2.2 Hz), 6.86 (1H, d, J = 8.2 Hz), 4.91 (2H, s), 3.78 (2H, s), 3.03-2.86 (8H, m), 1.71 (6H, s). |
| 113 | | 1 | NMR1 (500 MHz); 10.79 (1H, s), 7.95 (1H, t, J = 7.5 Hz), 7.64 (1H, d, J = 7.9 Hz), 7.51-7.41 (2H, m), 7.35-7.23 (3H, m), 7.17 (1H, d, J = 2.3 Hz), 7.08-7.02 (1H, m), 6.91 (1H, t, J = 7.4 Hz), 4.90 (2H, s), 3.76 (2H, s), 3.02 (2H, t, J = 7.7 Hz), 1.68 (6H, s). |
| 114 | | 1 | NMR1 (500 MHz); 10.81 (1H, s), 8.42-8.34 (2H, m), 7.64 (1H, d, J = 7.8 Hz), 7.39 (1H, s), 7.37-7.32 (1H, m), 7.32-7.23 (2H, m), 7.21 (1H, d, J = 2.3 Hz), 7.11-7.04 (1H, m), 7.02-6.95 (1H, m), 4.89 (2H, s), 3.85 (2H, s), 3.05 (2H, t, J = 7.6 Hz), 1.71 (6H, s). |

TABLE 2-28

| EX | STR | Prop | Data |
|---|---|---|---|
| 115 | | 1 | NMR1 (500 MHz); 10.78 (1H, s), 8.06-7.97 (1H, m), 7.62 (1H, d, J = 7.8 Hz), 7.46 (1H, s), 7.35-7.26 (2H, m), 7.21-7.13 (2H, m), 7.09-7.02 (1H, m), 6.93 (1H, t, J = 7.4 Hz), 4.90 (2H, s), 3.76 (2H, s), 3.05-2.98 (2H, m), 1.67 (6H, s). |
| 116 | | 1 | NMR1 (500 MHz); 10.82 (1H, s), 8.40-8.34 (2H, m), 7.67 (1H, d, J = 7.9 Hz), 7.50-7.40 (3H, m), 7.39-7.30 (2H, m), 7.22 (1H, d, J = 2.3 Hz), 7.11-7.04 (1H, m), 7.02-6.95 (1H, m), 4.90 (2H, s), 3.86 (2H, s), 3.09-3.02 (2H, m), 1.72 (6H, s). |
| 117 | | 1 | NMR1 (500 MHz); 10.79 (1H, s), 8.67-8.60 (2H, m), 7.82-7.76 (1H, m), 7.71 (1H, t, J = 7.8 Hz), 7.64 (1H, d, J = 7.8 Hz), 7.45 (1H, t, J = 6.0 Hz), 7.37-7.31 (1H, m), 7.19 (1H, d, J = 2.3 Hz), 7.10-7.03 (1H, m), 7.00-6.94 (1H, m), 4.91 (2H, s), 3.87 (2H, s), 3.07 (2H, t, J = 7.7 Hz), 1.72 (6H, s). |
| 118 | | 1 | NMR1 (500 MHz); 10.83 (1H, s), 8.22-8.15 (2H, m), 7.68 (1H, d, J = 7.9 Hz), 7.40-7.31 (3H, m), 7.27-7.19 (2H, m), 7.11-7.04 (1H, m), 7.01-6.94 (1H, m), 4.89 (2H, s), 3.84 (2H, s), 3.09-3.02 (2H, m), 2.39 (3H, s), 1.72 (6H, s). |
| 119 | | 1 | NMR1 (500 MHz); 10.83 (1H, s), 8.22 (1H, s), 8.19 (1H, d, J = 7.7 Hz), 7.67 (1H, d, J = 7.8 Hz), 7.40-7.32 (3H, m), 7.30-7.24 (1H, m), 7.21 (1H, d, J = 2.3 Hz), 7.11-7.04 (1H, m), 7.01-6.94 (1H, m), 4.89 (2H, s), 3.85 (2H, s), 3.09-3.02 (2H, m), 2.69 (2H, q, J = 7.6 Hz), 1.72 (6H, s), 1.23 (3H, t, J = 7.6 Hz). |

TABLE 2-29

| EX | STR | Prop | Data |
|---|---|---|---|
| 120 | | 1 | NMR1 (500 MHz); 10.80 (1H, s), 7.63 (1H, d, J = 7.9 Hz), 7.33 (1H, dt, J = 8.2, 1.0 Hz), 7.17 (1H, d, J = 2.3 Hz), 7.11 (1H, s), 7.10-7.01 (2H, m), 7.00-6.94 (1H, m), 4.84 (2H, s), 3.74 (2H, s), 2.99 (2H, dd, J = 9.0, 6.4 Hz), 2.56-2.50 (2H, m), 2.26-2.18 (2H, m), 1.74-1.54 (10H, m). |
| 121 | | 121 | NMR1 (500 MHz); 10.79 (1H, s), 7.74 (1H, d, J = 7.8 Hz), 7.34 (1H, d, J = 8.1 Hz), 7.20-7.10 (2H, m), 7.10-7.04 (1H, m), 7.01-6.94 (1H, m), 4.82 (2H, s), 3.71 (2H, s), 3.01-2.94 (2H, m), 2.65-2.57 (1H, m), 1.95-1.89 (2H, m), 1.82-1.75 (2H, m), 1.74-1.54 (9H, m), 1.43-1.31 (2H, m), 1.31-1.20 (1H, m). |
| 122 | | 1 | NMR1 (500 MHz); 9.31 (1H, s), 9.18 (1H, s), 8.47 (1H, s), 8.43 (1H, s), 7.70 (1H, s), 7.12-7.06 (2H, m), 6.72-6.66 (2H, m), 3.90 (2H, s), 3.71 (2H, s), 2.84 (2H, t, J = 7.6 Hz), 2.41 (3H, s), 1.79 (6H, s). |
| 123 | | 1 | NMR1 (500 MHz); 9.98 (1H, s), 9.34 (1H, s), 8.64 (1H, d, J = 2.8 Hz), 8.36 (1H, d, J = 10.2 Hz), 7.55 (1H, s), 7.10 (1H, s), 7.06-7.00 (1H, m), 6.75 (1H, d, J = 8.0 Hz), 4.91 (2H, s), 3.74 (2H, s), 2.88-2.78 (4H, m), 2.42-2.36 (2H, m), 1.71 (6H, s). MS m/z 474.42 (M + 1). |
| 124 | | 1 | NMR1 (500 MHz); 9.98 (1H, s), 9.29 (1H, s), 8.46 (1H, s), 8.41 (1H, s), 7.46 (1H, s), 7.10 (1H, s), 7.07-7.02 (1H, m), 6.76 (1H, d, J = 8.0 Hz), 4.90 (2H, s), 3.74 (2H, s), 2.89-2.79 (4H, m), 2.44-2.37 (5H, m), 1.71 (6H, s). |

TABLE 2-30

| EX | STR | Prop | Data |
|---|---|---|---|
| 125 | | 1 | NMR1 (500 MHz); 9.34 (1H, s), 8.63 (1H, d, J = 2.8 Hz), 8.38-8.32 (1H, m), 7.58-7.53 (1H, m), 7.35-7.28 (2H, m), 7.14-7.06 (2H, m), 4.91 (2H, s), 3.78 (2H, s), 2.95 (2H, t, J = 7.3 Hz), 1.72 (6H, s). |
| 126 | | 1 | NMR1 (500 MHz); 10.84 (1H, s), 9.13 (1H, s), 8.36 (1H, d, J = 2.9 Hz), 8.14 (1H, s), 7.64 (1H, d, J = 7.9 Hz), 7.56 (1H, s), 7.34 (1H, d, J = 8.1 Hz), 7.22 (1H, d, J = 2.3 Hz), 7.10-7.03 (1H, m), 6.96 (1H, t, J = 7.5 Hz), 4.91 (2H, s), 3.91-3.80 (5H, m), 3.05 (2H, t, J = 7.7 Hz), 1.72 (6H, s). |
| 127 | | 127 | NMR1 (500 MHz); 9.96 (1H, s), 9.34 (1H, s), 8.63 (1H, d, J = 2.8 Hz), 8.39-8.33 (1H, m), 7.52 (1H, s), 7.42-7.38 (1H, m), 7.07 (1H, dd, J = 8.3, 2.2 Hz), 6.84 (1H, d, J = 8.2 Hz), 4.91 (2H, s), 3.74 (2H, s), 2.84 (2H, t, J = 7.2 Hz), 1.71 (6H, s). |
| 128 | | 1 | NMR1 (500 MHz); 10.73 (1H, s), 9.27 (1H, s), 8.61 (1H, d, J = 2.9 Hz), 8.22-8.16 (1H, m), 7.79 (1H, d, J = 7.8 Hz), 7.27 (1H, d, J = 8.0 Hz), 7.21-7.08 (2H, m), 7.07-7.00 (1H, m), 7.00-6.94 (1H, m), 4.90 (2H, s), 3.93 (2H, s), 1.70 (6H, s), 0.99-0.94 (2H, m), 0.73-0.67 (2H, m). |
| 129 | | 1 | NMR2 (500 MHz); 9.99 (1H, d, J = 2.1 Hz), 9.12 (1H, d, J = 2.1 Hz), 8.15 (1H, d, J = 8.4 Hz), 8.04 (1H, s), 7.95 (1H, d, J = 8.1 Hz), 7.77-7.70 (2H, m), 7.60-7.54 (1H, m), 7.41-7.36 (1H, m), 7.24-7.11 (3H, m), 5.51 (1H, t, J = 6.1 Hz), 4.80 (2H, s), 4.16-4.08 (2H, m), 3.25-3.18 (2H, m), 1.84 (6H, s). |

TABLE 2-31

| EX | STR | Prop | Data |
|---|---|---|---|
| 130 | | 1 | NMR2 (500 MHz); 9.79 (1H, d, J = 1.8 Hz), 9.23 (2H, d, J = 2.0 Hz), 8.10 (1H, s), 7.68 (1H, d, J = 7.8 Hz), 7.37 (1H, d, J = 8.1 Hz), 7.23-7.10 (3H, m), 5.53 (1H, t, J = 5.8 Hz), 4.78 (2H, s), 4.10-4.03 (2H, m), 3.99 (3H, s), 3.18 (2H, t, J = 6.9 Hz), 1.81 (6H, s). |
| 131 | | 1 | NMR1 (500 MHz); 9.36 (1H, s), 9.27 (1H, s), 8.64 (1H, d, J = 2.9 Hz), 8.40-8.33 (1H, m), 7.53 (1H, s), 7.08 (1H, t, J = 7.7 Hz), 6.74-6.66 (2H, m), 6.59 (1H, ddd, J = 8.1, 2.5, 1.0 Hz), 4.91 (2H, s), 3.74 (2H, s), 2.86 (2H, t, J = 7.6 Hz), 1.72 (6H, s). |
| 132 | | 1 | NMR1 (500 MHz); 11.02 (1H, s), 9.34 (1H, s), 8.63 (1H, d, J = 2.8 Hz), 8.35-8.29 (1H, m), 7.73-7.46 (2H, m), 7.33 (1H, d, J = 8.5 Hz), 7.29 (1H, d, J = 2.4 Hz), 7.04 (1H, dd, J = 8.6, 2.1 Hz), 4.91 (2H, s), 3.84 (2H, s), 3.03 (2H, t, J = 7.4 Hz), 1.72 (6H, s). |
| 133 | | 1 | NMR2 (500 MHz); 8.71-8.67 (2H, m), 8.29-8.25 (2H, m), 8.05 (1H, s), 7.73-7.67 (1H, m), 7.41-7.35 (1H, m), 7.25-7.18 (1H, m), 7.17-7.11 (1H, m), 7.10 (1H, d, J = 2.3 Hz), 5.53-5.49 (1H, m), 4.78 (2H, s), 4.10-4.02 (2H, m), 3.21-3.14 (2H, m), 1.81 (6H, s). |

TABLE 2-32

| EX | STR | Prop | Data |
|---|---|---|---|
| 134 | | 1 | NMR2 (500 MHz); 9.24 (1H, d, J = 2.4 Hz), 8.74 (1H, td, J = 8.2, 2.4 Hz), 8.04 (1H, s), 7.68 (1H, d, J = 7.9 Hz), 7.37 (1H, d, J = 8.1 Hz), 7.24-7.18 (1H, m), 7.17-7.10 (1H, m), 7.09 (1H, d, J = 2.3 Hz), 6.96 (1H, dd, J = 8.5, 2.8 Hz), 5.49 (1H, t, J = 6.0 Hz), 4.77 (2H, s), 4.08-4.00 (2H, m), 3.16 (2H, t, J = 7.0 Hz), 1.79 (6H, s). |
| 135 | | 1 | NMR2 (500 MHz); 8.54-8.47 (1H, m), 8.27-8.21 (1H, m), 8.02 (1H, s), 7.68 (1H, dt, J = 8.0, 1.0 Hz), 7.37 (1H, dt, J = 8.1, 0.9 Hz), 7.29-7.23 (1H, m), 7.23-7.16 (1H, m), 7.15-7.06 (2H, m), 5.51-5.46 (1H, m), 4.77 (2H, s), 4.05-3.98 (2H, m), 3.19-3.12 (2H, m), 1.79 (6H, s). |
| 136 | | 62 | NMR2 (500 MHz); 9.41 (1H, d, J = 1.8 Hz), 8.58 (1H, t, J = 2.1 Hz), 8.53 (1H, d, J = 2.4 Hz), 8.03 (1H, s), 7.68 (1H, dd, J = 7.8, 1.1 Hz), 7.38 (1H, dt, J = 8.1, 0.9 Hz), 7.24-7.17 (1H, m), 7.17-7.11 (1H, m), 7.11 (1H, d, J = 2.3 Hz), 5.51-5.47 (1H, m), 4.78 (2H, s), 4.09-4.02 (2H, m), 3.21-3.14 (2H, m), 2.56 (3H, s), 1.80 (6H, s). |
| 137 | | 62 | NMR2 (500 MHz); 9.60 (1H, d, J = 1.9 Hz), 8.66-8.61 (2H, m), 8.08 (1H, s), 7.68 (1H, d, J = 7.9 Hz), 7.37 (1H, d, J = 8.1 Hz), 7.20 (1H, t, J = 7.7 Hz), 7.16-7.09 (2H, m), 5.54-5.51 (1H, m), 5.22 (2H, s), 4.77 (2H, s), 4.10-4.02 (2H, m), 3.18 (2H, t, J = 7.0 Hz), 2.11 (3H, s), 1.81 (6H, s). |

TABLE 2-33

| EX | STR | Prop | Data |
|---|---|---|---|
| 138 | | 62 | NMR2 (500 MHz); 9.51 (1H, d, J = 1.7 Hz), 8.50 (1H, d, J = 2.7 Hz), 8.44 (1H, s), 8.07 (1H, s), 7.70-7.65 (1H, m), 7.42-7.34 (1H, m), 7.24-7.17 (1H, m), 7.17-7.11 (1H, m), 7.09 (1H, d, J = 2.3 Hz), 6.61 (1H, t, J = 73.2 Hz), 5.54 (1H, s), 4.78 (2H, s), 4.09-4.01 (2H, m), 3.20-3.14 (2H, m), 1.80 (6H, s). |
| 139 | | 139 | NMR2 (400 MHz); 9.02 (1H, d, J = 1.7 Hz), 8.11 (1H, s), 8.05 (1H, d, J = 2.9 Hz), 7.91-7.85 (1H, m), 7.72-7.65 (1H, m), 7.40-7.33 (1H, m), 7.24-7.16 (1H, m), 7.16-7.07 (2H, m), 5.48 (1H, t, J = 5.9 Hz), 4.76 (2H, s), 4.10-4.00 (2H, m), 3.80 (1H, s), 3.21-3.13 (2H, m), 2.93 (3H, s), 1.80 (6H, s). |
| 140 | | 1 | NMR2 (400 MHz); 8.00 (1H, s), 7.89 (1H, dd, J = 3.6, 1.3 Hz), 7.75-7.68 (1H, m), 7.41-7.31 (2H, m), 7.25-7.17 (1H, m), 7.17-7.05 (3H, m), 5.39 (1H, t, J = 6.0 Hz), 4.74 (2H, s), 4.07-3.97 (2H, m), 3.20-3.12 (2H, m), 1.78 (6H, s). |
| 141 | | 1 | NMR2 (400 MHz); 8.13 (1H, dd, J = 3.1, 1.1 Hz), 8.03 (1H, s), 7.88 (1H, dd, J = 5.0, 1.2 Hz), 7.74-7.66 (1H, m), 7.40-7.34 (1H, m), 7.31 (1H, dd, J = 5.0, 3.1 Hz), 7.25-7.17 (1H, m), 7.17-7.10 (1H, m), 7.10-7.05 (1H, m), 5.39 (1H, t, J = 5.9 Hz), 4.74 (2H, s), 4.08-3.99 (2H, m), 3.19-3.11 (2H, m), 1.78 (6H, s). |

TABLE 2-34
| EX | STR | Prop | Data |
|----|-----|------|------|
| 142 | 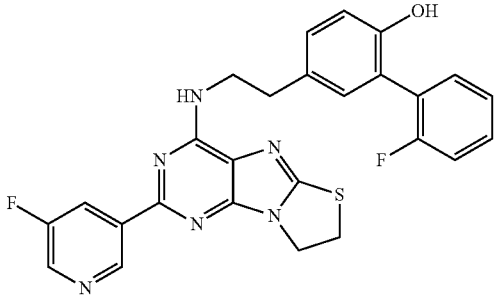 | 1 | NMR1 (400 MHz); 9.36-9.30 (2H, m), 8.63 (1H, d, J = 2.9 Hz), 8.37-8.29 (1H, m), 7.81 (1H, s), 7.39-7.29 (1H, m), 7.29-7.04 (5H, m), 6.83 (1H, d, J = 8.2 Hz), 4.42-4.34 (2H, m), 4.07 (2H, t, J = 7.2 Hz), 3.79 (2H, s), 2.90 (2H, t, J = 7.3 Hz). |
| 143 | 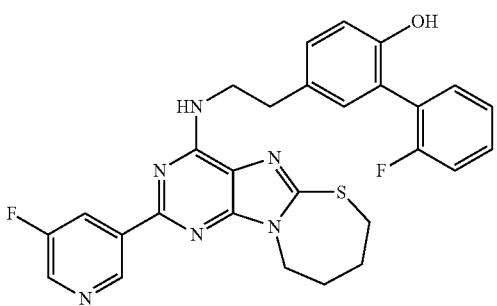 | 1 | NMR1 (400 MHz); 9.40 (1H, s), 9.32 (1H, s), 8.64 (1H, d, J = 2.8 Hz), 8.41 (1H, d, J = 10.0 Hz), 8.18-8.13 (1H, m), 7.39-7.29 (1H, m), 7.30-7.04 (5H, m), 6.83 (1H, d, J = 8.2 Hz), 4.44-4.37 (2H, m), 3.82 (2H, d, J = 7.1 Hz), 3.00-2.87 (4H, m), 2.18-2.14 (2H, m), 1.88-1.84 (2H, m). |
| 144 | 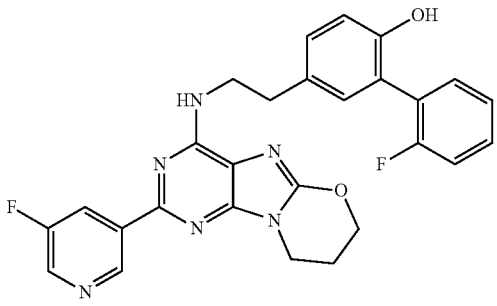 | 17 | NMR1 (500 MHz); 9.37-9.31 (2H, m), 8.61 (1H, s), 8.36-8.30 (1H, m), 7.55 (1H, s), 7.38-7.05 (6H, m), 6.84 (1H, d, J = 8.2 Hz), 4.57-4.52 (2H, m), 4.18-4.12 (2H, m), 3.78 (2H, s), 2.89 (2H, t, J = 7.3 Hz), 2.28-2.20 (2H, m). |
| 145 | 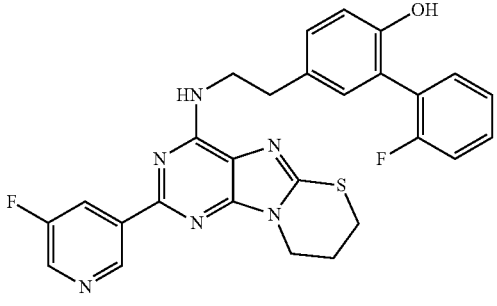 | 17 | NMR1 (500 MHz); 9.36 (1H, s), 9.32 (1H, s), 8.62 (1H, d, J = 2.8 Hz), 8.39-8.33 (1H, m), 7.86 (1H, s), 7.38-7.04 (6H, m), 6.83 (1H, d, J = 8.2 Hz), 4.29-4.23 (2H, m), 3.79 (2H, s), 3.39-3.28 (2H, m), 2.90 (2H, t, J = 7.4 Hz), 2.37-2.29 (2H, m). |
| 146 | 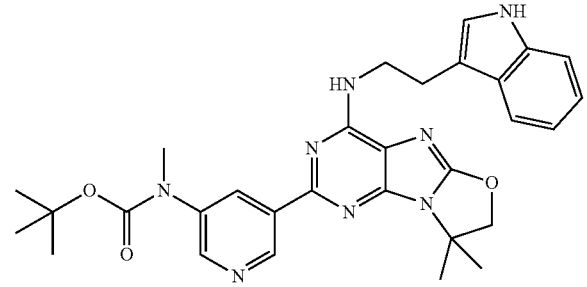 | 62 | NMR2 (500 MHz); 9.43 (1H, d, J = 1.8 Hz), 8.56-8.50 (2H, m), 8.06 (1H, s), 7.67 (1H, d, J = 7.8 Hz), 7.37 (1H, d, J = 8.1 Hz), 7.23-7.08 (3H, m), 5.49 (1H, t, J = 5.1 Hz), 4.78 (2H, s), 4.09-4.02 (2H, m), 3.34 (3H, s), 3.17 (2H, t, J = 6.9 Hz), 1.80 (6H, s), 1.45 (9H, s). |

Test Examples

The following shows the results of pharmacological test on the representative compound of the present invention and describes pharmacological effect on the compound, but the present invention is not limited to these test examples.

Test Example 1 (Aryl Hydrocarbon Receptor Antagonist Activity)

1. Production of AhR Reporter Cells

An expression vector, hCYP1A1/pGL4.27 was introduced into HepG2 cells (derived from American Type Culture Collection (ATCC)) that were seeded in 6-well plates (#3810-006 (Iwaki)) at $1.2 \times 10^6$ cells/well, using Lipofectamine 3000 (#100022050 (Invitrogen)). Referring to Garrion P M et al., Fundam Appl Toxicol, 30, 194 (1996), the vector hCYP1A1/pGL4.27 incorporated the human CYP1A1 promotor region including dioxin responsive element (DRE) region of the AhR binding region into the XhoI-BglII restriction enzyme site of pGL4.27 (#E8451 (Promega)). After 24 hours, medium-1 was replaced, and after 48 hours, the medium-1 containing hygromycin B (200 to 1000 μg/mL) was subjected to drug treatment. Culturing using the medium containing hygromycin B was continued for about 1 month to clone 24 clones showing drug resistance. A cell line showing high reporter activity was selected (DRE-Luc HepG2) from drug resistant lines using as an indicator luciferase activity (Dual-Glo Luciferase substrate, #E297A (Promega)) relative to an AhR agonist, 2,3,7,8-tetrachlorodibenzo-p-dioxin (TCDD) (#ED-901-B (CIL.)).

2. AhR Reporter Gene Assay

DRE-Luc HepG2 cells subcultured in a 225 cm² flask (#11-0005 (Iwaki)) were washed with PBS (#1419-144 (Gibco), Lot: 1896207), and thereto was added 8 mL of Trypsin-EDTA (0.05%) (#25300-054 (Gibco)). Thereafter, an excessive liquid was removed from the mixture, and the cells were stood at room temperature for 5 minutes. Thereto was added 10 mL of medium-2, the cells were recovered through a cell strainer (#352350 (Falcon), 70 μm), and the number of cells were then counted using a hemocytometer. A cell suspension was prepared at $3 \times 10^5$ cells/mL, 100 μL/well of the cell suspension was seeded into a 96-well white plate (#136101, F96 Microwell (Nunc)), and the cells were then cultured in a $CO_2$ incubator (5% $CO_2$, 37° C.). After 24 hours, the medium was aspirated, and thereto was added 100 μL of an assay medium solution including the compound of the present invention, and the cells were cultured in the $CO_2$ incubator (5% $CO_2$, 37° C.). After 24 hours, 11 μL of an assay medium solution including $5 \times 10^{-10}$ M TCDD (#ED-901-B (CIL.)) was added thereto and the cells were cultured in the $CO_2$ incubator (5% $CO_2$, 37° C.). After 24 hours, 50 μL of a reaction substrate (#E253B, Steady-Glo Luciferase substrate (Promega)) for Firefly Luciferase enzyme reaction was added to each well, and after 5 minute-shaking, the light emission intensity was measured with Wallac ARVO 1420sx (PerkinElmer).

Based on the concentration reaction curve relative to the enzyme reaction inhibition rate of Luciferase, $IC_{50}$ value and 95% reliable section of the compound of the present invention were calculated by a 4-Parameter Logistic Model of the statistical analysis software SAS (release 8.1 (SAS Institute Japan)).

Medium

Medium-1
MEM medium (Nacalai tesque, #21443-15, Lot: L8A4310) 500 mL
FBS (Gibco, #26140-079, FBS US origin, Lot: 1876851) 55 mL
Penicillin-Streptomycin Solution (100×) (Wako, #168-23191, Lot: APR7005) 5 mL
Sodium Pyruvate Solution (100×) (Nacalai tesque, #06977-34, Lot: L7N2959) 5 mL Medium-2
MEM medium (Nacalai tesque, #21443-15, Lot: L8A4310) 500 mL
FBS (Gibco, #26140-079, FBS US origin, Lot: 1876851) 55 mL
Penicillin-Streptomycin Solution (100×) (Wako, #168-23191, Lot: APR7005) 5 mL
Sodium Pyruvate Solution (100×) (Nacalai tesque, #06977-34, Lot: L7N2959) 5 mL
Hygromycin B (Invitrogen, #10687-010, Lot: H044-06US) 2 mL Assay Medium
MEM medium (Nacalai tesque, #21443-15, Lot: L8A4310) 500 mL
FBS (Gibco, #12676-029, Charcol Stripped FBS, Lot: 184-1094) 55 mL
Penicillin-Streptomycin Solution (100×) (Wako, #168-23191, Lot: APR7005) 5 mL
Sodium Pyruvate Solution (100×) (Nacalai tesque, #06977-34, Lot: L7N2959) 5 mL The results are shown in the following Table 3.

TABLE 3

| EX | AhR ($IC_{50}$ (nM)) |
|---|---|
| 1 | 4.4 |
| 2 | 9.5 |
| 3 | 2.9 |
| 4 | 5.0 |
| 5 | 36 |
| 6 | 10 |
| 7 | 9.1 |
| 8 | 0.11 |
| 9 | 0.32 |
| 10 | 11 |
| 11 | 6.4 |
| 12 | 12 |
| 13 | 29 |
| 14 | 11 |
| 15 | 5.5 |
| 16 | 3.9 |
| 17 | 2.3 |
| 18 | 6.9 |
| 20 | 0.058 |
| 21 | 0.033 |
| 22 | 9.8 |
| 23 | 9.6 |
| 24 | 3.9 |
| 25 | 4.4 |
| 26 | 1.0 |
| 27 | 0.35 |
| 28 | 0.40 |
| 29 | 0.37 |
| 30 | 0.78 |
| 31 | 0.46 |
| 32 | 29 |
| 35 | 12 |
| 36 | 0.70 |
| 37 | 0.53 |
| 38 | 0.49 |
| 39 | 1.2 |
| 40 | 40 |
| 41 | 10 |
| 42 | 6.1 |
| 43 | 26 |
| 44 | 3.5 |
| 45 | 11 |

TABLE 3-continued

| EX | AhR (IC50 (nM)) |
|---|---|
| 46 | 9.9 |
| 47 | 0.38 |
| 48 | 0.42 |
| 49 | 0.36 |
| 50 | 0.70 |
| 52 | 1.8 |
| 53 | 1.2 |
| 54 | 4.1 |
| 55 | 1.2 |
| 56 | 13 |
| 57 | 0.39 |
| 58 | 0.46 |
| 59 | 2.5 |
| 60 | 0.43 |
| 61 | 0.71 |
| 62 | 1.9 |
| 63 | 17 |
| 64 | 5.7 |
| 65 | 3.9 |
| 66 | 8.1 |
| 67 | 2.4 |
| 68 | 2.8 |
| 69 | 13 |
| 70 | 4.6 |
| 71 | 4.7 |
| 72 | 9.8 |
| 73 | 7.3 |
| 74 | 4.7 |
| 75 | 41 |
| 76 | 5.7 |
| 77 | 9.2 |
| 78 | 3.9 |
| 79 | 6.6 |
| 85 | 27 |
| 86 | 21 |
| 87 | 38 |
| 88 | 41 |
| 89 | 41 |
| 92 | 33 |
| 94 | 39 |
| 96 | 39 |
| 97 | 19 |
| 100 | 41 |
| 101 | 29 |
| 108 | 4.1 |
| 109 | 11 |
| 110 | 40 |
| 111 | 40 |
| 142 | 0.89 |
| 143 | 0.60 |
| 144 | 4.3 |
| 145 | 1.3 |

Test Example 2 (Platelet Production: Static Culturing)

The immortalized megakaryocyte line (SeV2-MKCL) obtained according to the method described in WO 2016/204256 was washed twice with D-PBS(−) and then cultured in medium not containing doxycycline to terminate forced expression. Culturing was implemented by seeding the cells at 1 mL/well in a 24-well plate (#662160 (Greiner Rio-One)) at a seeding density of $1 \times 10^5$ cells/mL followed by static culturing in the medium indicated below.

The medium was obtained by adding the following components to IMDM serving as the basal medium (concentrations indicate final concentrations).

FBS 15%
L-Glutamine 2 mM
ITS 100-fold dilution
MTG 450 μM
Ascorbic acid 50 μg/mL
SCF 50 ng/mL
TPO 50 ng/mL
ADAM inhibitor 15 μM
Y-27632 10 μM (#034-24024 (Wako Pure Chemical Industries, Ltd.))

Culturing was implemented under conditions of 37° C. and 5% $CO_2$. At the same time, the compound of the present invention (final concentration 0.1 μM) or DMSO (control) was added and cultured for 6 to 7 days. Thereafter, the number of platelets (CD41, CD42b, and CD42a-positive cells) was measured. The measurement method was as shown below. The same procedure was performed with the control.

A portion of the culture supernatant was harvested 6 to 7 days after culturing to terminate gene expression, and suspended with the following antibodies to stain them. eFluor 450-labeled anti-CD42a antibody (#48-0428-42 (eBioscience)) PE-labeled anti-CD42b antibody (#303906 (BioLegend)) APC-labeled anti-CD41 antibody (#303710 (BioLegend)) The number of platelets was counted using FACSVerse manufactured by BD 30 minutes after the stain reaction. In the measurement of the number of platelets, the number of cells was corrected using Flow-count beads (#7547053 (Beckman Coulter)).

The number of platelets produced from one megakaryocyte cell was calculated based on the number of platelets in the sample obtained by the FACS measurement, and the result was defined as platelet production efficiency (PLT/MK) and used for evaluation of drug efficacy of the compound. In addition, the specific activity at the time when the platelet production efficiency of the control was set to 1 was indicated as fold increase. The results are shown in the following Table 4.

TABLE 4

| EX | Static (vs veh) |
|---|---|
| 1 | 6.5 |
| 2 | 5.6 |
| 3 | 6.8 |
| 4 | 6.7 |
| 5 | 5.1 |
| 6 | 3.7 |
| 7 | 7.3 |
| 8 | 5.1 |
| 9 | 4.9 |
| 10 | 5.5 |
| 11 | 8.5 |
| 12 | 7.6 |
| 13 | 4.7 |
| 14 | 7.9 |
| 15 | 11 |
| 16 | 10 |
| 17 | 7.8 |
| 18 | 7.3 |
| 19 | 2.8 |
| 20 | 6.5 |
| 21 | 4.7 |
| 22 | 7.3 |
| 23 | 8.0 |
| 24 | 7.7 |
| 25 | 5.7 |
| 26 | 5.0 |
| 27 | 6.0 |
| 28 | 9.7 |
| 29 | 8.4 |
| 30 | 6.7 |
| 31 | 5.9 |
| 32 | 6.8 |
| 35 | 6.0 |

TABLE 4-continued

| EX | Static (vs veh) |
|---|---|
| 36 | 2.7 |
| 37 | 2.1 |
| 38 | 4.9 |
| 39 | 4.3 |
| 40 | 9.8 |
| 41 | 7.0 |
| 42 | 4.8 |
| 43 | 7.1 |
| 44 | 3.4 |
| 45 | 2.4 |
| 46 | 5.0 |
| 47 | 3.7 |
| 48 | 3.5 |
| 49 | 5.5 |
| 50 | 6.6 |
| 51 | 2.6 |
| 52 | 5.3 |
| 53 | 5.3 |
| 54 | 5.9 |
| 55 | 6.8 |
| 56 | 6.5 |
| 57 | 4.9 |
| 58 | 5.1 |
| 59 | 5.7 |
| 60 | 3.4 |
| 61 | 3.9 |
| 62 | 5.1 |
| 63 | 4.8 |
| 64 | 3.7 |
| 65 | 3.3 |
| 66 | 4.8 |
| 67 | 2.9 |
| 68 | 3.2 |
| 69 | 4.7 |
| 71 | 7.2 |
| 72 | 6.8 |
| 73 | 7.9 |
| 74 | 3.5 |
| 75 | 2.7 |
| 76 | 2.4 |
| 77 | 3.5 |
| 78 | 4.3 |
| 79 | 2.9 |
| 80 | 3.4 |
| 82 | 5.0 |
| 83 | 5.8 |
| 84 | 13 |
| 85 | 6.1 |
| 86 | 4.4 |
| 87 | 3.9 |
| 88 | 3.1 |
| 89 | 5.0 |
| 90 | 2.6 |
| 92 | 2.6 |
| 94 | 2.6 |
| 95 | 2.4 |
| 96 | 2.7 |
| 100 | 3.5 |
| 101 | 3.8 |
| 102 | 4.5 |
| 103 | 3.1 |
| 104 | 4.6 |
| 105 | 8.2 |
| 106 | 6.9 |
| 107 | 7.9 |
| 108 | 6.6 |
| 109 | 7.8 |
| 110 | 6.1 |
| 111 | 7.0 |
| 113 | 2.5 |
| 114 | 2.2 |
| 116 | 2.5 |

Test Example 3 (Platelet Production: Shake Culturing)

An experiment was conducted in the same manner as in Test Example 2, except that shake culturing at 100 rpm was performed after the cells were seeded in an E125 flask (#431143 (Corning)) instead of the 24-well plate at 25 mL/flask and a seeding density of $1 \times 10^5$ cells/mL to calculate the number of platelets produced in the compound (final concentration 0.1 µM) of the present invention.

INDUSTRIAL APPLICABILITY

The compound or a salt thereof of the present invention has an excellent aryl hydrocarbon receptor antagonist activity, so that it can promote production of platelets from platelet progenitor cells.

The invention claimed is:

1. A compound represented by general formula:

[Chem. 1]

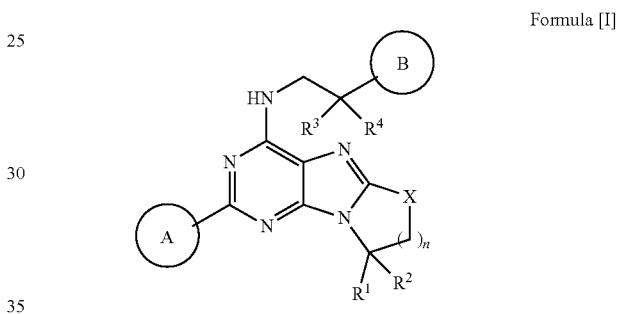

Formula [I]

wherein
R$^1$ and R$^2$ are the same or different and each independently represent hydrogen or C$_{1-6}$ alkyl;
R$^3$ and R$^4$ are the same or different and each independently represent hydrogen or C$_{1-6}$ alkyl, or R$^3$ and R$^4$ are bonded together to form C$_{2-5}$ alkylene;
X represents O, S, or S(O);
n represents 1, 2, or 3; and
rings A and B are the same or different and each independently represent an optionally substituted hydrocarbon ring or an optionally substituted heterocyclic ring, and the hydrocarbon ring and the heterocyclic ring are further optionally bonded with an optionally substituted hydrocarbon ring and/or an optionally substituted heterocyclic ring,
or a salt thereof.

2. The compound according to claim 1, wherein ring A is benzene, pyridine, cyclohexane, cyclohexene, thiophene, imidazopyridine, triazolopyridine, or quinoline, each of which is optionally substituted on the ring with 1 to 4 substituents which are the same or different and are each independently halogen, C$_{1-6}$ alkyl optionally substituted with halogen, —CN, —OR$^5$, —SR$^5$, —COOR$^5$, C$_{1-6}$ alkylene-CONR$^5$R$^6$, -C$_{1-6}$ alkylene-OCOR$^5$, —CONR$^5$R$^6$, —NR$^5$COOR$^6$, —SO$^2$R$^5$, or —NR$^5$R$^6$ (wherein R$^5$ and R$^6$ are the same or different and each independently represent hydrogen or C$_{1-6}$ alkyl optionally substituted with halogen), or a salt thereof.

3. The compound according to claim 2, wherein ring A is benzene or pyridine, each of which is optionally substituted on the ring with 1 to 4 substituents which are the same or different and are each independently halogen, $C_{1-6}$ alkyl optionally substituted with halogen, or —CN, or a salt thereof.

4. The compound according to claim 1, wherein ring B is benzene, biphenyl, pyridinylbenzene, thienylbenzene, benzothienylbenzene, indole, or 3,4-dihydro-1H-quinolin-2-one, each of which is optionally substituted on the ring with 1 to 4 substituents which the same or different and are each independently halogen, $C_{1-6}$ alkyl optionally substituted with halogen, —CN, —OR$^5$, —SR$^5$, —COOR$^5$, -C$_{1-6}$ alkylene-CONR$^5$R$^6$, -C$_{1-6}$ alkylene-OCOR$^5$, —CONR$^5$R$^6$, —NR$^5$COOR$^6$, —SO$^2$R$^5$, or —NR$^5$R$^6$ (wherein R$^5$ and R$^6$ are the same or different and each independently represent hydrogen or $C_{1-6}$ alkyl optionally substituted with halogen), or a salt thereof.

5. The compound according to claim 4, wherein ring B is benzene, biphenyl, pyridinylbenzene, thienylbenzene, benzothienylbenzene, or indole, each of which is optionally substituted on the ring with 1 to 4 substituents which are the same or different and are each independently halogen, $C_{1-6}$ alkyl optionally substituted with halogen, —CN, —OR$^5$, or -SO$^2$R$^5$ (wherein R$^5$ is hydrogen or $C_{1-6}$ alkyl optionally substituted with halogen), or a salt thereof.

6. The compound according to claim 1, wherein R$^1$ and R$^2$ are the same or different and are each independently hydrogen or methyl;

R$^3$ and R$^4$ each represent hydrogen;

X is O or S; and n is 1, or a salt thereof.

7. The compound according to claim 1, wherein ring B is represented by the following formulae:

[Chem. 2]

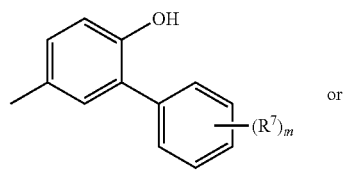

or

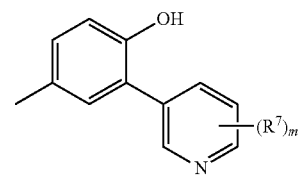

wherein R$^7$ is halogon, $C_{1-6}$ alkyl optionally substituted with halogen, —CN, —OR5, or -SO$^2$R$^5$ (wherein R$^5$ represents hydrogen or $C_{1-6}$ alkyl optionally substituted with halogen); and m is 0, 1, or 2, wherein when m is 2, R$^7$ each independently represents the same or different substituent, or a salt thereof.

8. The compound according to claim 1, which is a compound selected from the group consisting of the following compounds, or a salt thereof:

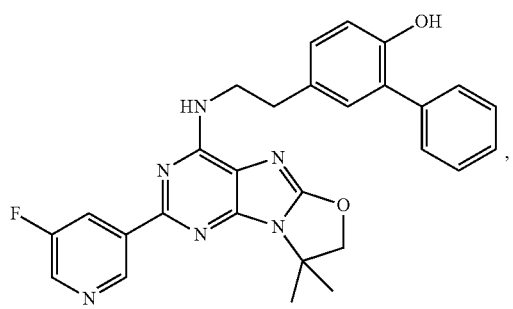

,

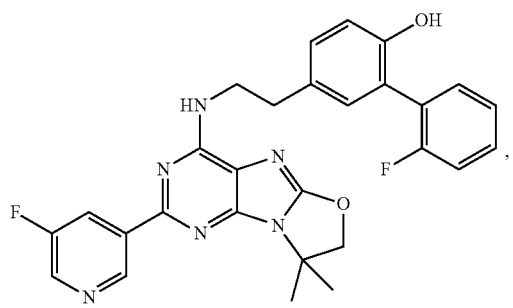

,

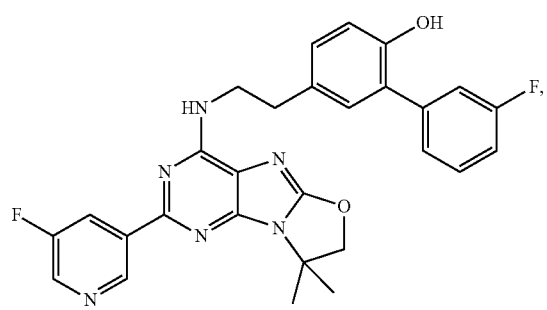

,

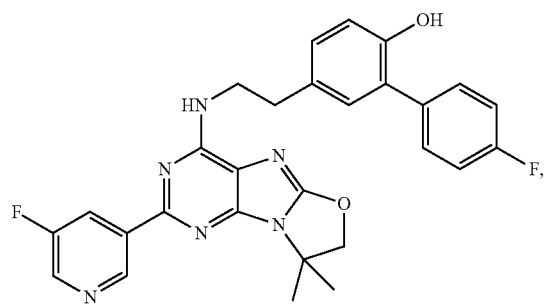

,

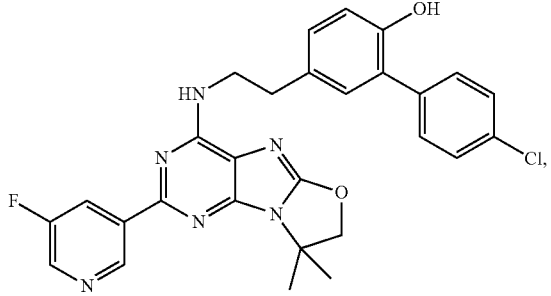

,

195
-continued
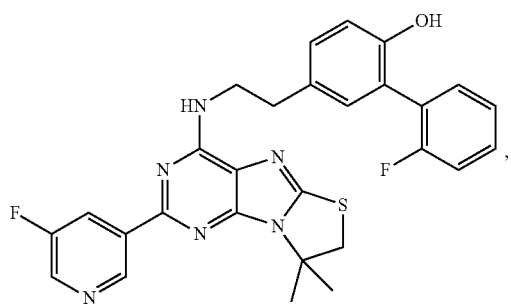
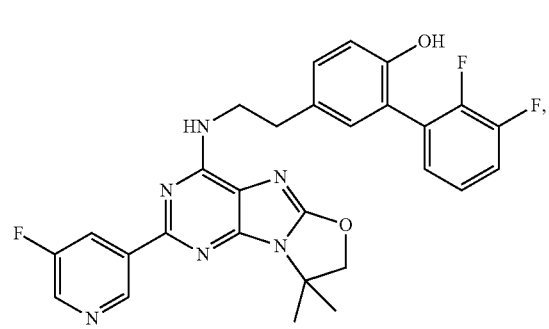
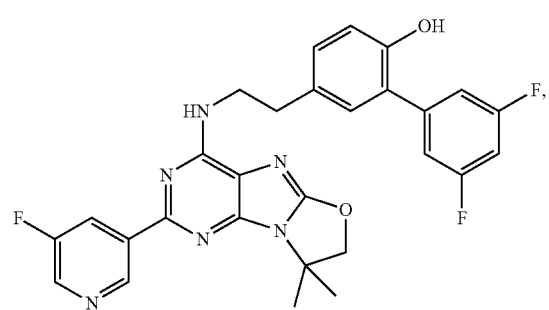
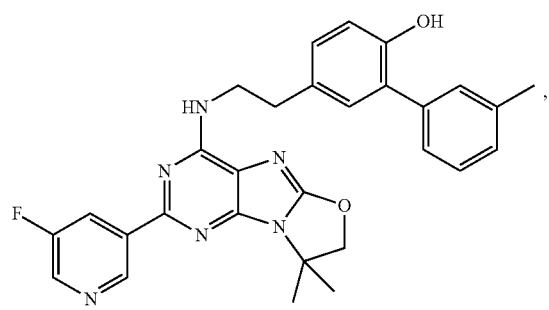
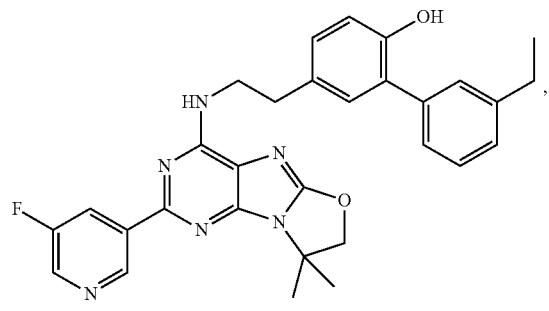
196
-continued
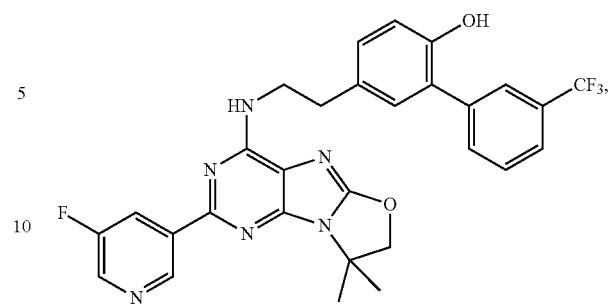
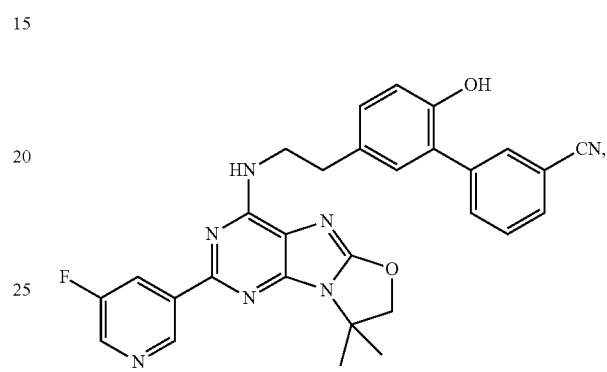
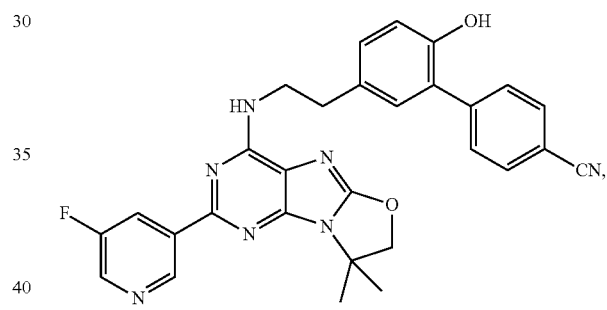
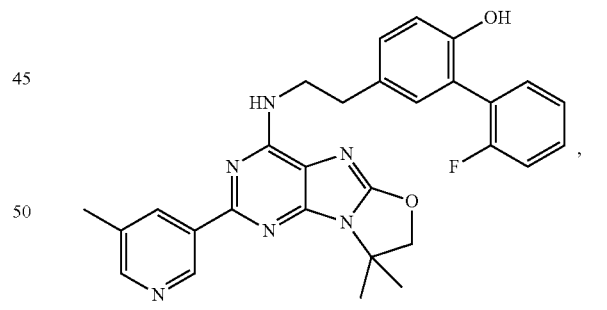
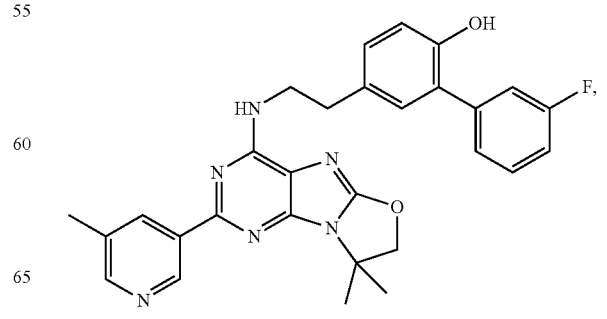

197
-continued
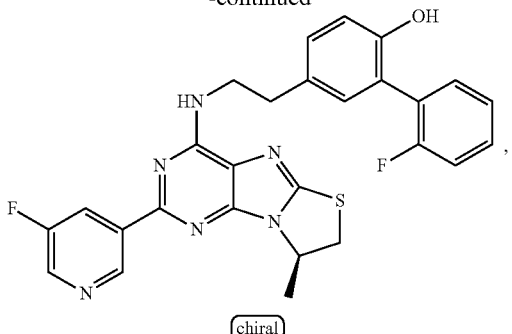
(chiral)
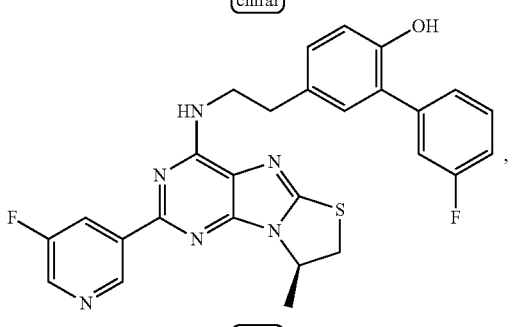
(chiral)
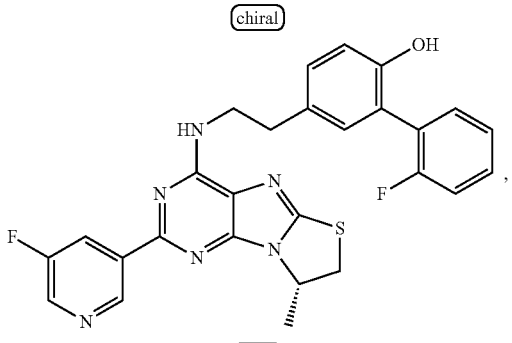
(chiral)
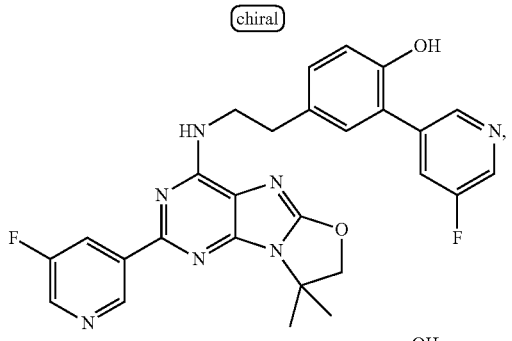
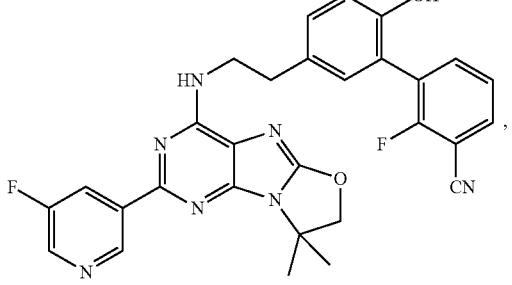
198
-continued
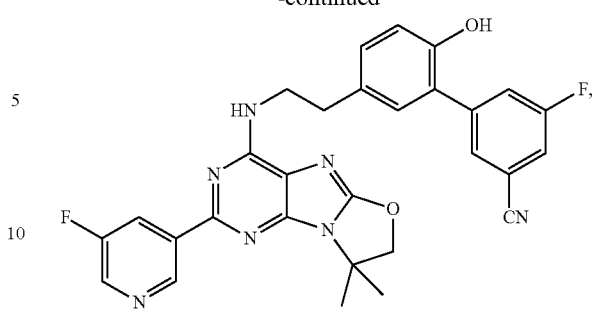
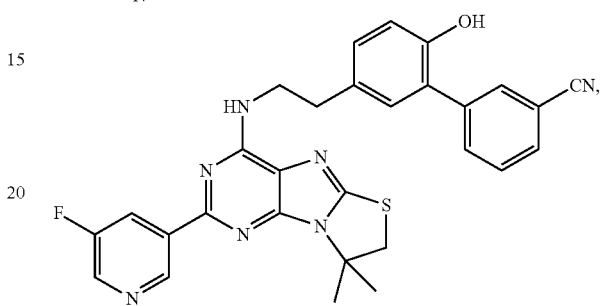
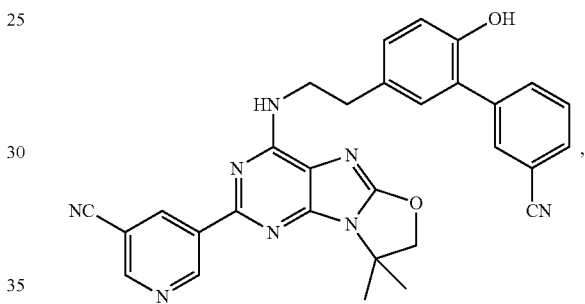
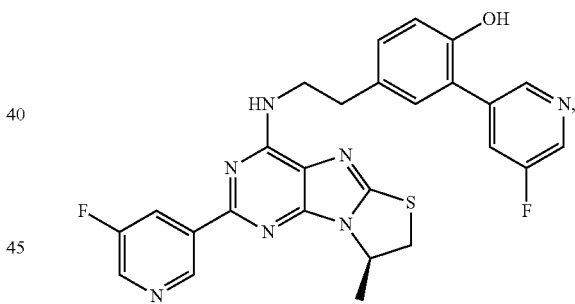
(chiral)
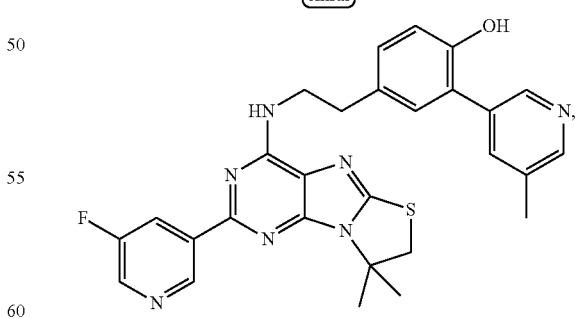
* * * * *